(12) United States Patent
Sever et al.

(10) Patent No.: US 9,360,491 B2
(45) Date of Patent: Jun. 7, 2016

(54) SYSTEMS AND METHODS FOR DETECTION AND QUANTIFICATION OF ANALYTES

(71) Applicant: CUE INC., San Diego, CA (US)

(72) Inventors: Clinton Sever, San Diego, CA (US); Ayub Khattak, San Diego, CA (US)

(73) Assignee: CUE INC., San Diego, CA (US)

( * ) Notice: Subject to any disclaimer, the term of this patent is extended or adjusted under 35 U.S.C. 154(b) by 0 days.

(21) Appl. No.: 14/599,369

(22) Filed: Jan. 16, 2015

(65) Prior Publication Data

US 2015/0129049 A1  May 14, 2015

Related U.S. Application Data

(63) Continuation of application No. PCT/US2014/023821, filed on Mar. 11, 2014.

(60) Provisional application No. 61/776,254, filed on Mar. 11, 2013.

(51) Int. Cl.
*F16K 17/14*  (2006.01)
*G01N 35/00*  (2006.01)
(Continued)

(52) U.S. Cl.
CPC ........ *G01N 35/00029* (2013.01); *B01L 3/5027* (2013.01); *B01L 3/502715* (2013.01);
(Continued)

(58) Field of Classification Search
CPC ............ F16K 99/0032; F16K 99/0036; F16K 99/0044
USPC ......... 137/251.1, 72, 74, 828; 251/129.04, 11
See application file for complete search history.

(56) References Cited

U.S. PATENT DOCUMENTS

D298,166 S  10/1988 Chennault
D302,585 S  8/1989 Elliott
(Continued)

FOREIGN PATENT DOCUMENTS

WO  WO 2012/170703 A1  12/2012
WO  WO 2013/136115 A1  9/2013
WO  WO 2013/144643 A2  10/2013

OTHER PUBLICATIONS

Cecchet, et al., Redox Mediation at 11-Mercaptoundecanoic Acid Self-Assembled Monolayers on Gold, J. Phys. Chem. B, 110:2241-2248 (2006).
US Office Action dated Jun. 19, 2015 in U.S. Appl. No. 14/599,375.
Yoshioka, et al., Suppression of Non-specific Adsorption Using Densified Tri(ethylene glycol) Alkanethiols: Monolayer Characteristics Evaluated by Electrochemical Measurements, Analytical Sciences, 26:33-37 (2010).

(Continued)

*Primary Examiner* — John K Fristoe, Jr.
*Assistant Examiner* — Umashankar Venkatesan
(74) *Attorney, Agent, or Firm* — Foley & Lardner LLP; Antoinette F. Konski; Christopher C. Bolten

(57) ABSTRACT

Devices, systems, and methods for detecting molecules of interest within a collected sample are described herein. In certain embodiments, self-contained sample analysis systems are disclosed, which include a reusable reader component, a disposable cartridge component, and a disposable sample collection component. In some embodiments, the reader component communicates with a remote computing device for the digital transmission of test protocols and test results. In various disclosed embodiments, the systems, components, and methods are configured to identify the presence, absence, and/or quantity of particular nucleic acids, proteins, or other analytes of interest, for example, in order to test for the presence of one or more pathogens or contaminants in a sample.

19 Claims, 44 Drawing Sheets

(51) Int. Cl.

| | | |
|---|---|---|
| *G01N 35/08* | (2006.01) | |
| *G01N 33/543* | (2006.01) | |
| *H04M 1/725* | (2006.01) | |
| *G01N 27/28* | (2006.01) | |
| *B05D 3/00* | (2006.01) | |
| *F16K 99/00* | (2006.01) | |
| *C12Q 1/68* | (2006.01) | |
| *G01N 33/58* | (2006.01) | |
| *B01L 3/00* | (2006.01) | |
| *G01N 1/02* | (2006.01) | |
| *G01N 35/10* | (2006.01) | |
| *G01N 21/78* | (2006.01) | |
| *G01N 27/327* | (2006.01) | |

(52) U.S. Cl.
CPC ..... *B01L3/502723* (2013.01); *B01L 3/502738* (2013.01); *B05D 3/002* (2013.01); *C12Q 1/6825* (2013.01); *F16K 99/0032* (2013.01); *F16K 99/0036* (2013.01); *G01N 27/28* (2013.01); *G01N 27/3271* (2013.01); *G01N 27/3273* (2013.01); *G01N 33/54306* (2013.01); *G01N 33/54326* (2013.01); *G01N 33/54333* (2013.01); *G01N 33/54366* (2013.01); *G01N 33/54373* (2013.01); *G01N 33/581* (2013.01); *G01N 35/0098* (2013.01); *G01N 35/08* (2013.01); *H04M 1/72527* (2013.01); *B01L 3/5029* (2013.01); *B01L 2200/026* (2013.01); *B01L 2200/027* (2013.01); *B01L 2200/028* (2013.01); *B01L 2200/0668* (2013.01); *B01L 2200/0684* (2013.01); *B01L 2200/0689* (2013.01); *B01L 2200/087* (2013.01); *B01L 2200/10* (2013.01); *B01L 2200/16* (2013.01); *B01L 2300/044* (2013.01); *B01L 2300/0627* (2013.01); *B01L 2300/0645* (2013.01); *B01L 2300/087* (2013.01); *B01L 2300/0816* (2013.01); *B01L 2300/0867* (2013.01); *B01L 2300/1827* (2013.01); *B01L 2400/0406* (2013.01); *B01L 2400/0487* (2013.01); *B01L 2400/0677* (2013.01); *B01L 2400/0683* (2013.01); *B05D 2518/00* (2013.01); *F16K 2099/0084* (2013.01); *G01N 1/02* (2013.01); *G01N 21/78* (2013.01); *G01N 27/3272* (2013.01); *G01N 35/1095* (2013.01); *G01N 2001/027* (2013.01); *G01N 2001/028* (2013.01); *G01N 2035/00277* (2013.01); *G01N 2035/00564* (2013.01); *G01N 2458/30* (2013.01); *Y10T 137/1797* (2015.04)

(56) References Cited

U.S. PATENT DOCUMENTS

| | | | |
|---|---|---|---|
| 5,708,247 A | 1/1998 | McAleer et al. | |
| 5,935,804 A | 8/1999 | Laine et al. | |
| 6,523,560 B1 * | 2/2003 | Williams et al. | ......... F16K 31/02 137/14 |
| D472,975 S | 4/2003 | Iori et al. | |
| 6,893,879 B2 | 5/2005 | Petersen et al. | |
| 7,118,667 B2 | 10/2006 | Lee | |
| 7,195,036 B2 | 3/2007 | Burns et al. | |
| D542,931 S | 5/2007 | Pukali et al. | |
| 7,285,412 B2 | 10/2007 | Casagrande et al. | |
| 7,291,497 B2 | 11/2007 | Holmes et al. | |
| 7,432,106 B2 | 10/2008 | Cox | |
| 7,478,792 B2 * | 1/2009 | Oh et al. | ......... 251/11 |
| D591,864 S | 5/2009 | Schmidt | |
| D600,578 S | 9/2009 | Tsuji | |
| 7,635,594 B2 | 12/2009 | Holmes et al. | |
| 7,888,125 B2 | 2/2011 | Gibbons et al. | |
| 7,981,696 B2 | 7/2011 | Moreland et al. | |
| 8,007,999 B2 | 8/2011 | Holmes et al. | |
| 8,008,034 B2 | 8/2011 | Gibbons et al. | |
| 8,012,744 B2 | 9/2011 | Gibbons et al. | |
| D646,189 S | 10/2011 | Dinter et al. | |
| 8,071,054 B2 | 12/2011 | Oh et al. | |
| 8,101,402 B2 | 1/2012 | Holmes | |
| 8,202,697 B2 | 6/2012 | Holmes | |
| 8,216,832 B2 | 7/2012 | Battrell et al. | |
| 8,265,955 B2 | 9/2012 | Michelson et al. | |
| 8,283,155 B2 | 10/2012 | Holmes et al. | |
| 8,361,808 B2 | 1/2013 | Wang | |
| D679,025 S | 3/2013 | Motadel et al. | |
| 8,435,738 B2 | 5/2013 | Holmes | |
| 8,449,842 B2 | 5/2013 | Knopp et al. | |
| 8,470,524 B2 | 6/2013 | Gibbons et al. | |
| 8,475,739 B2 | 7/2013 | Holmes et al. | |
| 8,551,714 B2 | 10/2013 | Jovanovich et al. | |
| 8,562,918 B2 | 10/2013 | Jovanovich et al. | |
| 8,669,047 B2 | 3/2014 | Holmes et al. | |
| 8,679,407 B2 | 3/2014 | Holmes et al. | |
| D707,847 S | 6/2014 | Motadel et al. | |
| 8,741,230 B2 | 6/2014 | Holmes et al. | |
| 8,778,665 B2 | 7/2014 | Gibbons et al. | |
| D718,462 S | 11/2014 | Cook et al. | |
| D719,666 S | 12/2014 | Manian | |
| 2002/0002326 A1 | 1/2002 | Causey et al. | |
| 2002/0137234 A1 | 9/2002 | Wohlstadter et al. | |
| 2003/0019522 A1 * | 1/2003 | Parunak | ..................... 137/251.1 |
| 2004/0173456 A1 | 9/2004 | Boos et al. | |
| 2004/0189311 A1 | 9/2004 | Glezer et al. | |
| 2005/0136529 A1 | 6/2005 | Yang et al. | |
| 2005/0178700 A1 | 8/2005 | Tyvoll et al. | |
| 2006/0131994 A1 | 6/2006 | D'Angelico et al. | |
| 2006/0243591 A1 | 11/2006 | Plotkin et al. | |
| 2007/0154922 A1 | 7/2007 | Collier et al. | |
| 2007/0184547 A1 | 8/2007 | Handique et al. | |
| 2008/0124779 A1 | 5/2008 | Oh et al. | |
| 2008/0160601 A1 * | 7/2008 | Handique | ................ C12M 1/34 435/287.2 |
| 2008/0160622 A1 | 7/2008 | Su et al. | |
| 2008/0160630 A1 | 7/2008 | Liu et al. | |
| 2008/0182301 A1 * | 7/2008 | Handique et al. | ............ 435/91.2 |
| 2008/0302193 A1 | 12/2008 | Bommarito et al. | |
| 2009/0061450 A1 | 3/2009 | Hunter | |
| 2010/0236340 A1 | 9/2010 | Lee et al. | |
| 2010/0297708 A1 | 11/2010 | Collier et al. | |
| 2010/0331652 A1 | 12/2010 | Groll et al. | |
| 2011/0059468 A1 | 3/2011 | Earhart et al. | |
| 2011/0129841 A1 | 6/2011 | Heid et al. | |
| 2011/0165562 A1 | 7/2011 | Pourahmadi et al. | |
| 2011/0171754 A1 | 7/2011 | Redmond et al. | |
| 2012/0009588 A1 | 1/2012 | Rajagopal et al. | |
| 2012/0071342 A1 | 3/2012 | Lochhead et al. | |
| 2012/0164036 A1 | 6/2012 | Stern et al. | |
| 2012/0180580 A1 | 7/2012 | Immink et al. | |
| 2012/0190589 A1 | 7/2012 | Anderson et al. | |
| 2012/0267258 A1 | 10/2012 | Uraoka et al. | |
| 2012/0271127 A1 | 10/2012 | Battrell et al. | |
| 2013/0011210 A1 | 1/2013 | Toner et al. | |
| 2013/0085680 A1 | 4/2013 | Arlen et al. | |
| 2013/0244339 A1 | 9/2013 | Ehrenkranz et al. | |
| 2013/0273528 A1 | 10/2013 | Ehrenkranz | |
| 2013/0309778 A1 | 11/2013 | Lowe et al. | |
| 2014/0027286 A1 | 1/2014 | Ikegami et al. | |
| 2014/0030717 A1 | 1/2014 | Zhong et al. | |
| 2014/0194305 A1 | 7/2014 | Kayyem et al. | |

OTHER PUBLICATIONS

Notice of Allowance in U.S. Appl. No. 14/479,149, mailed Mar. 6, 2015, 13 pages.
Non-Final Office Action in U.S. Appl. No. 14/599,372, mailed Mar. 27, 2015, 11 pages.
Final Office Action in U.S. Appl. No. 14/205,146, mailed Apr. 3, 2015, 8 pages.
Notice of Allowance in U.S. Appl. No. 14/543,842, mailed Apr. 24, 2015, 8 pages.
Notice of Allowance in U.S. Appl. No. 14/599,365, mailed May 1, 2015, 8 pages.

(56) References Cited

OTHER PUBLICATIONS

Restriction Requirement in Design U.S. Appl. No. 29/460,660, mailed Jun. 2, 2015, 8 pages.
U.S. Appl. No. 14/205,146, filed Mar. 11, 2014, Cue Inc.
U.S. Appl. No. 14/479,149, filed Sep. 5, 2014, Cue Inc.
U.S. Appl. No. 14/543,842, filed Nov. 17, 2014, Cue Inc.
U.S. Appl. No. 14/599,365, filed Jan. 16, 2015, Cue Inc.
U.S. Appl. No. 14/599,372, filed Jan. 16, 2015, Cue Inc.
U.S. Appl. No. 14/599,375, filed Jan. 16, 2015, Cue Inc.
U.S. Appl. No. 29/490,660, filed May 12, 2014, Cue Inc.
Anderson, J.C. et al. (2008) "Thermally-Actuated Microfluidic Systems," JALA 13:65-72.
Beyor, N. et al. (2008) "Immunomagnetic bead-based cell concentration microdevice for dilute pathogen detection," Biomed Microdevices 10:909-917.
Chen, Z. et al. (2005) "Thermally-actuated, phase change flow control for microfluidic systems," Lab Chip 5:1277-1285.
Cho, H. et al. (2007) "How the capillary burst microvalve works," Journal of Colloid and Interface Science 306:379-385.
Clinical IVD Products: Liat™ Analyzer; IQuum, Inc.: http://www.iquum.com/products/analyzer.shtml. Last accessed May 5, 2014.
Fan, R. et al. (2008) "Integrated barcode chips for rapid, multiplexed analysis of proteins in microliter quantities of blood," Nature Biotechnology 26(12):1373-1378.
Ferguson, B.S. et al. (2009) "Integrated Microfluidic Electrochemical DNA Sensor," Anal. Chem. 81:6503-6508.
Henares, T.G. et al. (2007) "Integration of Multianalyte Sensing Functions on a Capillary-Assembled Microchip: Simultaneous Determination of Ion Concentrations and Enzymatic Activities by a "Drop-and-Sip" Technique," Anal. Chem. 79:908-915.
International Search Report and Written Opinion (ISA/KR) for International Application No. PCT/US2014/023821, dated Jul. 7, 2014, 12 pages.
Jagannathan, H. et al. (2001) "Micro-Fluidic Channels with Integrated Ultrasonic Transducers," IEEE Ultrasonics Symposium:859-862.
Kaigala, G.V. et al. (2008) "Electrically controlled microvalves to integrate microchip polymerase chain reaction and capillary electrophoresis," Lab Chip 8:1071-1078.
Kim, D. et al. (2007) "A Bi-Polymer Micro One-Way Valve," Sensors and Actuators A 136:426-433.
Kinoshita, T. et al. (2007) "Functionalization of Magnetic Gold/Iron-Oxide Composite Nanoparticles with Oligonucleotides and Magnetic Separation of Specific Target," J. of Magnetism and Magnetic Materials 311:255-258.
Kwakye, S. et al. (2006) "Electrochemical Microfluidic Biosensor for Nucleic Acid Detection with Integrated Minipotentiostat," Biosensors and Bioelectronics 21: 2217-2223.
Laschi, S. et al. (2010) "A New Gravity-Driven Microfluidic-Based Electrochemical Assay Coupled to Magnetic Beads for Nucleic Acid Detection," Electrophoresis 31: 3727-3736.
Lawi, W. et al. (2009) "A Microfluidic Cartridge System for Multiplexed Clinical Analysis," J. Assoc. Laboratory Automation 14(6):407-412.
Lee, C.S. et al. (2001) "Microelectromagnets for the Control of Magnetic Nanoparticles," Applied Physics Letters 79(20):3308-3310.
Lillehoj, P.B. et al. (2010) "A Self-Pumping Lab-on-a-Chip for Rapid Detection of Botulinum Toxin," Lab Chip 10: 2265-2270.
Liu, R.H. et al. (2004) "Self-Contained, Fully Integrated Biochip for Sample Preparation, Polymerase Chain Reaction Amplification, and DNA Microarray Detection," Analytical Chemistry 76(7):1824-1831.
Liu, R.H. et al. (2004) "Single-use, Thermally Actuated Paraffin Valves for Microfluidic Applications," Sensors and Actuators B 98:328-336.
Marentis, T.C. et al. (2005) "Microfluidic Sonicator for Real-Time Disruption of Eukaryotic Cells and Bacterial Spores for DNA Analysis," Ultrasound in Med. & Biol. 31(9):1265-1277.
Mrksich, M. et al. (1997) "Using Self-Assembled Monolayers that Present Oligo(ethylene glycol) Groups to Control the Interactions of Proteins with Surfaces," American Chemical Society Symposium Series 680:361-373.
Rida, A. et al. (2004) "Manipulation of Self-Assembled Structures of Magnetic Beads for Microfluidic Mixing and Assaying," Analytical Chemistry 76(21):6239-6246.
Roderee, K. et al. (2011) "DNA Hybridization Enhancement Using Piezoelectric Microagitation through a Liquid Coupling Medium," Lab Chip, doi:10.1039/COLC00419G.
Sharma, V. et al. (2007) "Surface Characterization of Plasma-Treated and PEG-Grafted PDMS for Micro Fluidic Applications," Vacuum 81:1094-1100.
Shin, Y.S. et al. (2010) "Chemistries for Patterning Robust DNA MicroBarcodes Enable Multiplex Assays of Cytoplasm Proteins from Single Cancer Cells," ChemPhysChem 11:3063-3069.
Simplexa™ Flu A/B & RSV Direct Kit; Focus Diagnostics, Inc.: https://www.focusdx.com/product/MOL2650. Last accessed May 5, 2014.
Taylor, M.T. et al. (2001) "Lysing Bacterial Spores by Sonication through a Flexible Interface in a Microfluidic System," Analytical Chemistry 73(3):492-496.
The FilmArray System; Biofire Diagnostics, Inc.: http://filmarray.com/the-panels/. Last accessed May 5, 2014.
Wang, J. (2002) "Portable Electrochemical Systems," Trends in Analytical Chemistry 21(4):226-232.
Wang, J. et al. (2005) "Self-Actuated, Thermo-Responsive Hydrogel Valves for Lab on a Chip," Biomedical Microdevices 7(4):313-322.
Wang, J. et al. (2010) "A Self-Powered, One-Step Chip for Rapid, Quantitative and Multiplexed Detection of Proteins from Pinpricks of Whole Blood," Lab Chip 10:3157-3162.
Wu, C. et al. (2011) "Ultrasonication on a Microfluidic Chip to Lyse Single and Multiple Pseudo-Nitzschia for Marine Biotoxin Analysis," Biotechnology Journal 6:150-155.
Xpert® Flu; Cepheid: http://www.cepheid.com/us/cepheid-solutions/clinical-ivd-tests/critical-infectious-diseases/xpert-flu. Last accessed May 5, 2014.
Ziegler, J. et al. (2008) "High-Performance Immunoassays Based on Through-Stencil Patterned Antibodies and Capillary Systems," Analytical Chemistry 80(5):1763-1769.
Non-Final Office Action in U.S. Appl. No. 14/205,146, mailed Sep. 26, 2014, 6 pages.
Non-Final Office Action in U.S. Appl. No. 14/479,149, mailed Jan. 13, 2015, 17 pages.
Non-Final Office Action in U.S. Appl. No. 14/543,842, mailed Feb. 12, 2015, 11 pags.
Office Action in Design U.S. Appl. No. 29/490,660, mailed Jun. 25, 2014, 6 pages.
Notice of Allowance dated Aug. 20, 2015 in Design U.S. Appl. No. 29/490,660.
US Notice of Allowance dated Aug. 26, 2015 in U.S. Appl. No. 14/599,375.
US Notice of Allowance dated Sep. 14, 2015 in U.S. Appl. No. 14/599,372.
US Notice of Allowance dated Oct. 22, 2015 in U.S. Appl. No. 14/205,146.
Supplementary Partial European Search Report in European Application No. 14779852.4, mailed Feb. 11, 2016.
Lomas, N. (2014) "Cue is a Connected Lab-In-A-Box for On-Demand Health Testing at Home," TechCrunch.
Prindle, D. (2014) "Sick? Need more vitamin D? Testosterone? Lick a stick and Cue fills you in," www.digitaltrends.com.
International Search Report and Written Opinion (ISA/EP) for International Application No. PCT/US2015/049439, mailed Dec. 7, 2015, 15 pages.
Non-Final Office Action in U.S. Appl. No. 14/954,817, mailed Feb. 2, 2016.
U.S. Appl. No. 29/545,014, filed Nov. 9, 2015, Cue Inc.
Non-Final Office Action in U.S. Appl. No. 14/205,146, mailed Apr. 6, 2016.

\* cited by examiner

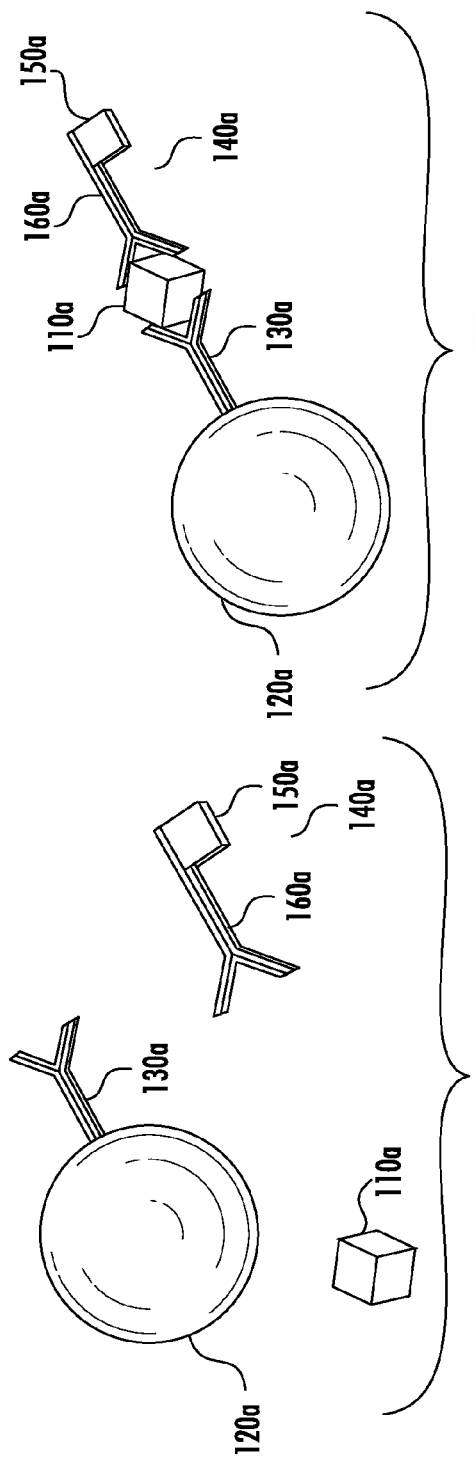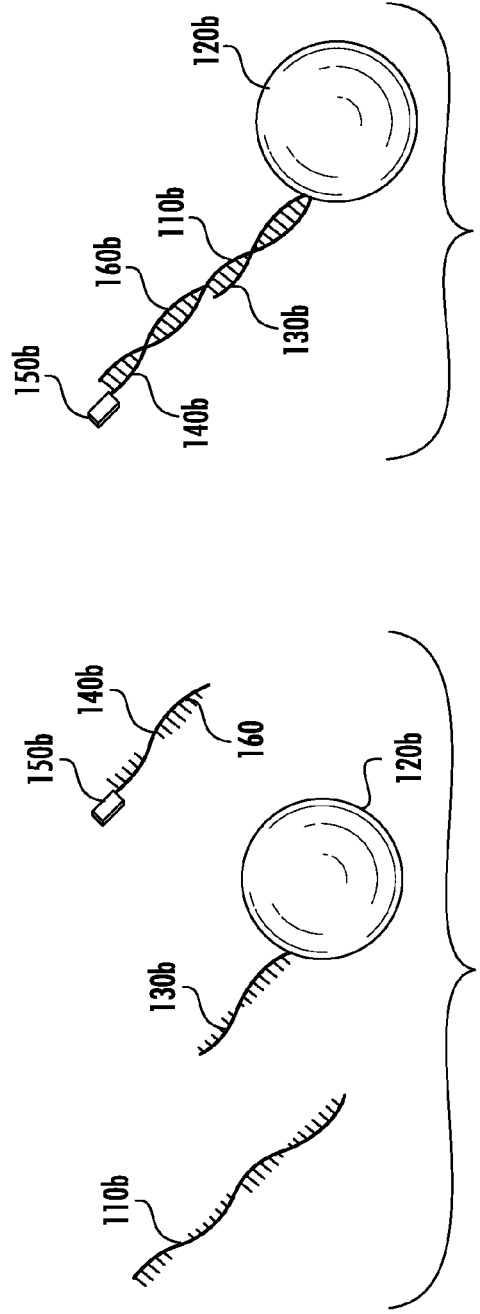

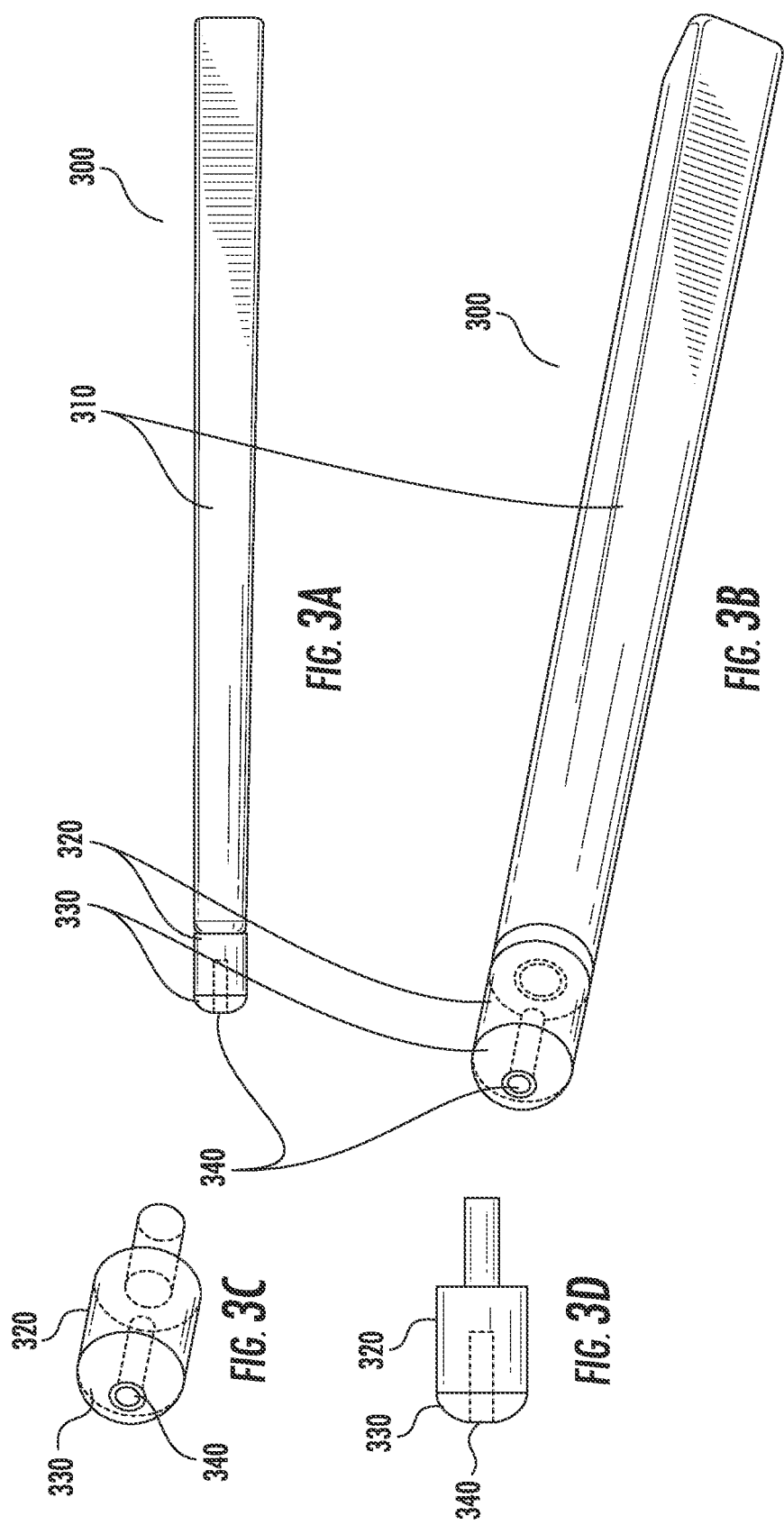

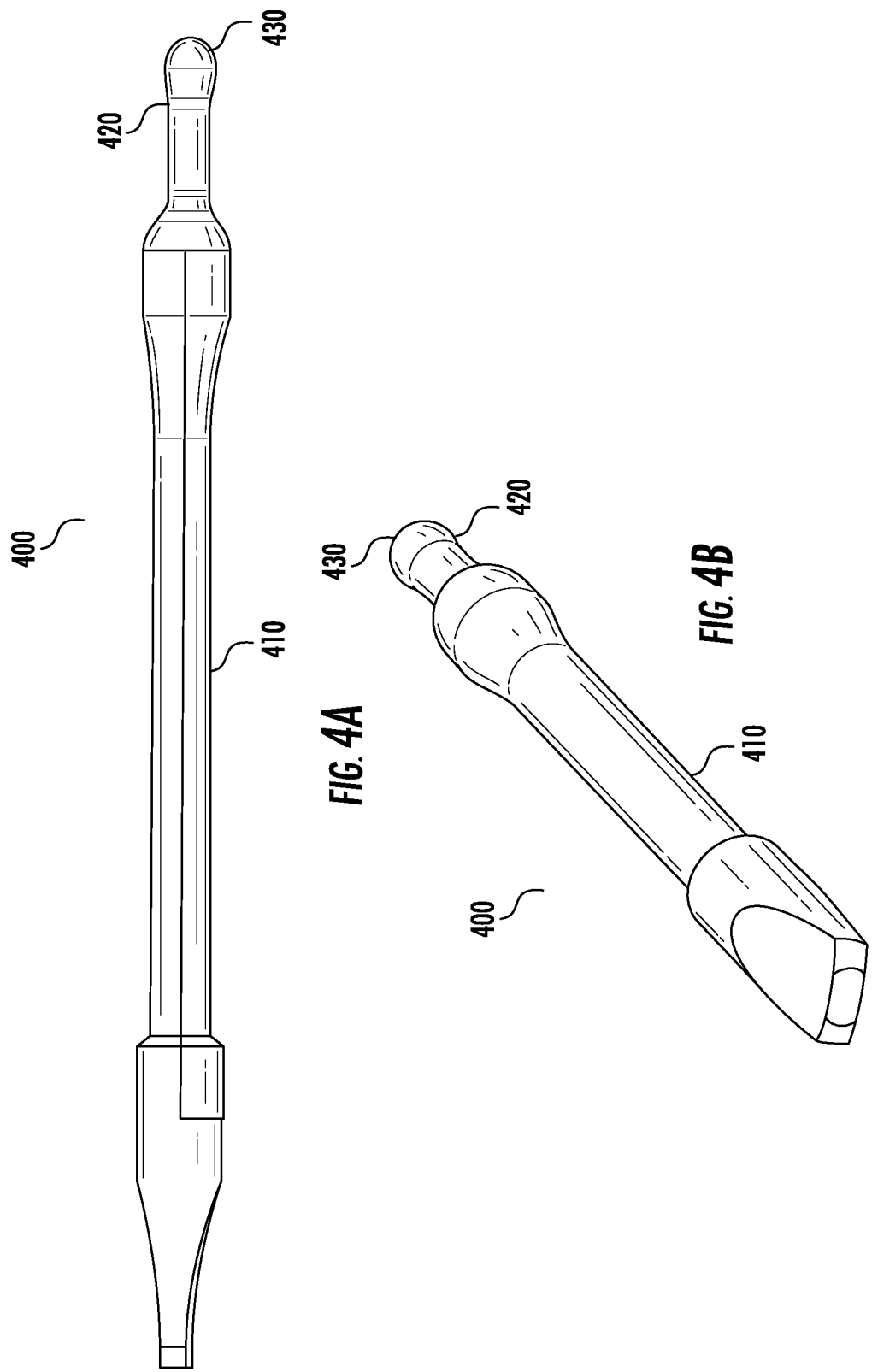

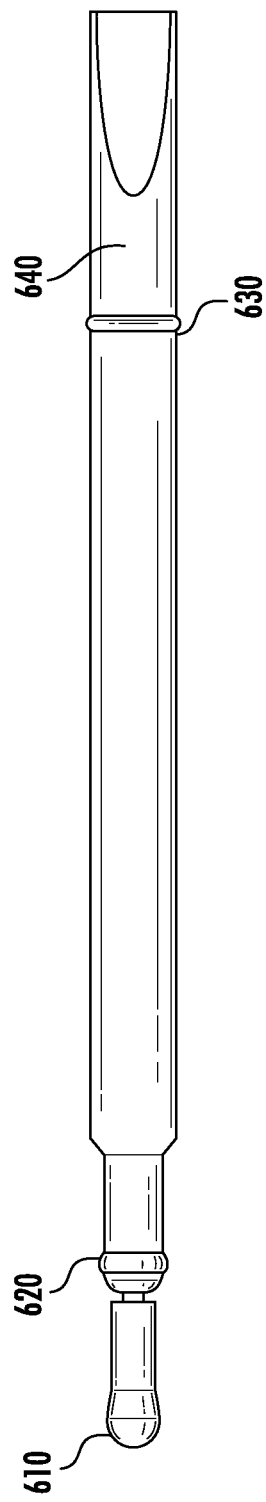

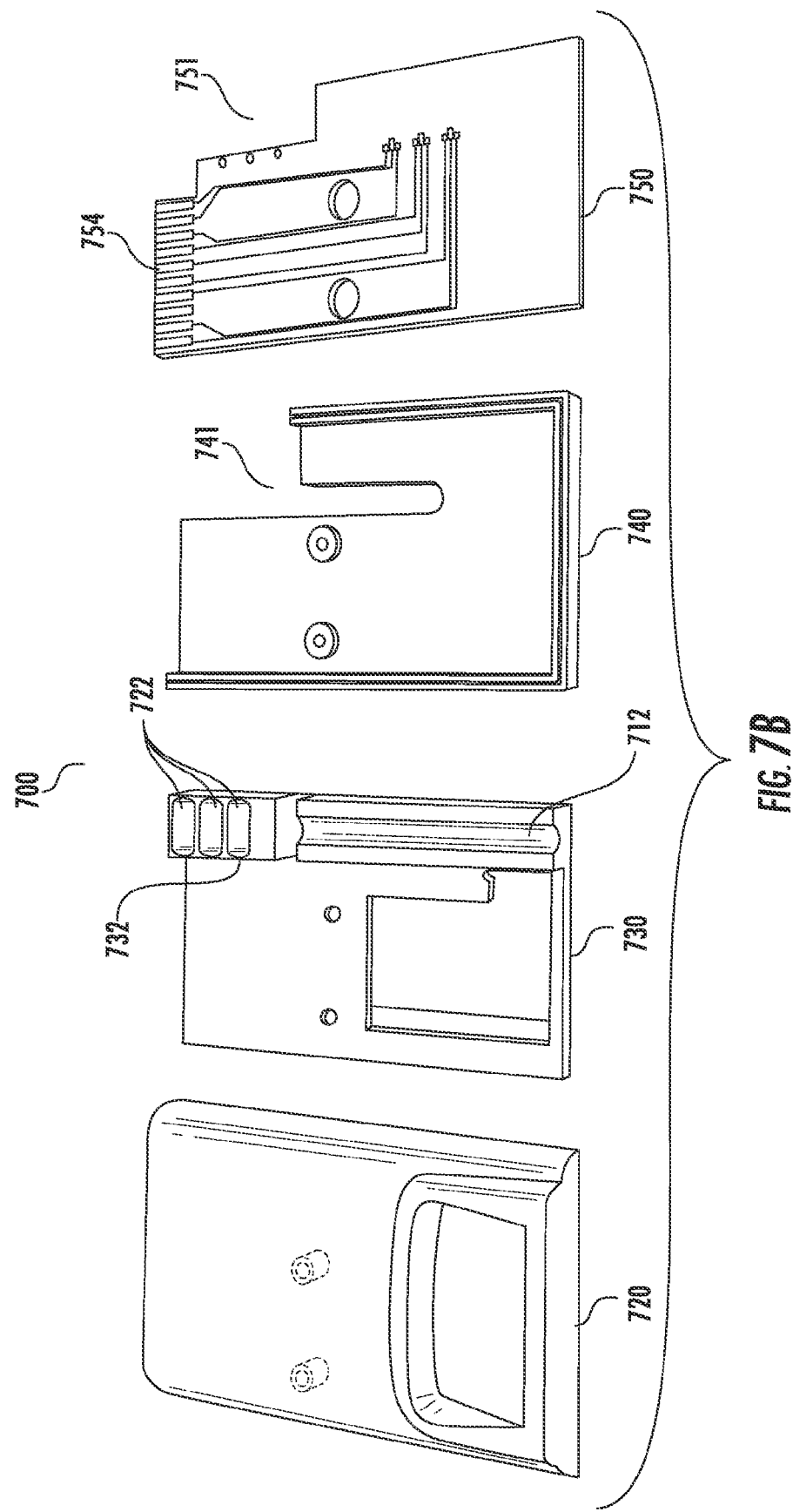

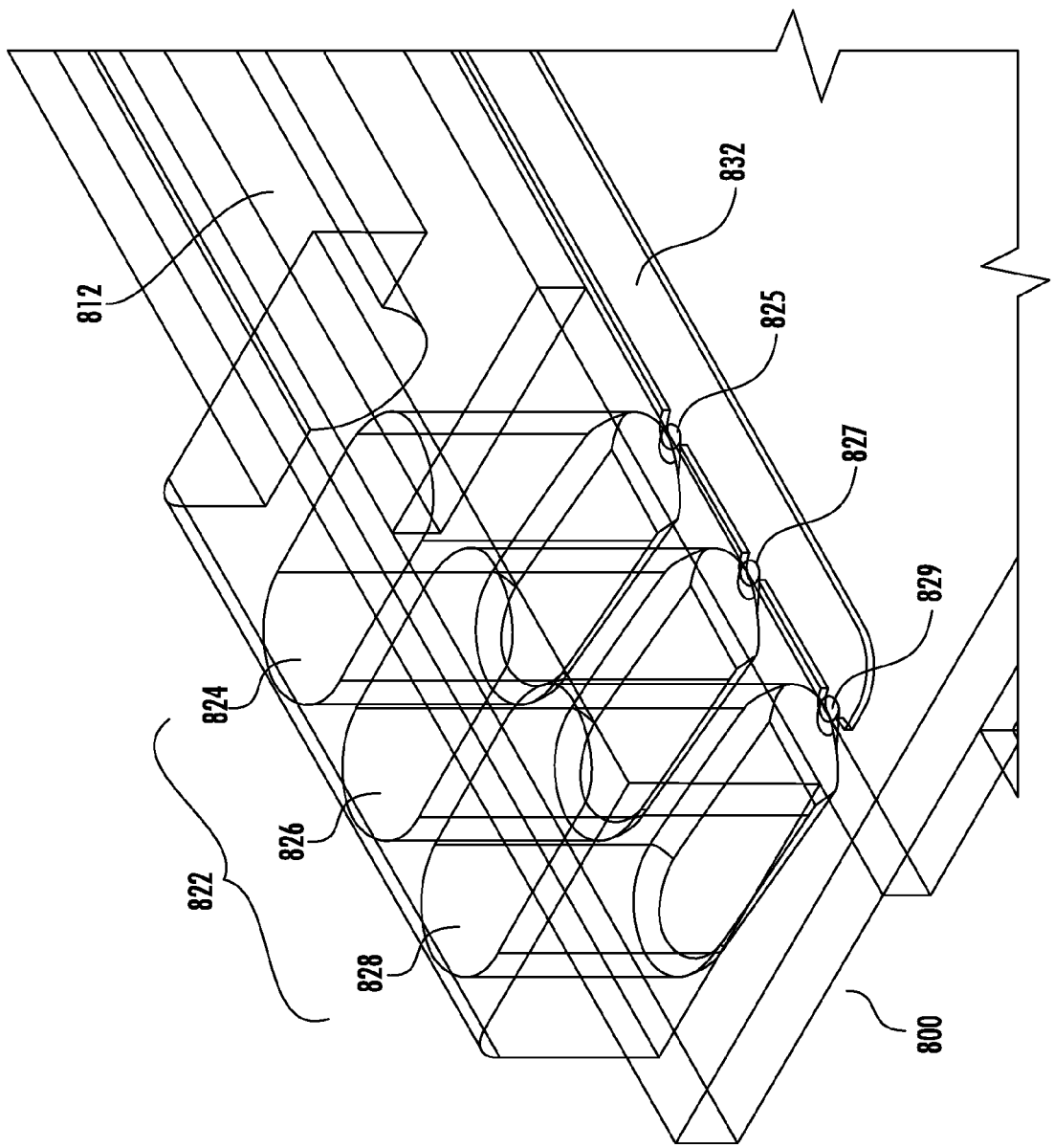

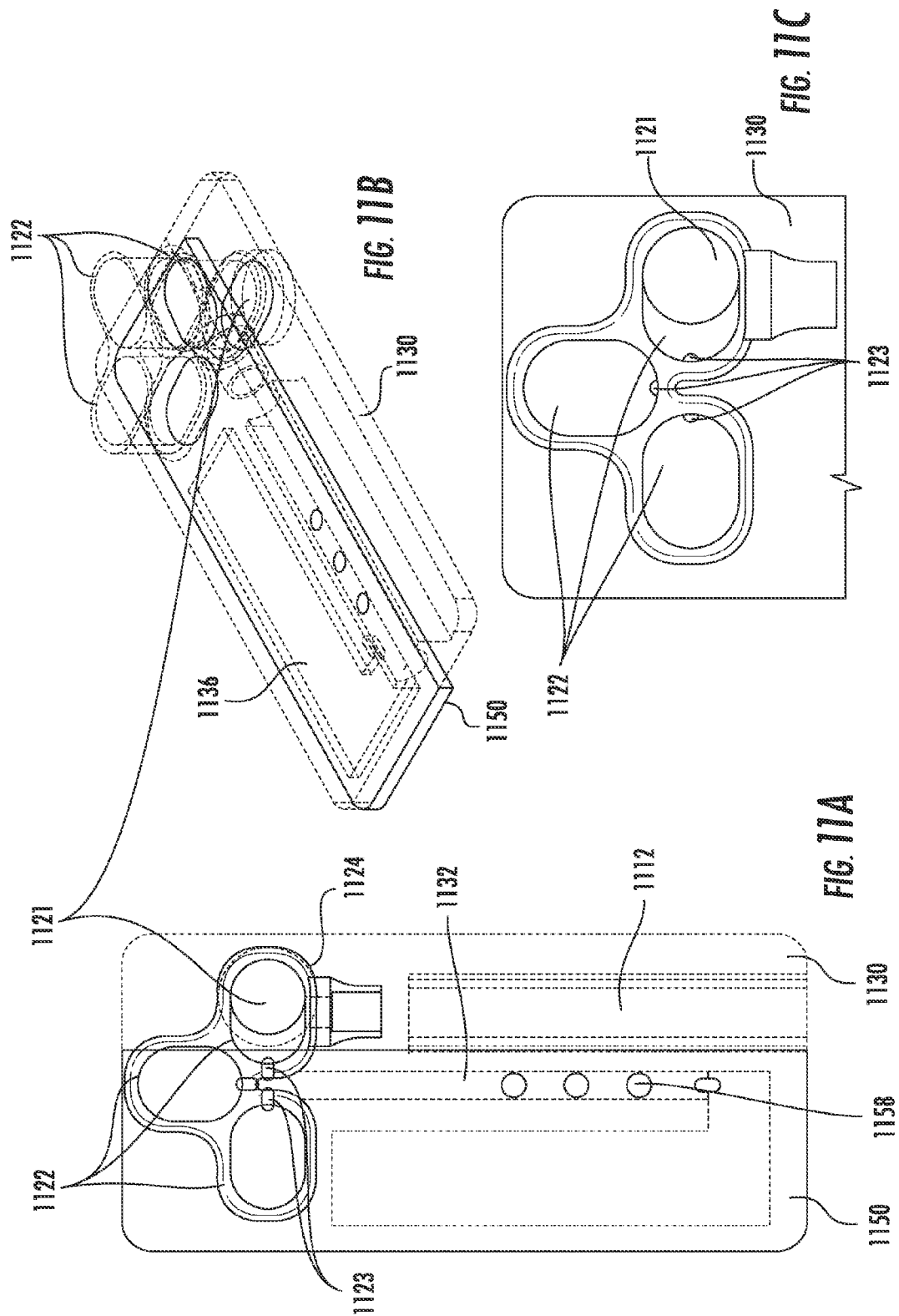

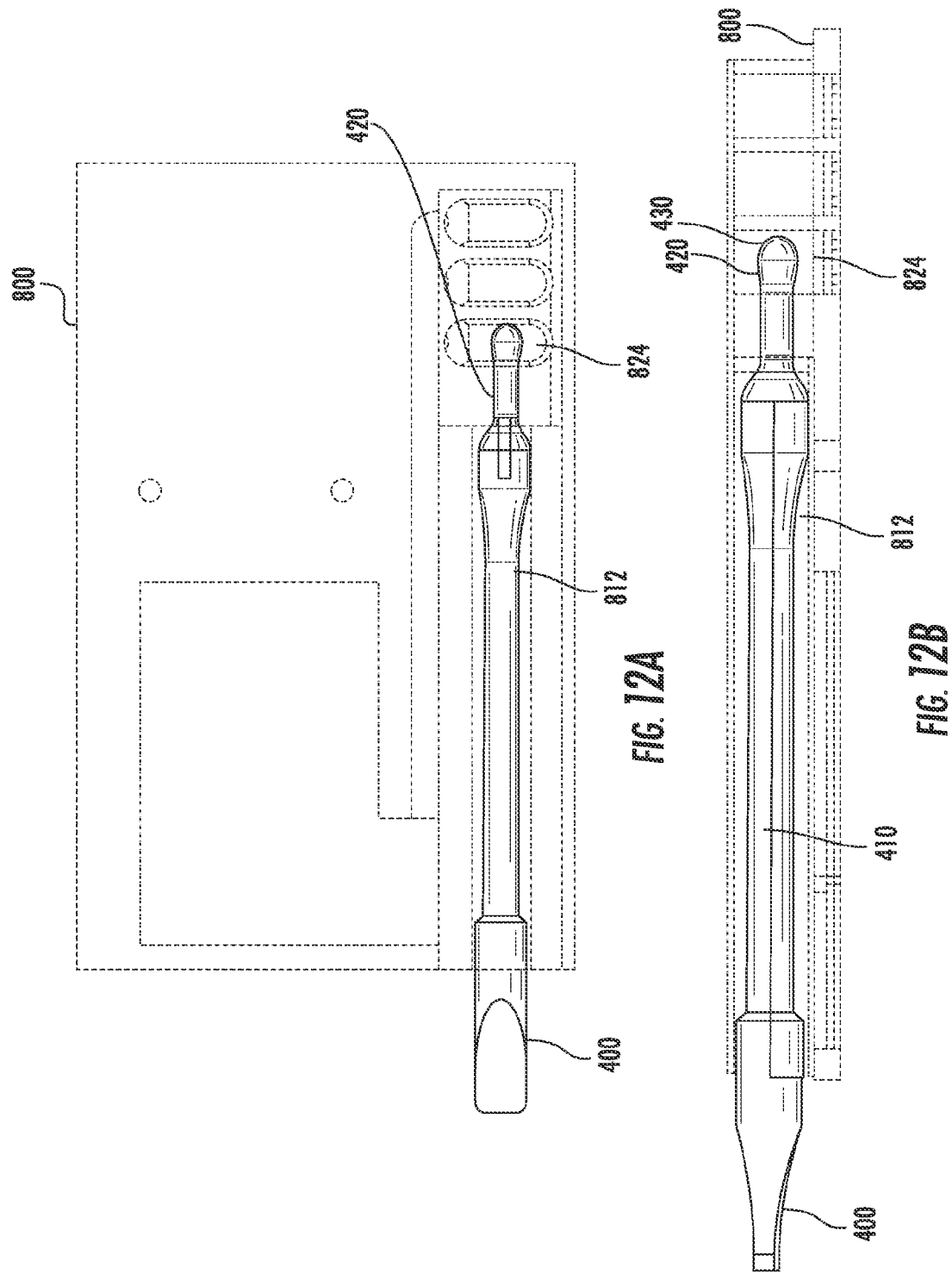

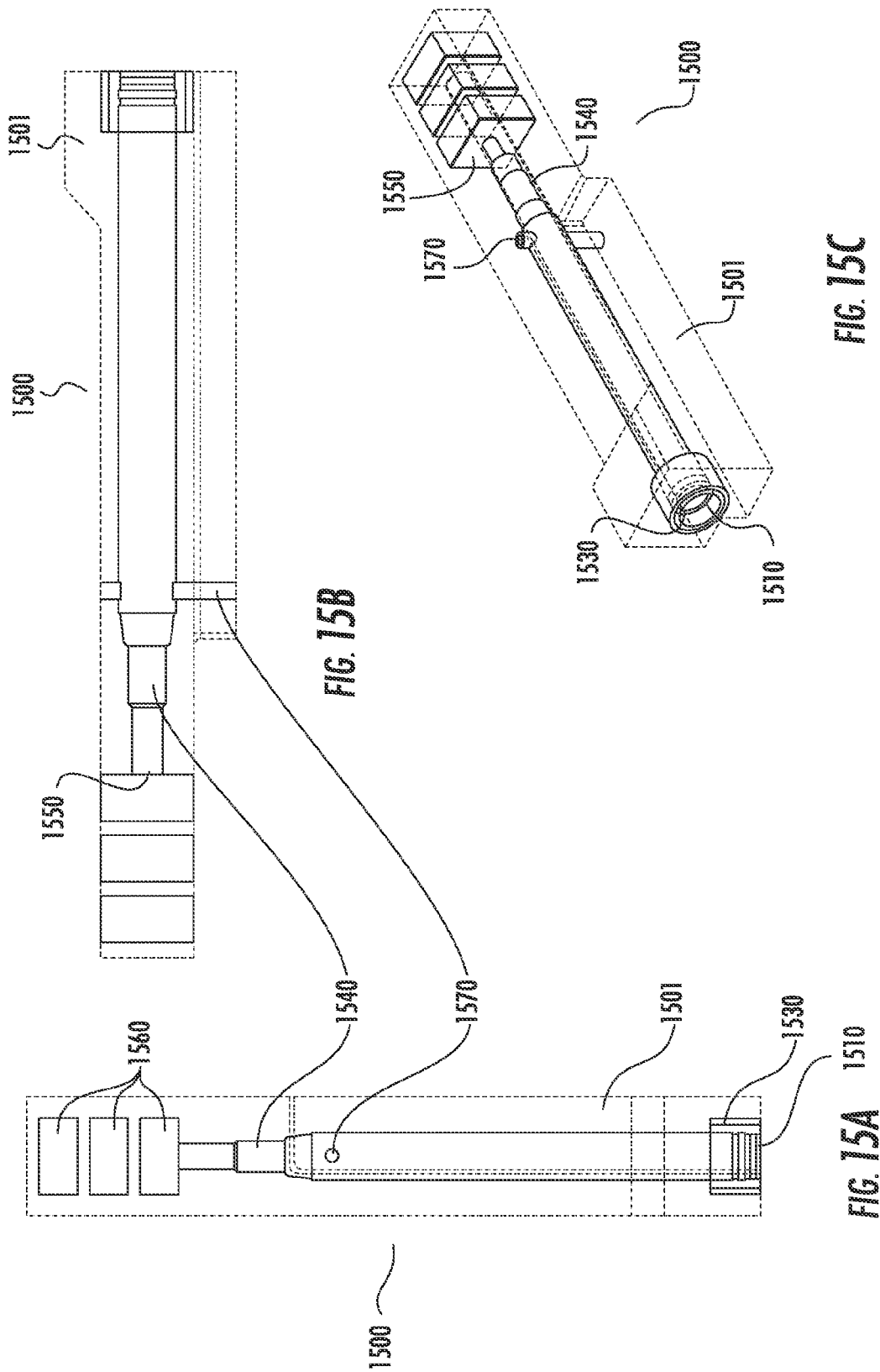

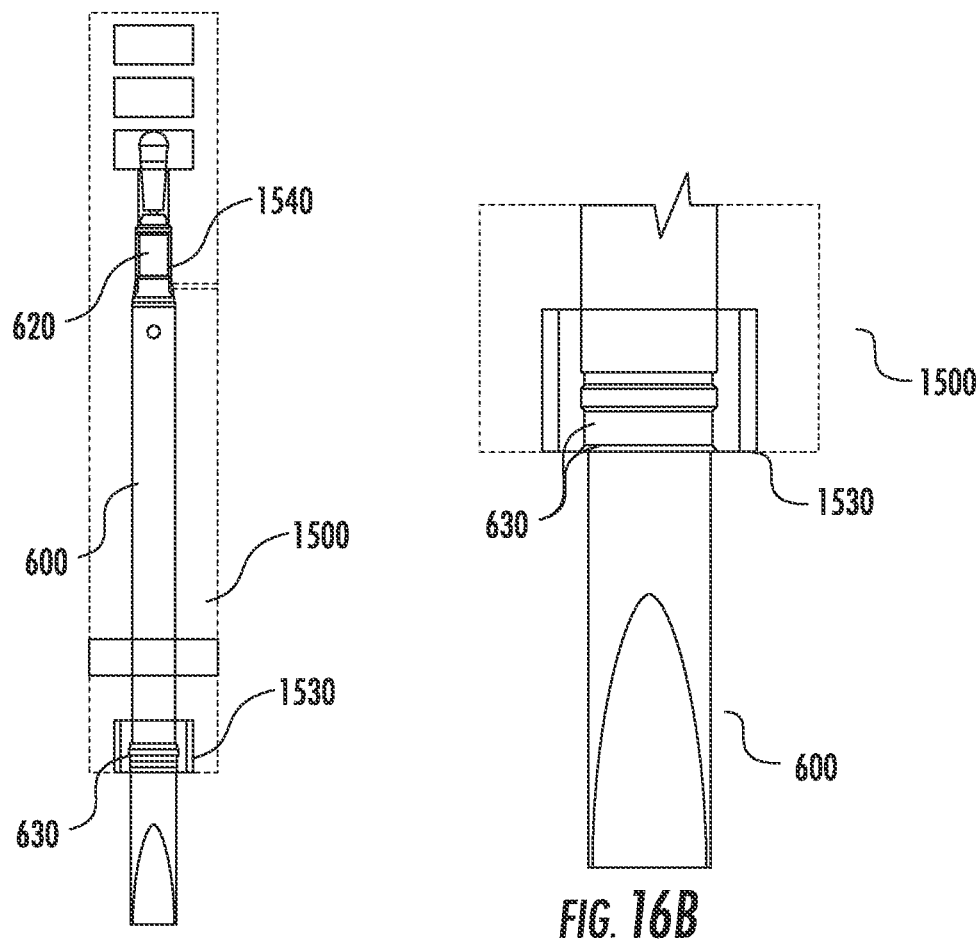
FIG. 16A
FIG. 16B
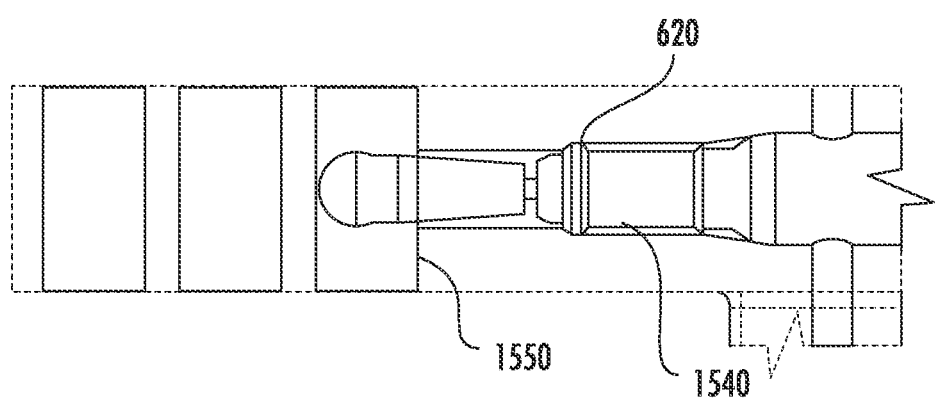
FIG. 16C

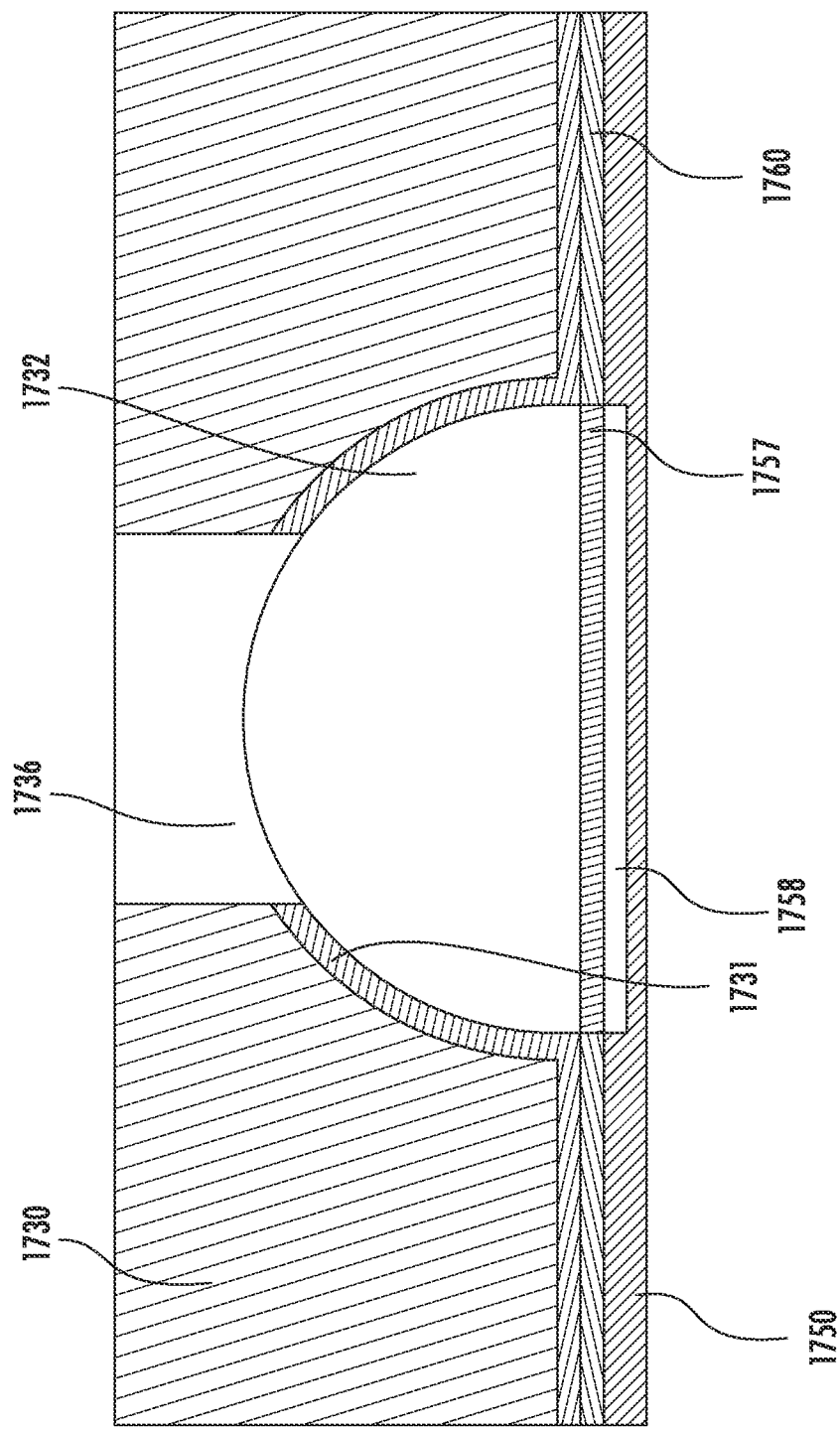

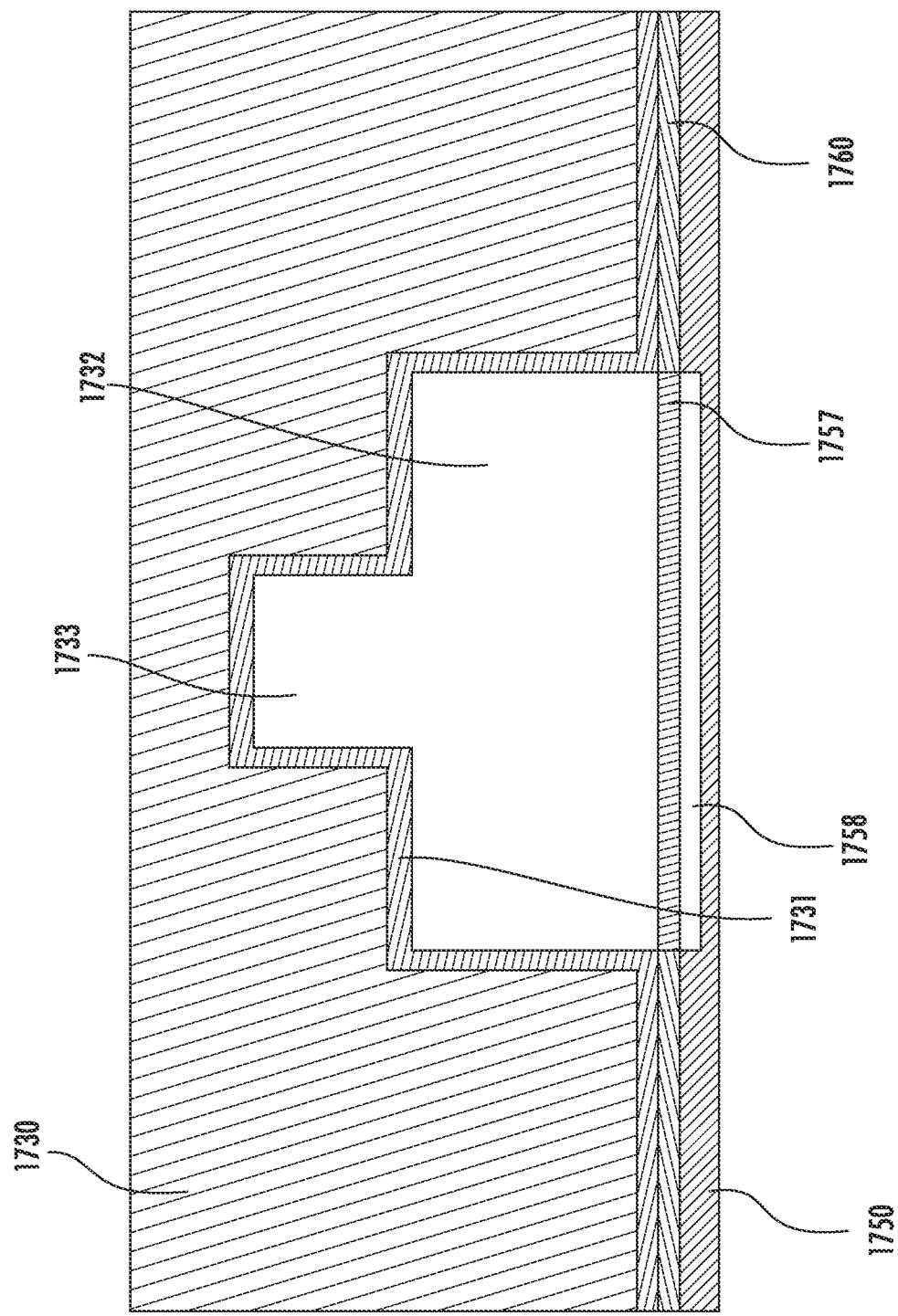

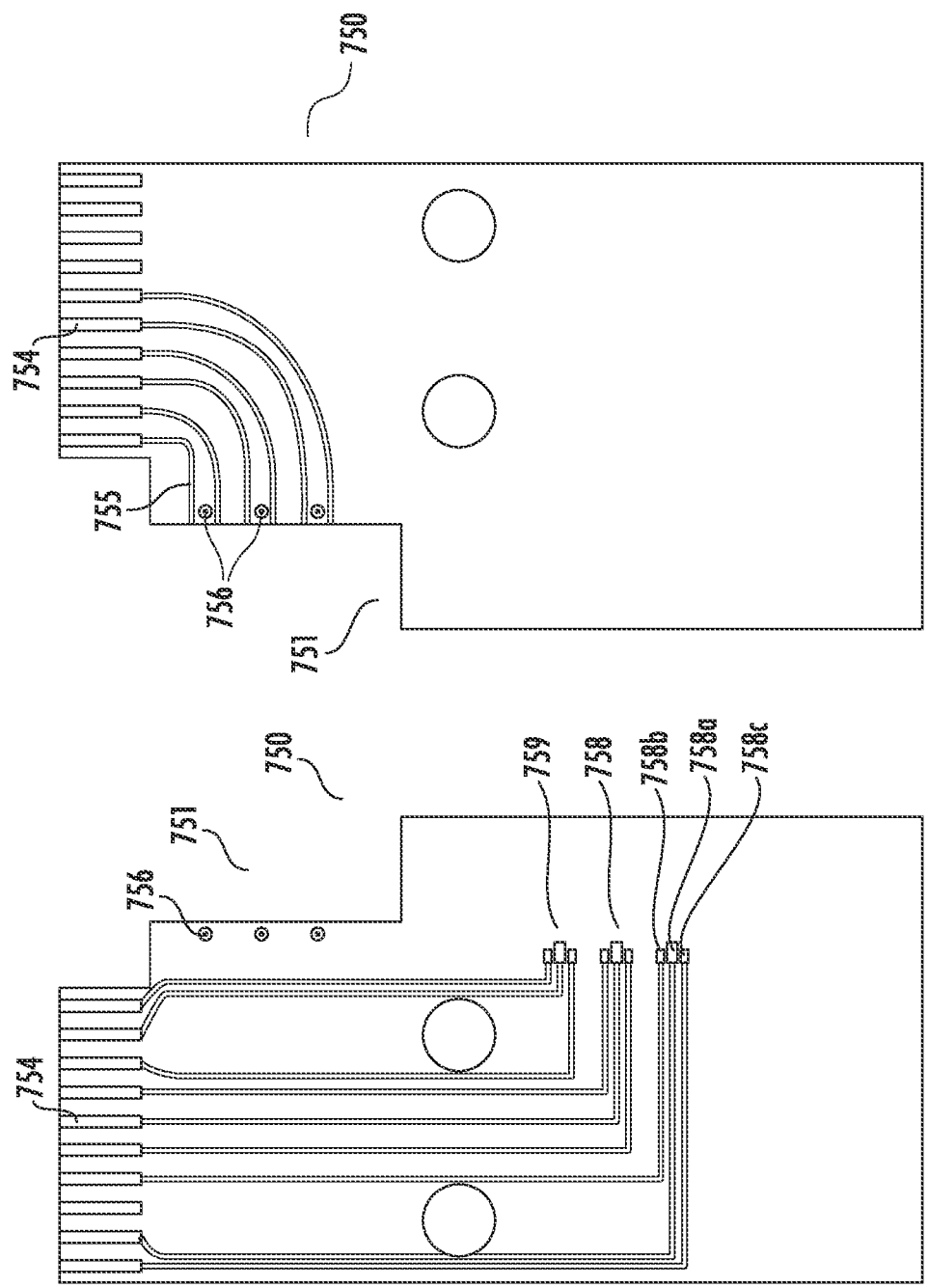

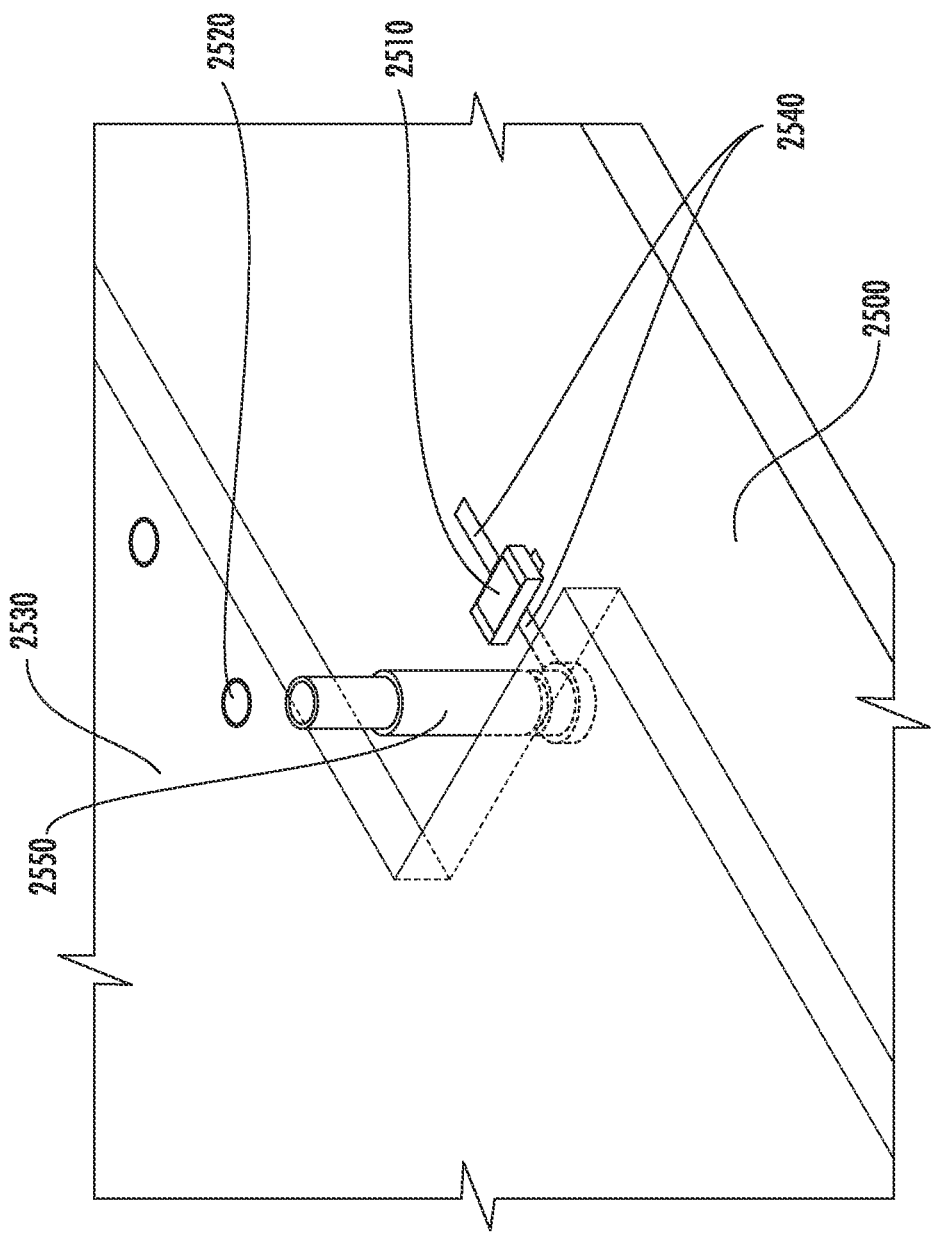

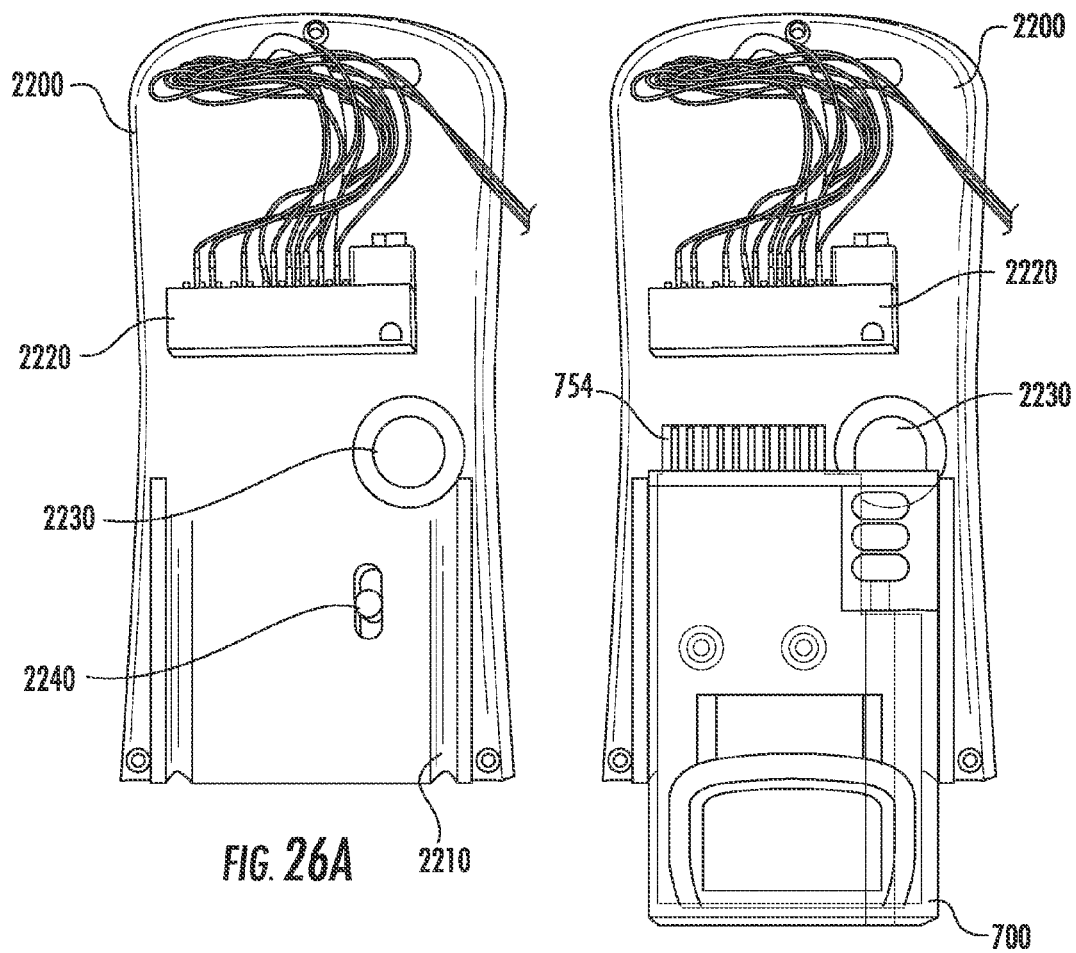
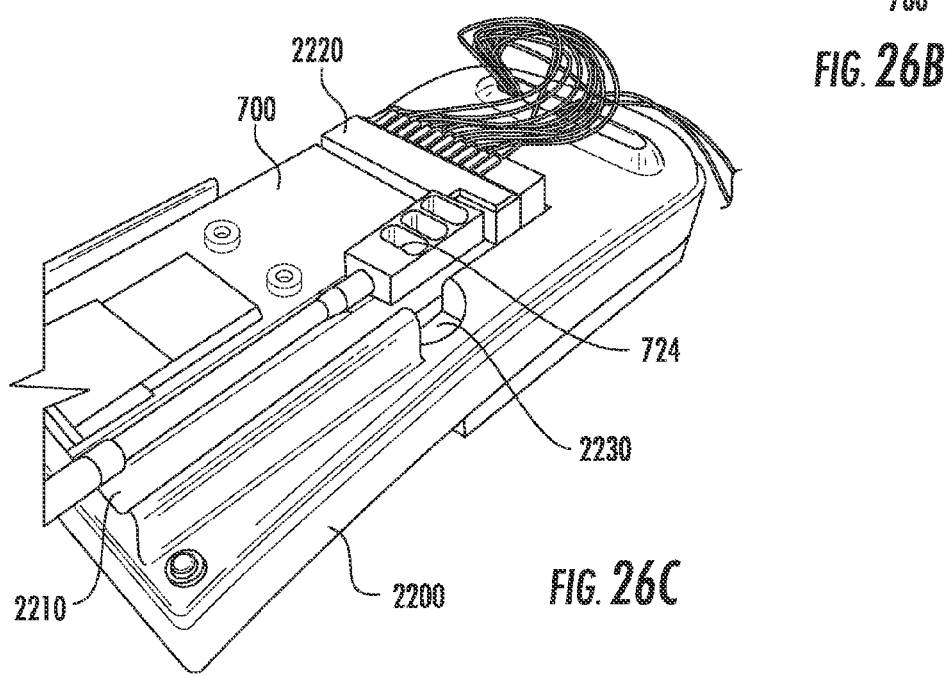

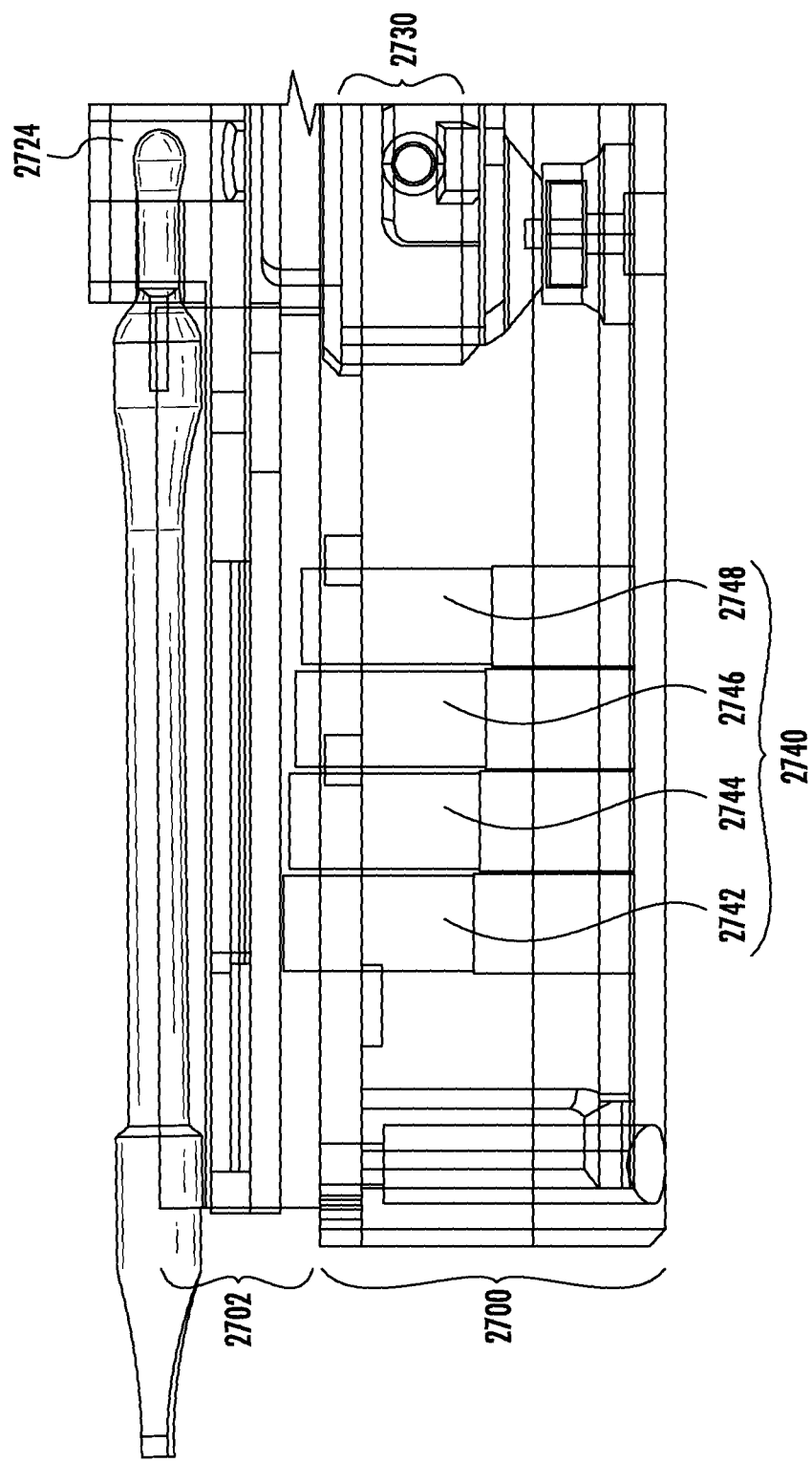

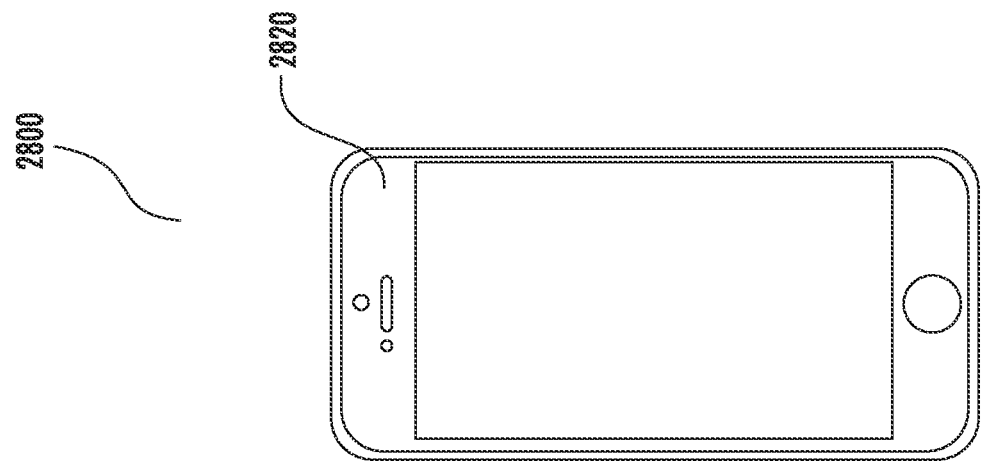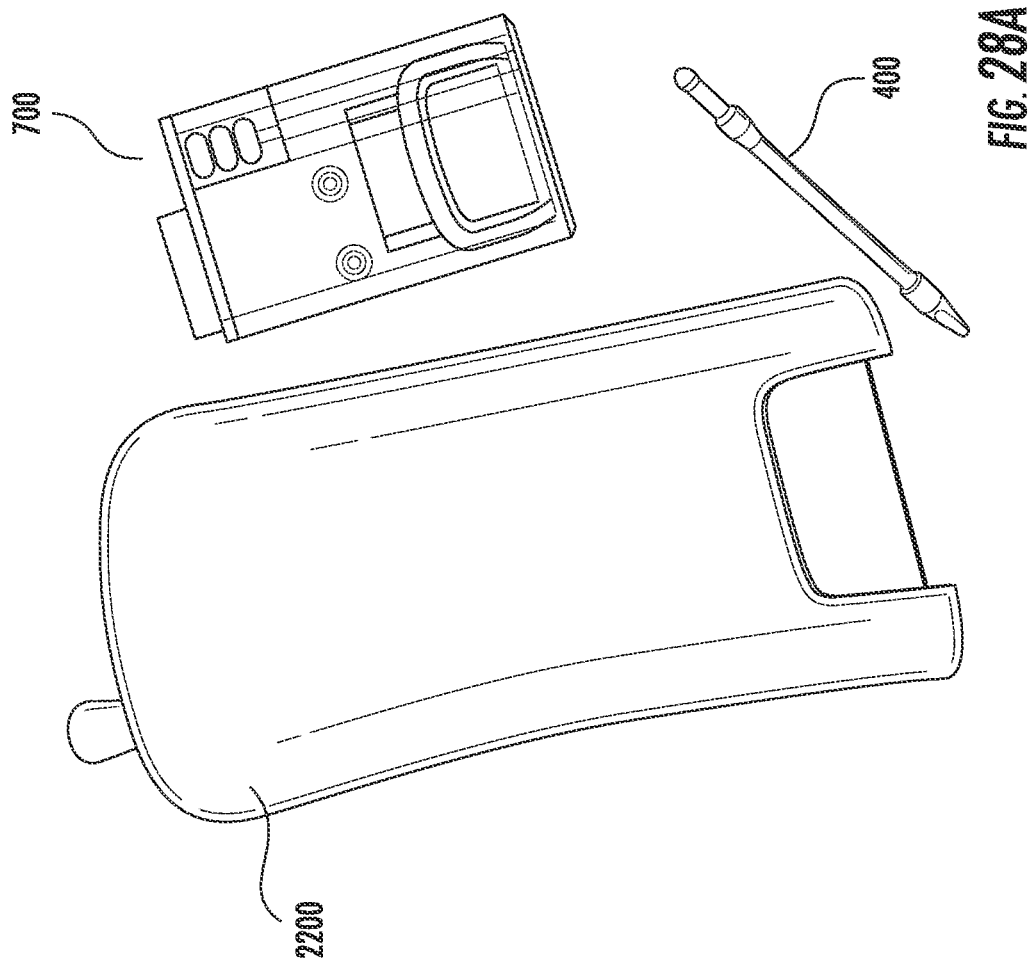
FIG. 28A

SYSTEMS AND METHODS FOR DETECTION AND QUANTIFICATION OF ANALYTES

CROSS-REFERENCE TO RELATED PATENT APPLICATIONS

This application is a continuation of International Application No. PCT/US2014/023821, filed Mar. 11, 2014, which claims priority under 35 U.S.C. §119(e) to U.S. Provisional Application No. 61/776,254, filed Mar. 11, 2013, the content of each of which is hereby incorporated by reference in its entirety.

FIELD OF THE INVENTION

The present technology relates generally to the field of molecule detection. In particular, the technology relates to microfluidic devices, systems, and methods for detecting the presence, absence and/or quantity of one or more particular analytes within a collected sample.

BACKGROUND

Conventional technologies for identifying the presence, absence and/or quantity of nucleic acids, proteins, and/or other molecules of interest within a sample often require expensive laboratory equipment and the expertise of highly-trained medical professionals. Consequently, such analyses are typically performed within laboratories or medical facilities. Such molecule detection can be important, for example, to detect the presence of pathogens, disease, contamination, overdoses, and poisonings within a person or other animal or within the environment. Unfortunately, today, individuals may face long waits before the proper tests can be performed and before the results can be generated and analyzed. Due to the long waits and the inconvenience of traveling to a laboratory or medical facility, illnesses and contaminations often spread and may cause substantial harm before the presence of said illness or contamination is even identified.

SUMMARY

There is a significant need for improved molecule detection and quantification technologies. There is a need for devices that can detect molecules of interest in less time and with less technical expertise than the conventional devices used today. There is a need for molecule detection technologies that can be utilized by consumers in non-clinical settings, for example, in schools, places of employment, and in the home. There is also a need for molecule detection technologies that can be used by consumers upon entering a pharmacy or healthcare facility, and which can generate results quickly so that results are available by the time the consumer talks with a pharmacist or healthcare practitioner. There is also a need for consumer-targeted molecule detection devices configured to minimize biohazard risks. Various embodiments disclosed herein may fulfill one or more of these needs.

One aspect of the disclosure is directed to a system for detecting molecules. In various embodiments, the system includes a cartridge device, a reader device removably coupled to the cartridge device, and a sample collection device. In some embodiments, the cartridge device includes: a cartridge housing having internal barriers defining a plurality of reservoirs, an analysis channel, and an input tunnel; and a circuit board coupled to or disposed within the cartridge housing, the circuit board forming a wall of the analysis channel and having a plurality of sensors disposed within a portion of the analysis channel. In some embodiments, the reader device includes: a magnet aligned with the sensor; a circuit electrically coupled to the sensor; and a processor having memory with instructions stored thereon. In such embodiments, the reader device also includes a reader housing in which the magnet, circuit, and processor are located, the reader housing defining a dock which receives at least a portion of the sample analysis cartridge. In some embodiments, the sample collection device is sized to fit at least partially within the input tunnel. Additionally, in some embodiments, the molecule detection system also includes a sonication component electrically coupled to the circuit and aligned with a first of the plurality of reservoirs. The sonication component may form a component of the cartridge device or the reader device and can be comprised partially or wholly of a piezoelectric transducer.

Another aspect of the disclosure is directed to a sample analysis cartridge. In some embodiments, the cartridge includes a housing and a circuit board disposed on, under, or within the housing. In some embodiments, the housing has internal barriers defining a plurality of reservoirs, an analysis channel, and an input tunnel. The plurality of reservoirs includes a first reservoir at least partially filled with a first liquid volume comprising sample preparation reagents and another reservoir at least partially filled with a liquid volume comprising a chemical substrate. In some embodiments, the plurality of reservoirs additionally includes a reservoir at least partially filled with a liquid volume comprising a wash solution, In certain embodiments, the input tunnel extends from an aperture at a surface of the housing to the first reservoir and each of the plurality of reservoirs is, at least at times, in fluid communication with the analysis channel. In certain embodiments, the circuit board includes a plurality of sensors aligned with a portion of the analysis channel.

In some such embodiments, the sample preparation reagents include a plurality of magnetic particles having surface-bound affinity molecules, a plurality of detector agents, and a plurality of agents to facilitate access to the target analyte and binding between the target analyte and the surface-bound affinity molecules and the detector agents. In other embodiments, the cartridge also includes a membrane disposed between the input tunnel and the first reservoir. The membrane of some such embodiments dry-stores a plurality of competitive binding agents, each competitive binding agent including a pre-bound target analyte bound to a signaling agent. Additionally, in such embodiments, the sample preparation reagents in the first reservoir include a plurality of magnetic particles having surface-bound affinity molecules and a plurality of agents to facilitate access to the target analyte and to facilitate binding of the surface-bound affinity molecules to the target analyte or the competitive binding agent. In various embodiments, the plurality of magnetic particles may include magnetic particles of two or more sizes, each size having a different surface-bound affinity molecule such that each size binds to a different target analyte.

In some embodiments of a sample analysis cartridge, the cartridge includes a plurality of valves corresponding with the plurality of reservoirs with one valve positioned at each intersection between one of the plurality of reservoirs and the analysis channel. In some such embodiments, each of the plurality of valves is phase-changeable upon the application of heat, and the circuit board includes a plurality of vias aligned with (e.g., disposed directly above or below) the plurality of valves; such vias are physically coupled to a heating element. In some embodiments, the sample analysis cartridge further includes an absorbant material disposed at a downstream end of the analysis channel.

In various embodiments of the cartridge, the housing includes a cover component, an internal component, and a base component coupled together to form a fixed structure. In some such embodiments, the cover component is disposed on a first side of the internal component, the base component is disposed on a second side of the internal component, and the circuit board is positioned between the internal component and the base component. Features of the cover component and the first side of the internal component may together define the input tunnel and the plurality of reservoirs, and features of the second side of the internal component and the circuit board may together define the analysis channel.

An additional aspect of the disclosure is directed to a sample analysis reader. In various embodiments, the reader includes a magnetic field generator, a circuit having a cartridge detection unit, a processor having memory with instructions stored thereon, and a housing with a dock for coupling to a sample analysis cartridge. In certain embodiments, when the sample analysis reader is coupled to the sample analysis cartridge, the magnetic field created by the magnetic field generator is substantially aligned with a sensor of the sample analysis cartridge, and the circuit is electrically coupled to the sensor of the sample analysis cartridge. In various embodiments, the sample analysis reader interchangeably couples to a plurality of sample analysis cartridges.

In some embodiments, the reader also includes a sonication component electrically coupled to the circuit. In such embodiments, when a sample analysis reader is coupled to the sample analysis cartridge, the sonication component is aligned with a sample preparation reservoir in the sample analysis cartridge.

In some embodiments of the sample analysis reader, the magnetic field generator includes a plurality of magnet field generators, and when the sample analysis reader is coupled to the sample analysis cartridge, the plurality of magnet field generators are aligned with a plurality of sensors lying on a plane of the sample analysis cartridge with each magnetic field generator configured to produce a magnetic field of a different strength. Such a configuration creates a magnetic field gradient within the analysis channel of the sample analysis cartridge. In some embodiments, the plurality of magnetic field generators are formed of a plurality of permanent magnets, each disposed at a different depth relative to the plane of the sensors. In other embodiments, the magnetic field gradient may be formed, for example, using a plurality of permanent magnets of increasing size or a plurality of inductors of increasing size or increasing numbers of coils.

In some embodiments of the reader, the sonication component is a piezoelectric component electrically coupled to the processor, and the piezoelectric component is positioned to transduce a mechanical event or mechanical change within the reservoir into an electrical signal. In such embodiments, a processor and/or circuitry electrically coupled to the piezoelectric component is configured to receive and interpret the electrical signal. This mechanical event in the reservoir can be transduced in the form of detected pressure applied to the piezoelectric component through flex in the sample preparation reservoir of the sample analysis cartridge upon entry of a sample collection device. Alternatively, a change in the mechanical load or mass above the piezoelectric component can cause a shift in the resonance frequency of the piezoelectric component that is detectable and/or quantifiable by the processor and/or circuitry. In other embodiments, the piezoelectric component and connected processor and/or circuitry quantify variation in the reflected wave of a pulse emitted from the piezoelectric component. In some such embodiments, the processor and/or circuitry is programmed with a threshold value for such variation in the reflected wave, the threshold set to distinguish between a state of having no collection device within the reservoir versus a collection device inserted state. In yet another example of the piezoelectric component transducing a mechanical event or mechanical change within the reservoir into an electrical signal, the piezoelectric component is configured to detect a sound wave such as the sound wave corresponding with a clicking that is actuated by mechanical parts of the sample collection device interacting with features of the input tunnel or reservoir.

In some embodiments of the sample analysis reader, the processor is configured to execute the instructions stored in memory, which when executed, cause the processor to perform a method. The method of certain embodiments includes identifying a proper test protocol for the coupled sample analysis cartridge based at least in part on cartridge identification information received from the circuit, and executing the proper test protocol. In some embodiments, executing the proper test protocol includes: stimulating the piezoelectric component to generate a test signal within the sample preparation reservoir and to detect a return signal, receiving detection signals from the piezoelectric component, the detection signals including the return signal and a resonance of the piezoelectric component, detecting entry of a sample collection device into the sample preparation reservoir based at least in part on a change in the return signal and/or a shift in the resonance of the piezoelectric component, and initiating a sonication protocol for the sonication component to mix reagents and sample particles within a liquid disposed within the sample preparation reservoir, wherein mixing facilitates hybridization of at least some of the reagents with the sample particles.

In some embodiments, the method performed by the processor when executing the proper test protocol additionally or alternatively includes receiving via the circuit, detection signals generated by the sensor of the sample analysis cartridge, and processing the detection signals. The method may also include transmitting data based at least in part on the detection signals to a mobile computing device or display device.

A further aspect of the disclosure is directed to a specialized computer for non-clinical disease detection. The specialized computer of various embodiments includes both hardware and software. For example, in some embodiments, the computer includes a dock or port for engaging at least a portion of a disease detection cartridge, the dock positioned on or within the computer. The computer of various embodiments also includes: circuitry for detecting signals generated from an oxidation reaction occurring within the disease detection cartridge, and a processor having memory with instructions stored thereon. Upon engagement with the disease detection cartridge, the processor executes the instructions, which in certain embodiments, causes the processor to perform a method that includes: detecting a classification of the disease detection cartridge from signals received from the circuitry, initiating a testing protocol specific to the classification, and generating disease detection results specific to the classification in less than thirty minutes. The method may further include transmitting the disease detection results to a remote computing device for further processing, display, and/or storage. In certain embodiments, the computer is less than 30 cm in height, less than 30 cm in width, and less than 30 cm in length. In certain embodiments, the computer is intended for use by non-trained consumers in home, office, or school settings.

One aspect of the disclosure is directed to a self-contained analyte detection kit, which securely stores, during and after analyte detection, all collected sample and all liquids needed to detect a specific analyte. In various embodiments, the kit includes a one-time-use sample collection device; and a one-time-use detection unit. The detection unit includes an input tunnel sized to securely and permanently receive the sample collection device, and a plurality of compartments, which separately and securely store reagents, a wash media, and a substrate. In some embodiments, the input tunnel extends from an aperture on a surface of the detection unit to an entryway of a first compartment holding the reagents. In some embodiments, prior to insertion of the sample collection device, a selectively breakable membrane covers the entryway of the first compartment to block flow of the reagents into the input tunnel. In some embodiments, complementary locking features are disposed on the sample collection device and in the input tunnel to restrict movement of the sample collection device relative to the detection unit upon insertion of the sample collection device into the input tunnel. Moreover, in some embodiments, the sample collection device and input tunnel are sized to form a liquid-tight seal as the sample collection device advances into the input tunnel.

Still a further aspect of the disclosed technology is directed to a method for detecting a disease without a healthcare provider or technician present. In some embodiments, such a method includes: rubbing an internal passage of a user's nose with a swab to collect a sample, placing a cartridge, which houses all reagents and substrates needed to perform a disease-detection testing protocol, into or onto a specialized computer configured to detect the cartridge, and inserting the swab into the cartridge such that the swab locks into place within the cartridge and cannot be removed. In various embodiments, the specialized computer senses the insertion of the swab and initiates a testing protocol. In some such embodiments, the specialized computer detects the presence or absence of a particular disease within the sample via the testing protocol in less than 30 minutes. The method may also include reading results of the test from a remote computing device, after the results are transmitted from the specialized computer to the remote computing device via a wired or wireless communication connection.

An additional aspect of the disclosure is directed to a method for detecting the presence, absence, and/or quantity of a target analyte within a sample. The method of various embodiments includes: loading a cartridge into or onto an analyte reader, wherein the cartridge has a plurality of reservoirs, including a first reservoir filled at least partially with reagents, a reservoir filled at least partially with a substrate, and optionally, another reservoir filled at least partially with a wash solution; removing a sample collection device from a sterile package; contacting a specimen with a tip of the sample collection device to collect a sample; and inserting the sample collection device into the cartridge until at least the tip enters the first reservoir. In certain embodiments, inserting the tip of the sample collection device into the first reservoir activates the analyte reader, causing a sonication device within the analyte reader to perform a sonication protocol to mix the sample collected by the sample collection device with the reagents in the first reservoir. Additionally or alternatively, inserting the tip into the first reservoir causes a series of heating elements to sequentially melt a series of valves positioned within or near the plurality of reservoirs, thereby sequentially releasing the contents of the plurality of reservoirs into an analysis zone for analysis by the analyte reader. In some such embodiments, inserting the tip of the sample collection device into the cartridge involves advancing the sample collection device into an input tunnel of the cartridge until: the tip of the sample collection device breaks a membrane barrier disposed at a distal end of the input tunnel, the tip enters the first reservoir, and the sample collection device locks into fixed engagement with the cartridge with a liquid-tight seal formed between the sample collection device and the input tunnel.

Another aspect of the disclosure is directed to computerized methods of detecting the presence, absence, and/or quantity of target analytes within a sample. For example, in some embodiments, a method performed by a computerized analyte reader includes: detecting the presence of a cartridge loaded into or onto the analyte reader, detecting identification information associated with the cartridge, and identifying a proper test protocol for the cartridge based at least in part on the identification information. In some embodiments, the computerized method additionally or alternatively includes: detecting a sample collection device inserted into a first reservoir of the cartridge, initiating a sonication protocol upon sample collection device insertion in order to mix a plurality of reagents, a plurality of magnetic particles, a plurality of detector agents or competitive binding agents, and a plurality sample particles within the first reservoir. In some such embodiments, the plurality of magnetic particles includes at least: a plurality of large magnetic particles each having a first surface affinity molecule on its surface configured to bind to a first target analyte, and a plurality of small magnetic particles each having a second surface affinity molecule on its surface configured to bind to a second target analyte. Upon mixing, for example, via the sonication protocol, if the first and/or the second target analyte is present, hybridization occurs. In some such embodiments, particularly embodiments with detector agents, the resulting mixture includes a plurality of sandwich complexes, each formed of a target analyte bound to both a surface affinity molecule on a surface of a magnetic particle and a detector agent. In other embodiments, particularly, embodiments with a competitive binding agent, the resulting mixture includes molecule complexes each formed of a target analyte bound only to a surface affinity molecule on a surface of a magnetic particle.

In some embodiments, the method also includes stimulating a first heating element such that a first valve within the cartridge melts and the mixture flows out of the sample preparation reservoir into an analysis channel. In various embodiments, the mixture is suspended in a solution, and the solution acts as a transport medium transporting the mixture from the first reservoir into the analysis channel towards a downstream absorbent material via capillary action. Within the analysis channel, the magnetic particles of the mixture localize over a plurality of magnets or other magnetic field generators within a portion of the analysis channel; the magnetic particles thereby form a plurality of localized samples. In such embodiments, the magnetic particles localize based on size and strength such that the large magnetic particles localize within a smaller upstream magnetic field and the small magnetic particles localize within a larger downstream magnetic field. The method of some embodiments also includes stimulating a second heating element such that a second valve within the cartridge melts and a wash solution flows out of a second reservoir into the analysis channel with the wash solution removing, from the plurality of localized samples, detector agents and/or competitive binding agents that are not indirectly bound to magnetic particles. The method of some embodiments further includes stimulating a third resistive heater such that a third valve within the cartridge melts and a solution of substrates flows out of a third reservoir into the analysis channel. In some embodiments, the detector agents and competitive binding agents include oxidizing enzymes which oxidize the substrate.

The computerized method may further include: detecting a first signal at a first recording sensor located within the smaller magnetic field, wherein at least a portion of the first signal is caused by the oxidation of the substrate; detecting a second signal at a second recording sensor located near the larger magnetic field, wherein at least a portion of the second signal is caused by the oxidation of the substrate; detecting a reference signal at a reference sensor; calculating a first resultant signal, for example, by subtracting the reference signal from the first signal to eliminate noise; processing and analyzing the first resultant signal to identify the presence and/or quantity of the first target analyte; calculating a second resultant signal, for example, by subtracting the reference signal from the second signal to eliminate noise; and processing and analyzing the second resultant signal to identify the presence and/or quantity of the second target analyte. In some embodiments, the method also includes transmitting signals indicative of a test result to a mobile computing device.

In some such embodiments, the first resultant signal is proportional to a quantity of the first target analyte present within the localized samples and the second resultant signal is proportional to a quantity of the second target analyte present within the localized samples. In other embodiments, the first and second resultant signals are indirectly proportional to a quantity of first and second target analytes present in the sample. In other embodiments, the first signal is indirectly proportional to the quantity of first analyte and the second signal is directly proportional to the quantity of second target analyte, or vice versa.

In other embodiments of a computerized method for detecting the presence, absence, and/or quantity of target analytes within a sample, the first reservoir only includes one size of magnetic particles and only one magnet or other magnetic field generator is provided in or near the analysis channel. In such embodiments, the method allows for the detection of the presence, absence, and/or quantity of a single target analyte.

In other embodiments of the computerized method, three or more sizes of magnetic particles are present in the first reservoir and an equal number of three or more magnetic field generators are provided in or near the analysis channel. In such a manner, a single device and single method may be employed to test for the presence of a plurality of analytes within a sample. Any number of particle sizes and magnetic field strengths can be utilized to create a 1-to-1 mapping between sensor signal and analyte target concentration whether that signal be directly or indirectly proportional to quantity of target analyte. In such embodiments, the number of magnetic fields is equal to the number of sensors and the number of unique magnetic particle populations, which are both equal to the number of different target analytes the system is configured to detect. Such methods and devices may be used, for example, to determine: from which illness, among many, a person is suffering; to which drug or poison, among many, a person is adversely reacting; or which chemical, among many, has contaminated the water. Other examples include quantifying the concentrations of various vitamins, hormones, proteins, or other analytes of interest within one's body.

BRIEF DESCRIPTION OF THE DRAWINGS

Exemplary embodiments are described below with reference to the accompanying drawings, wherein like numerals denote like elements. In the drawings:

FIGS. 1A-1D provide schematic depictions of molecules and reactions found within one embodiment of the presently disclosed analyte detection system.

FIGS. 3A and 3B depict a side view and perspective view, respectively, of one embodiment of a sample collection device.

FIGS. 3C and 3D depict a perspective view and side view, respectively, of the collection head provided in the sample collection device embodiment of FIGS. 3A and 3B.

FIG. 4A depicts a side view of another embodiment of a sample collection device.

FIG. 4B depicts a perspective view of the sample collection device of FIG. 4A.

FIG. 6 depicts a side view of another embodiment of a sample collection device.

FIG. 7B depicts a perspective view of components forming the cartridge device of FIG. 7A in a disassembled configuration.

FIG. 10B depicts a partial perspective view of the cartridge device from FIG. 8.

FIGS. 11A and 11B depict a top view and perspective view, respectively, of an internal component and a circuit board component found in one embodiment of a cartridge device.

FIG. 11C depicts a partial view of the internal component of FIG. 11A zoomed to highlight the features of the reservoirs in the particular embodiment.

FIGS. 12A and 12B depict a top view and a side view, respectively, of the cartridge device embodiment of FIG. 8 having the sample collection device embodiment of FIG. 4 disposed therein.

FIGS. 15A-15C depict a top view, side view, and perspective view, respectively, of another embodiment of an input tunnel.

FIG. 16A depicts a top view of one embodiment of an input tunnel wherein one embodiment of a sample collection device is disposed therein in a locked configuration.

FIGS. 16B and 16C depict partial views of the input tunnel and sample collection device of FIG. 16A zoomed to highlight the embodiment's locking features and sealing features, respectively.

FIGS. 17A-17I depict cross-sectional views of various embodiments of a microfluidic analysis channel.

FIGS. 18A and 18B depict a top view and a bottom view, respectively, of the circuit board component embodiment of the cartridge embodiment of FIGS. 7A and 7B.

FIG. 25 depicts a partial view of one embodiment of a reader device having a valve feedback system.

FIGS. 26A-26C depict various views of the reader device embodiment of FIG. 22 in various stages of engagement with the cartridge device embodiment of FIGS. 7A and 7B.

FIGS. 27A and 27B provide a side view and cross-sectional view of another embodiment of a reader device coupled to another embodiment of a cartridge device.

FIG. 28A depicts various components comprising one embodiment of a target analyte detection system.

DETAILED DESCRIPTION

Figure 2A:
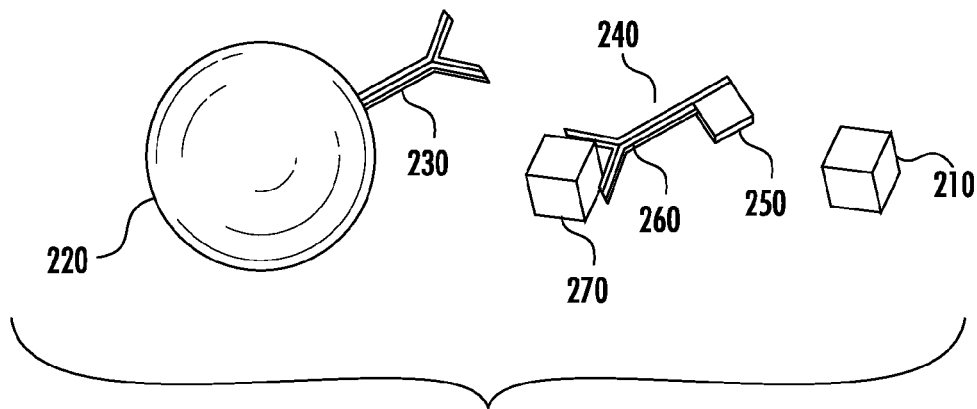
FIGS. 2A and 2B provide schematic depictions of molecules and reactions found within another embodiment of the presently disclosed analyte detection system.

In the following detailed description, reference is made to the accompanying drawings, which form part of the present disclosure. The embodiments described in the drawings and description are intended to be exemplary and not limiting. As used herein, the term "exemplary" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%, 1% or 0.1%.

As used in the specification and claims, the singular form "a", "an" and "the" include both singular and plural references unless the context clearly dictates otherwise. For example, the term "a molecule" may include, and is contemplated to include, a plurality of molecules. At times, the claims and disclosure may include terms such as "a plurality," "one or more," or "at least one;" however, the absence of such terms is not intended to mean, and should not be interpreted to mean, that a plurality is not conceived.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

Various devices, systems, kits, and methods disclosed herein are intended to isolate, tag, and detect a target analyte within a sample taken from a specimen. In certain embodiments, chemical reactions are employed to enable such detection. Exemplary chemical reactions are discussed below and depicted in FIGS. 1A-2B.

The Reactants and the Reactions

In some embodiments, a target analyte $110a$, $110b$ is added to a solution of sample preparation reagents, as shown in FIGS. 1A and 1B. This target analyte may be any molecule such as a nucleic acid, protein, small molecule, or heavy metal. The sample preparation reagents at least include magnetic microbeads or nanoparticles $120a$, $120b$ (referred to herein as "magnetic particles"). In various embodiments, each magnetic particle $120a$, $120b$ has an affinity molecule $130a$, $130b$ bound to its surface. The affinity molecule may be any suitable molecule or moiety that can bind to or capture a target molecule. Non-limiting examples of affinity molecules include antibodies (including single chain, multi-chain antibodies, diabodies, humanized antibodies, etc.), antibody fragments with affinity, ligands, polypeptide or protein molecules and moieties with binding affinity for substrates, nucleic acid molecules (e.g., aptamers), other molecules with binding affinity, and the like. FIGS. 1A and 1B depict an antibody $130a$ and a nucleic acid probe $130b$, although any suitable affinity molecule could be used, including a nucleic acid aptamer or other binding protein or molecule. In some embodiments, the sample preparation reagents also include a detector agent $140a$, $140b$, such as, for example, an antibody $160a$ conjugated to a signaling agent $150a$ or a labeled nucleic acid probe $160b$ bound to a signaling agent $150b$. The detector agents $140$ of various embodiments each include a signaling agent $150$, such as, for example, an oxidizing enzyme or other signaling enzyme, methylene blue or other electrochemically responsive tag, or a fluorescent tag such as ethidium bromide, fluorescein, green fluorescent protein, or other fluorophore.

In embodiments that include detector agents $140$, the various reagents listed above may hybridize together to form sandwich complexes. Exemplary sandwich complexes $100a$, $100b$ are illustrated in FIGS. 1C and 1D. Each sandwich complex is formed of: (1) a magnetic particle $120a$, $120b$ having a surface-bound affinity molecule $130a$, $130b$, (2) a target analyte $110a$, $110b$, and (3) a detector agent $140a$, $140b$. The exemplary sandwich complex $100a$ of FIG. 1C uses antibodies as affinity molecules, and the target analyte is a protein or small molecule of interest. The exemplary sandwich complex $100b$ of FIG. 1D uses nucleic acid probes designed to capture a particular sequence of nucleic acids.

In various embodiments, the signaling agent 150 is an oxidizing enzyme such as, for example, horseradish peroxidase (HRP) or soybean peroxidase. In such embodiments, the enzyme induces an oxidation reaction to occur at an electrochemical cell when in the presence of a particular chemical substrate. Thus, if the particular substrate flows over, or otherwise encounters, the oxidizing enzyme bound to a target analyte and magnetic particle at an electrochemical cell, an oxidation reaction occurs. In such embodiments, electrons are accordingly released from a working electrode of the electrochemical cell to replenish electrons stripped from the substrate by the oxidizing enzyme in a quantity proportional to the amount of target analyte present. The release or flow of electrons results in a current, which is detectable by an electrode, for example, as a change in current or a change in voltage.

Figure 2B:
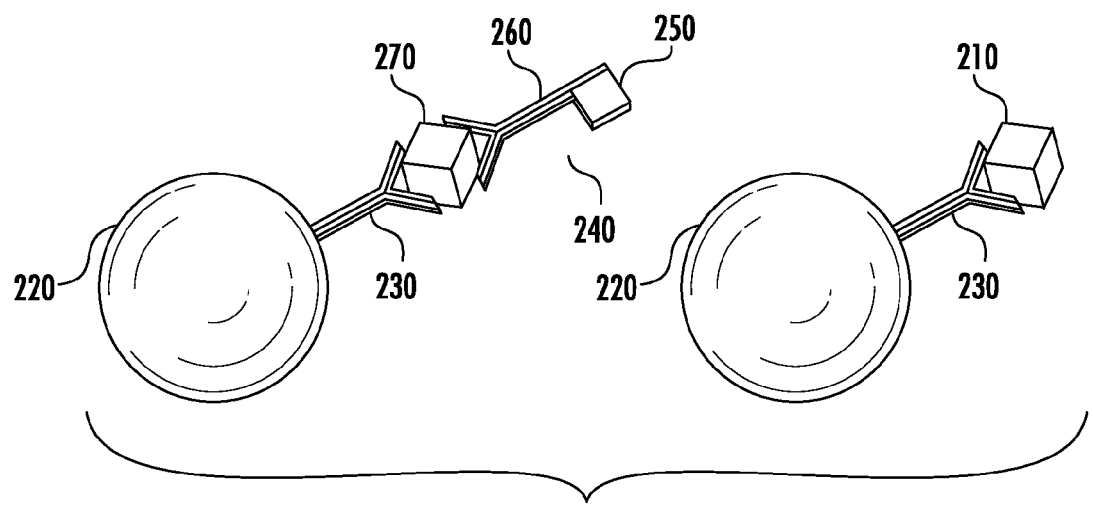

In other embodiments, such as the embodiment represented by the schematic diagrams of FIGS. 2A-2B, the sample preparation reagents at least include a population of magnetic particles 220, each having an affinity molecule 230 bound to its surface. In some such embodiments, a competitive binding agent 240 and a sample containing target analyte 210 are added to the sample preparation reagents. The competitive binding agent 240 of various embodiments includes a pre-bound target analyte 270, which comes pre-bound to a signaling agent 250, for example, any of the signaling agents described above. The pre-bound target analyte 270 may be indirectly bound to the signaling agent 250, for example, via an antibody, a nucleic acid probe, a nucleic acid aptamer, or other affinity molecule 260. In various embodiments, the unbound target analyte 210 from a sample and the competitive binding agent 240 compete with each other to bind to the affinity molecules 230 on the magnetic particles 220. The amount of competitive binding agent 240 and signaling agent 250 that successfully binds to the magnetic particles 220 is inversely proportional to the amount of unbound target analyte 210 present in a sample. In embodiments where the signaling agent 250 of the competitive binding agent 240 is an oxidizing enzyme, an oxidation reaction occurs if a particular substrate flows over, or otherwise encounters, the magnetic particles bound to the competitive binding agents 240 at an electrochemical cell. Electrons are accordingly released from a working electrode of the electrochemical cell to replenish electrons stripped from the substrate by the oxidizing enzyme in a quantity inversely proportional to the amount of target analyte present in the sample. The release or flow of electrons results in a current, which is detectable by an electrode, for example, as a change in current or a change in voltage.

In some embodiments contemplated herein, the sample reagents include only one population of magnetic particles and one population of detector agents or competitive binding agents. Such embodiments are tailored for detection of a single target analyte of interest.

In other embodiments, multiple populations of magnetic particles and detector agents and/or competitive binding agents are provided, each population constructed to have its own affinity. In such embodiments, each population of magnetic particles has a unique affinity molecule bound to its surface, and each population of magnetic particles is thereby designed to bind with a different target analyte. Similarly, each population of detector agents includes a unique affinity molecule and is thereby designed to bind with a different target analyte. In embodiments employing the competitive binding approach, each population of competitive binding agents includes a different pre-bound target analyte and is thereby designed to compete with a different target analyte. Such embodiments allow for the detection of a plurality of target analytes.

Those skilled in the art will appreciate that the possibilities for forming the magnetic particle-bound complexes are numerous and all such possibilities are contemplated herein. For example, the sample preparation reagents may include a biotin-labelled antibody, which binds to a portion of the target analyte. In some embodiments, antibodies and/or nucleic acids present among the sample preparation reagents may be pre-biotinylated such that a streptavidin conjugated signaling enzyme can bind with the biotinylated detector to form a complex. One such streptavidin conjugated signaling enzyme is HRP. The tagging combination is not limited to biotin-streptavidin. Any suitable tagging scheme will work. In another example, multiple HRP enzymes are conjugated together into a molecule commonly known as a Poly-HRP molecule in order to enhance the signal generating capability of the resultant sandwich complex.

In addition to the components that form the magnetic particle-bound complexes, the sample preparation reagents of various embodiments can include one or more of: (a) agents that facilitate formation of the magnetic particle-bound complexes, such as salts; (b) agents that facilitate access and specificity to target analytes, such as detergents and enzymes for lysis of bacteria or viruses or cutting of large molecules or nucleotides; (c) blocker proteins to decrease nonspecific binding; and (d) stabilizers such as, for example, trehalose, which can improve the shelf life of the sample preparation reagents.

In at least some embodiments of the sample preparation reagents, salts are necessary to enhance the likelihood of binding. For example, some embodiments include phosphate buffered saline (PBS). In other embodiments, any salt which does not interfere with electrochemical detection may be provided within the reagents.

Blocker proteins, such as the well-known Bovine Serum Albumin, casein, fibrinogen, or other blocker protein may be provided to help stabilize the antibodies, enzymes, and/or other proteins present among the sample preparation reagents. Such blocker proteins may also help prevent non-specific binding of signaling enzymes to the magnetic particles and to the walls of the systems and devices described elsewhere herein.

Additionally, for embodiments that require lysis to access the molecules or nucleic acids of interest, detergents may be employed. In various embodiments, nonionic detergents, rather than ionic detergents, are provided to prevent denaturation of the signaling enzyme and/or antibodies. Detergents can enhance lysis of bacteria, but are also useful for gently lysing various viruses, such as the influenza virus. Such lysing may be desirable to improve access to target analytes such as nucleoproteins internal to a virus. Additionally, in some embodiments, the sample preparation reagents include enzymes that enhance lysis and reduce viscosity during lysis; such reagents may be necessary for the preparation of some samples, for example, samples containing bacteria such as *E. coli*. The enzymes that enhance and facilitate lysis may include lysozymes and DNAses that chop up released genomic DNA without disrupting nucleic acid probes on the surface of the magnetic particles.

Enzymes such as RNAses or DNAses, which selectively chop larger nucleotide sequences into smaller sequences, can be useful for generating smaller fragments having favorable binding kinetics. Such enzymes are present in the sample preparation reagents of some embodiments. Other components may also be included within the sample preparation reagents. For example, a stabilizer agent such as trehalose, may be present; such stabilizer agents help protect proteins from oxidation and thereby increase the shelf-life of the reagents, especially at room temperature.

Various embodiments of systems described herein are designed to create a self-contained environment in which any of the chemical reactions described above can occur in an automated manner entirely or substantially without human intervention. For example, in some designs described herein, one or more of the above-described chemical reactions proceeds without any need for an operator to add or remove reagents from the system. In certain embodiments, the systems are closed such that biohazard risks, such as the risk of spilling sample collected from a specimen, are minimized. In various embodiments, such systems include at least, a sample collection device, a cartridge device, and a reader device. Some exemplary embodiments of such devices are described in detail below.

The Sample Collection Device

The sample collection device of various embodiments is configured to collect a sample from a specimen. Sample collection devices may be configured to collect cells and other biological material from any desired region or location, for example, an inner cheek, the throat, a nasal passageway, an ear, from urine, from blood, or from another body part. One exemplary sample collection device includes a unit that wicks a small droplet of blood or urine into a small capillary channel. In other embodiments, the sample collection device may be configured to collect biological material, particulates, or other chemicals from the environment, such as, for example, from the air or the water, or from a physical surface or other structure.

The sample collection device of various embodiments is sized and shaped to collect a sufficiently large sample from an appropriate location of a specimen such that it is possible, using the other devices described below, to detect the presence, absence, and/or quantity of a target analyte in the specimen. For example, for some target analytes, such as ones associated with the flu or cold viruses, the sample collection device may be a nose-insertion swab; the swab is sized and shaped to collect a sufficient amount of sample from a nasal passageway of an individual to enable detection of target analytes associated with the flu or cold virus, if present in the individual. For other target analytes, such as, for example, ones associated with strep throat, the sample collection device may be a throat swab shaped to scrape sufficient cells from an individual's throat. As another example, the sample collection device appropriate for collecting a target analyte associated with HIV may comprise a blood lancet. In another example, a sample collection device configured to collect urine may be appropriate for collecting target analytes for various tests, including, for example, tests for tracking testosterone levels, drug levels, vitamin levels, and/or fertility.

One such embodiment of sample collection device is provided in FIGS. 3A-3D. The sample collection device 300 is configured to collect a small quantity of urine from a specimen. The sample collection device 300 has a shaft 310, a collection head 320, a tip 330, and a collection area 340, the collection area 340 formed of a capillary tube. The shaft of some embodiments is elongated to facilitate easy and sanitary collection, with a collector's hand removed from the site of collection. The collection head 320 having a tip 330 is shown in isolation in FIGS. 3C and 3D. In some embodiments, the collection head 320 is combined with a shaft having one or more of the features described in more detail below, such as, for example, complementary threading or a locking mechanism and/or a sealing mechanism for engagement with a cartridge device.

Another embodiment of a sample collection device 400 is provided in FIGS. 4A and 4B. The provided sample collection device 400 is a nasal swab configured for collecting biological material from a nasal passage. The sample collection device 400 has a shaft 410, a collection head 420, and a tip 430. In some embodiments, the tip 430 is rounded; in other embodiments, any blunt or substantially blunt tip shape may be used. In various embodiments, the shaft 410 is elongated to fit within the nose of an individual and the collection head 420 is configured to gently scrap against an inner wall of the nose to collect fluid, cells, and other biological material present within the nose. In some embodiments, the shaft 410 and the collection head 420 are formed of the same material; in other embodiments, they are formed of different materials. In some embodiments, both the shaft 410 and the collection head 420 are formed of a plastic. In some embodiments, the sample collection device 400 is pre-packaged within sterile packaging and is configured for one-time use.

In some embodiments, the tip 430 of the sample collection device 400 is blunt and includes no sharp edges; the blunt design reduces the risk of users hurting themselves on the sample collection device. Additionally, advantages of a blunt tip 430 are explained in more detail below in the discussion of the cartridge device. The sample collection device 400 of various embodiments is configured for full or partial insertion into such a cartridge device.

Figure 5:
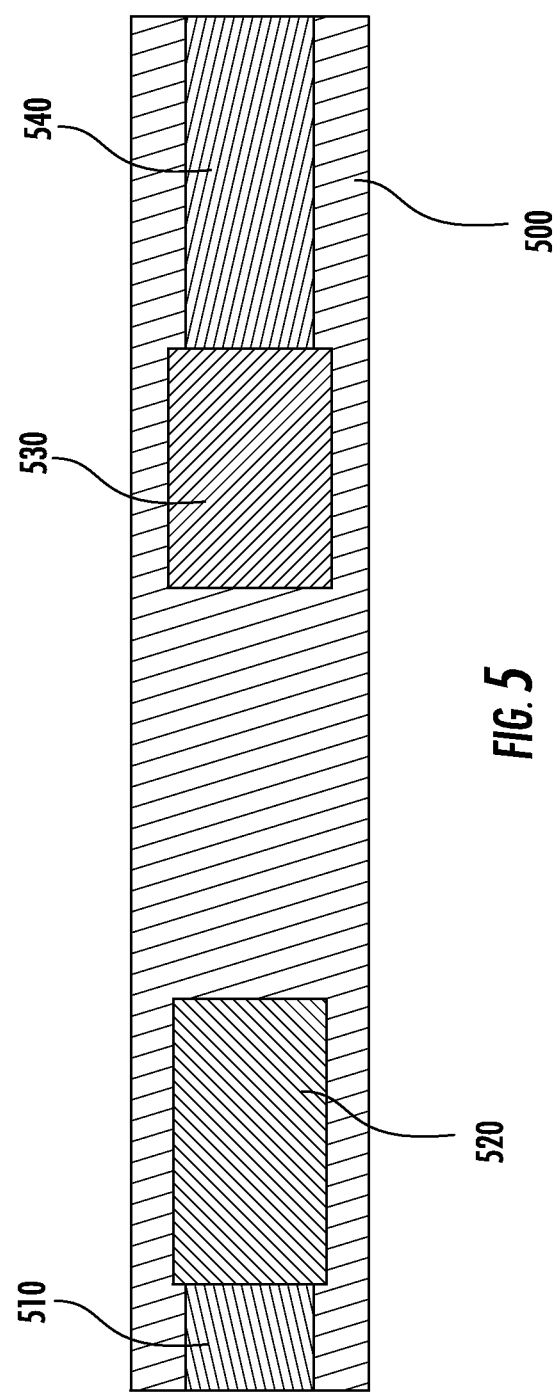
FIG. 5 depicts a functional block diagram of one embodiment of a sample collection device.

In various embodiments of the sample collection device, including sample collection device 400 of FIGS. 4A and 4B, the device includes a plurality of functional components. Such functional components are represented schematically in the block diagram of FIG. 5. As these components are described functionally, one skilled in the art will appreciate that the components may take many physical forms. All suitable physical forms are herein contemplated and incorporated. As depicted, in various embodiments, the sample collection device 500 includes one or more of: a collection zone 510 for collecting the sample and storing the sample for delivery to a reservoir within a cartridge device; a sealing zone 520 for facilitating the formation of a liquid-tight seal between the sample collection device 500 and a cartridge device upon insertion of the sample collection device 500 into the cartridge device, a locking zone 530 for facilitating a fixed engagement between the sample collection device 500 and the cartridge device such that upon insertion of the sample collection device 500 into the cartridge device, the collection device is mated irreversibly and immovably with the cartridge; and a handle zone 540 for the user to grasp and manipulate the sample collection device. In some embodiments, the collection zone 510 is also provided and configured to break a membrane within the cartridge device in order to obtain access into a reservoir within the cartridge device. In some embodiments, the handle zone 540 is breakable or otherwise removable from the remainder of the sample collection device 500 following insertion of said remainder of the sample collection device 500 into the cartridge device.

One embodiment of a sample collection device 600 with the functional zones prominently displayed is provided in FIG. 6. As shown, the sample collection device 600 includes a handle 640 for holding the device 600, a locking feature 630 for locking the device 600 into a cartridge, a sealing feature 620 for forming a liquid-tight seal with an internal tunnel in the cartridge, and a collection feature 610 for collecting and temporarily storing a sample.

The Cartridge Device

In various embodiments, a cartridge is formed of a housing, which defines an enclosed space and has various features that enable the cartridge to do one or more of the following: receive a sample with target analytes from a sample collection device, store the sample with sample preparation reagents, provide a space for mixing and hybridizing the target analytes with sample preparation reagents, provide an analysis zone wherein hybridized target analytes localize over sensors for detection, provide a liquid medium for transporting the hybridized target analytes to the analysis zone, store and provide a substrate that can undergo a detectable reaction when introduced to the hybridized target analytes, provide a liquid medium for transporting the substrate to the hybridized target analytes in the analysis zone, and provide a waste collection zone where waste is stored.

In various embodiments, the cartridge is a substantially closed system in which occur the reactions needed to detect the presence, absence, and/or quantity of target analytes. The cartridge of such embodiments is said to be "substantially closed" because the only inputs needed into the cartridge system are one or more of the following: a sample from a specimen, energy to facilitate mixing and hybridization, and a magnetic force to facilitate localization of hybridized target analytes within an analysis zone; the only outputs from the cartridge are electrical signals. In various embodiments, the cartridge is target-analyte-specific with the included sample preparation reagents selected to detect one or more specific target analytes. Different cartridge types include different reagents intended to identify different target analytes.

Figure 7A:
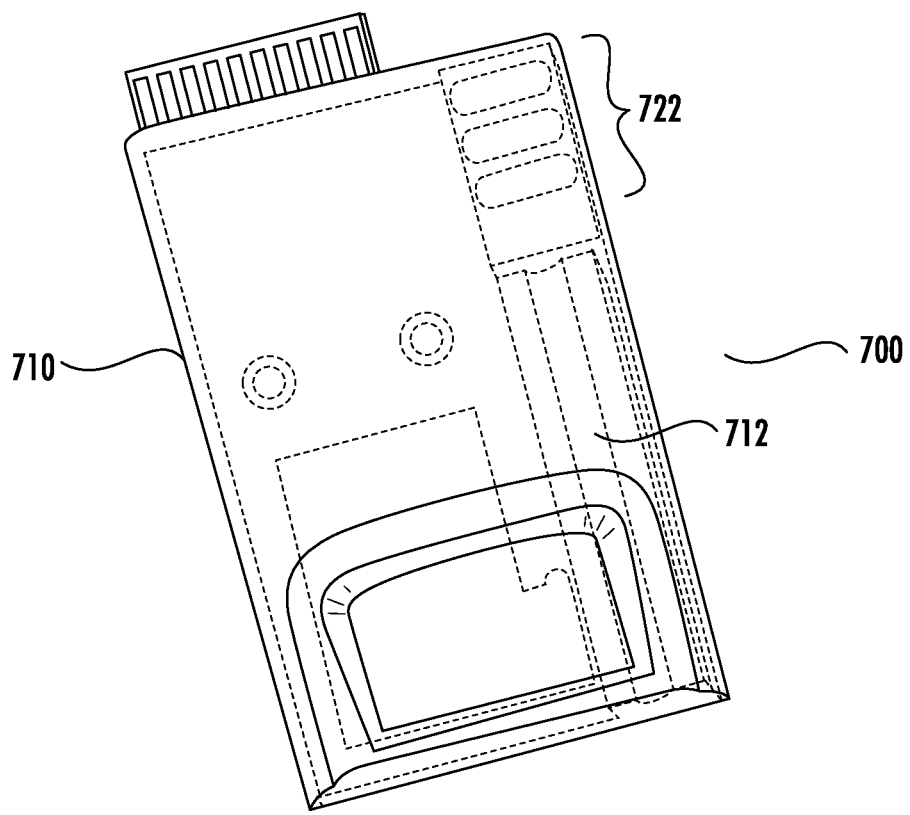
FIG. 7A depicts a perspective view of one embodiment of an assembled cartridge device.

One embodiment of a cartridge 700 is provided in FIGS. 7A and 7B. Specifically, FIG. 7A depicts various non-limiting examples of components of a cartridge 700 coupled together in a fixed configuration; FIG. 7B depicts the same components separated, prior to assembly, in order to highlight various features of the cartridge 700. As shown, the cartridge 700 of various embodiments includes a housing 710 formed of a cover component 720, an internal component 730, and a base component 740. Upon assembly, these components are coupled together to form a fixed structure having an input tunnel 712, a plurality of reservoirs 722, and an analysis channel 732. In some embodiments, these components are formed of a hard plastic or other substantially rigid material.

Figure 8:
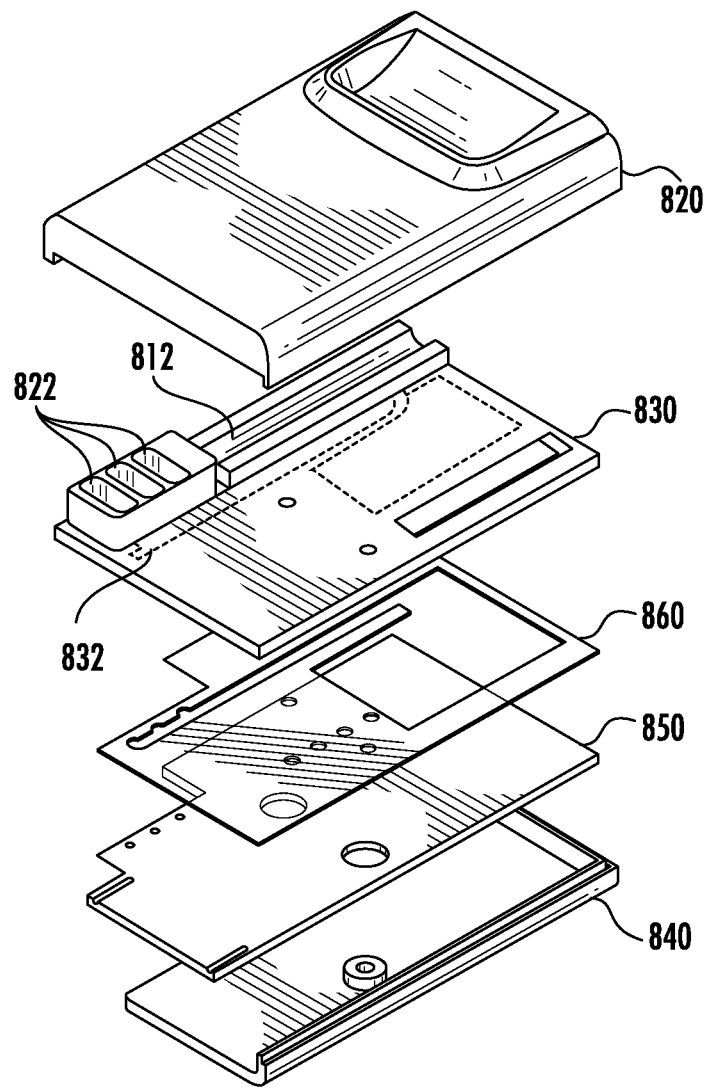
FIG. 8 depicts an exploded view of another embodiment of a cartridge device.

The various components of a similar cartridge embodiment and the orientation of the components relative to each other are also shown in the exploded view of FIG. 8. As shown, upon assembly of the depicted embodiment, the cover component 820 is disposed on a first side of the internal component 830, and the base component 840 is disposed on a second side of the internal component 830. A circuit board component 850 is positioned between the internal component 830 and the base component 840 and attached to the internal component 830, for example, with a layer of adhesive 860. Features of the cover component 820 and the first side of the internal component 830 together define an input tunnel 812 and a plurality of reservoirs 822, and features of the second side of the internal component 830 and the circuit board 850 define an analysis channel 832.

Figure 9A:
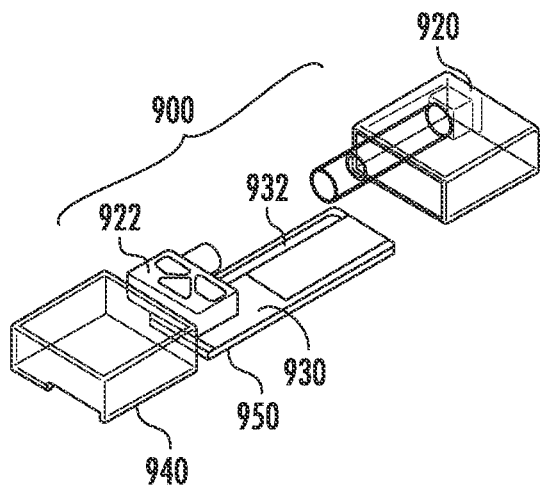
FIGS. 9A-9C depict exploded, semi-exploded, and non-exploded perspective views of another cartridge device embodiment.
Figure 9B:
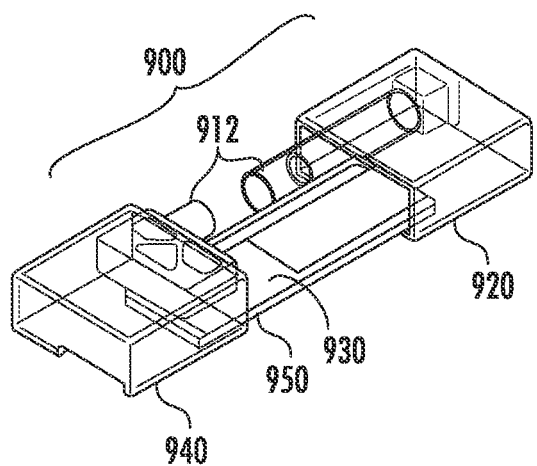
Figure 9C:
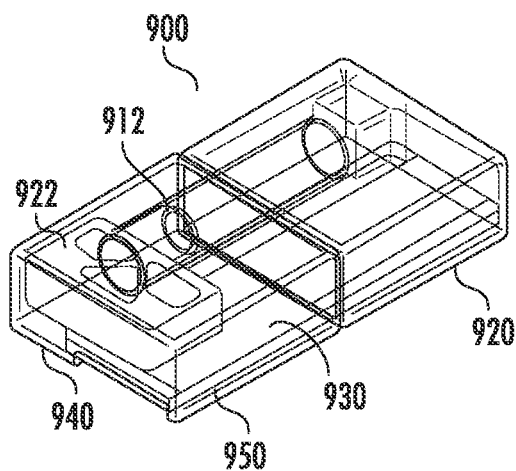

The various components of another cartridge embodiment and the assembly of such components are shown in the exploded, semi-exploded, and non-exploded perspective views of FIGS. 9A-9C, respectively. As shown, during assembly of the cartridge 900, the first cover component 920 is disposed laterally of the internal component 930, and the second cover component 940 is disposed on the opposite lateral side of the internal component 930. A circuit board component 950 is attached to the internal component 930, for example, to an underside of the internal component 930 using a layer of adhesive. In such embodiments, the internal component 930 and circuit board component 950 are positioned together between the first cover component 920 and the second cover component 940. Features of the first cover component 920 and the internal component 930 may together define an input tunnel 912, and features of the underside of the internal component 930 and the circuit board 950 may define an analysis channel 932. In some embodiments, the internal component 930 defines a plurality of reservoirs. In some such embodiments, each reservoir is a well that has been etched, carved, cut, or otherwise formed into a reservoir-defining portion 922 of the internal component 930. In some embodiments, the open side of each reservoir is covered by a gas-permeable/liquid-impermeable membrane.

Figure 10A:
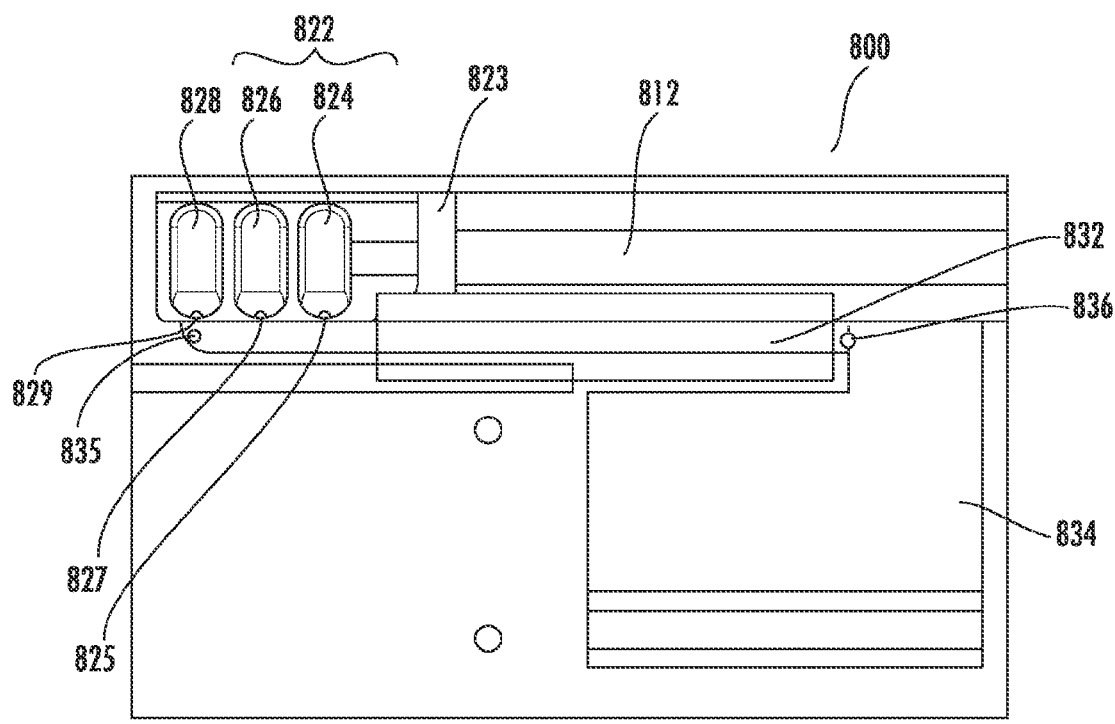
FIG. 10A depicts a top view of the cartridge device embodiment of FIG. 8.

Returning to the cartridge embodiment 800 of FIG. 8, various elements of the internal component 830 are also shown in the top view and partial perspective view of FIGS. 10A and 10B. In the depicted views, the input tunnel 812 leads to a first reservoir 824 in the cartridge 800. A second reservoir 828 and third reservoir 826 are also provided with the first reservoir 824. Each of the plurality of reservoirs 824, 826, 828 has a corresponding outlet near a bottom portion of the reservoir, which opens to the microfluidic analysis channel 832.

One skilled in the art will appreciate that while three reservoirs are depicted, in various embodiments, the plurality of reservoirs may include two reservoirs or four or more reservoirs and may adopt alternative spatial configurations. Any and all possible spatial configurations are contemplated and expressly incorporated herein. An example of another possible spatial configuration is provided in FIGS. 11A-11C. FIGS. 11A-11C depict the internal component 1130 and the circuit board component 1150 of a cartridge embodiment with the external housing components removed. In the depicted embodiment, the reservoirs 1122 are oriented in a cloverleaf fashion around an analysis channel 1132. As in other embodiments, the input tunnel 1112 extends from an aperture 1102 of the cartridge to a first reservoir 1124, and the analysis channel 1132 is defined by walls of the internal component 1130 and a wall of the circuit board component 1150. Additionally, each reservoir 1122 includes an outlet 1123, which connects the reservoir 1122 to the analysis channel 1132, and the analysis channel 1132 extends from the reservoirs 1122 to an absorbent pad 1136. In the depicted embodiment, sensors 1158 on the circuit board component 1150 are positioned within the analysis channel 1132. Additionally, in the depicted embodiment, a sonicator element 1121 is included, the sonicator element 1121 positioned to form all or a portion of the bottom surface of the first reservoir 1124.

In various embodiments of the cartridge device and sample collection device, such as, for example, in all embodiments described above, the input tunnel of the cartridge is configured to receive all or a portion of the sample collection device. One example is provided in FIGS. 11A and 11B, using the cartridge 800 of FIG. 8 and the sample collection device 400 of FIG. 4. As shown, the input tunnel 812 of the cartridge 800 is sized and shaped to receive all or a portion of the sample collection device 400. In certain embodiments, the input of a collected sample occurs by advancing all or a portion of the sample collection device 400 into the cartridge 800. For example, in FIGS. 11A and 11B, the sample collection device 400 is slid, tip 430 first, into the input tunnel 822. The sample collection device 400 is slid into the input tunnel 822 until all or a portion of the head 420 of the sample collection device 400 is disposed within the first reservoir 824.

In some embodiments, prior to insertion of the sample collection device 400 into the cartridge 800, an internal membrane is disposed within the input tunnel or between the input tunnel and the first reservoir. One embodiment of an internal membrane 823 is visible in FIG. 10A. While the internal membrane is most visible in FIG. 10A, it is contemplated that any and all of the cartridge embodiments provided herein may also include an internal membrane. As depicted, the internal membrane 823 covers, at least, the entirety of the cross-sectional area of the input tunnel 812, at or near the entryway to the first reservoir 824. The internal membrane 823 of some embodiments is double-walled and contains a volume of liquid between the two walls. The membrane liquid facilitates suspension of the sample from the sample collection device 400 and helps transport the sample particles into the first reservoir 824. In embodiments employing the competitive agent detection method described above, the internal membrane 823 also stores the competitive binding agents. In various embodiments, insertion of the sample collection device 400 into the input tunnel 812 ruptures the internal membrane 823, thereby releasing the stored liquid, any stored reagents, and the collected sample particles into the first reservoir 824. In other embodiments, as described below with reference to FIGS. 13A and 13B, the internal membrane 823 of cartridge 800 is a thin, single-walled membrane. In some such embodiments, one or more molecules are dry-stored within the membrane.

Figure 13A:
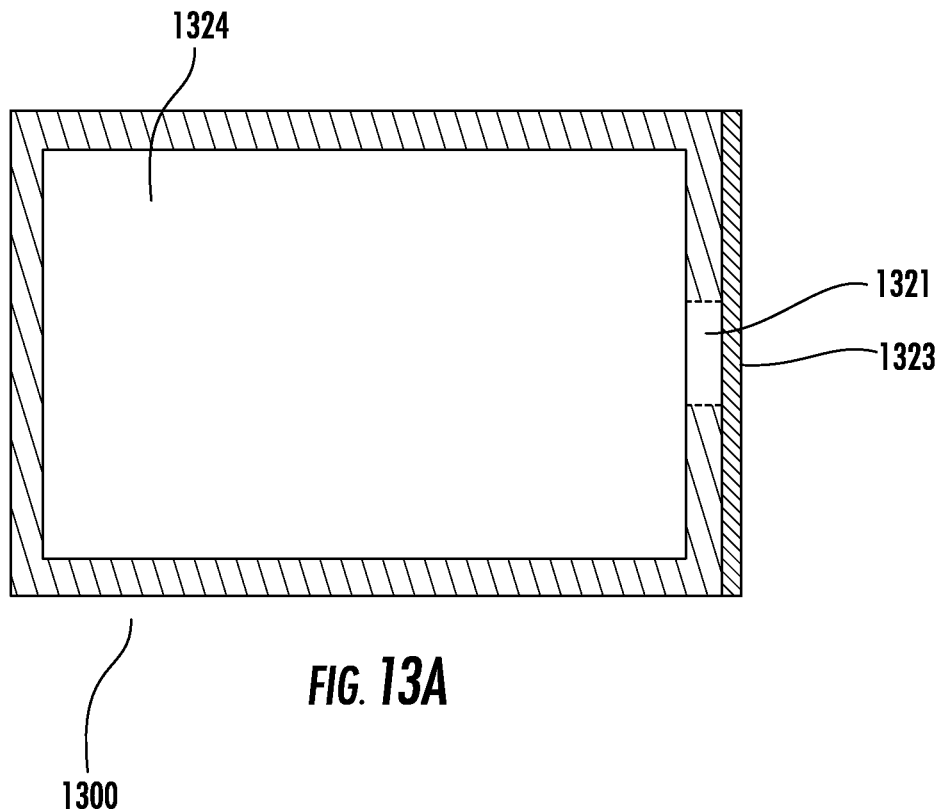
FIGS. 13A and 13B depict a top view and a perspective view of one embodiment of a sample preparation reservoir schematically represented in isolation from the remainder of a cartridge.
Figure 13B:
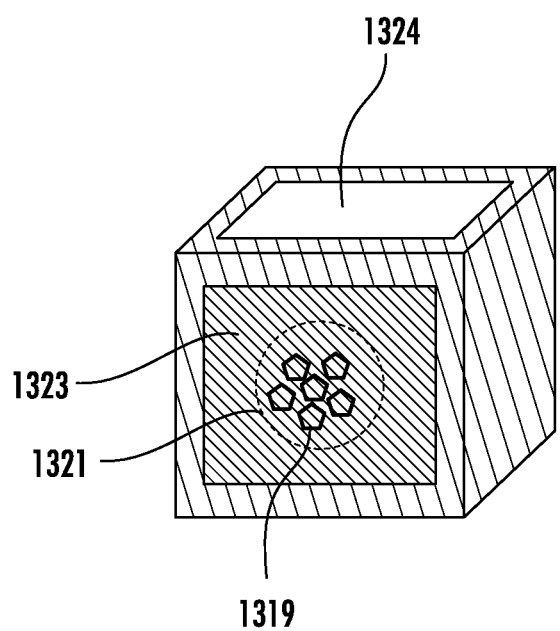

Another configuration for the internal membrane is provided in FIGS. 13A and 13B. FIGS. 13A and 13B schematically represent a top view and a perspective view of a first reservoir 1324 (similar to first reservoir 724 or 824) shown in isolation, removed from the remainder of the cartridge in order to highlight the placement of the internal membrane 1323. In the depicted embodiment, the internal membrane 1323 is disposed on an outer wall of the first reservoir 1324. Such a membrane 1323 would be within the input tunnel or within a space between the input tunnel and the first reservoir 1324. The internal membrane 1323 blocks entry to a sample input aperture 1321, thereby preventing liquid stored within the first reservoir 1324 from leaking out of the reservoir into, for example, the input tunnel. In some such embodiments, the internal membrane 1323 dry stores various molecules 1319, such as, for example, competitive binding agents or signaling agents as depicted in FIG. 1 as 150.

Figure 14:
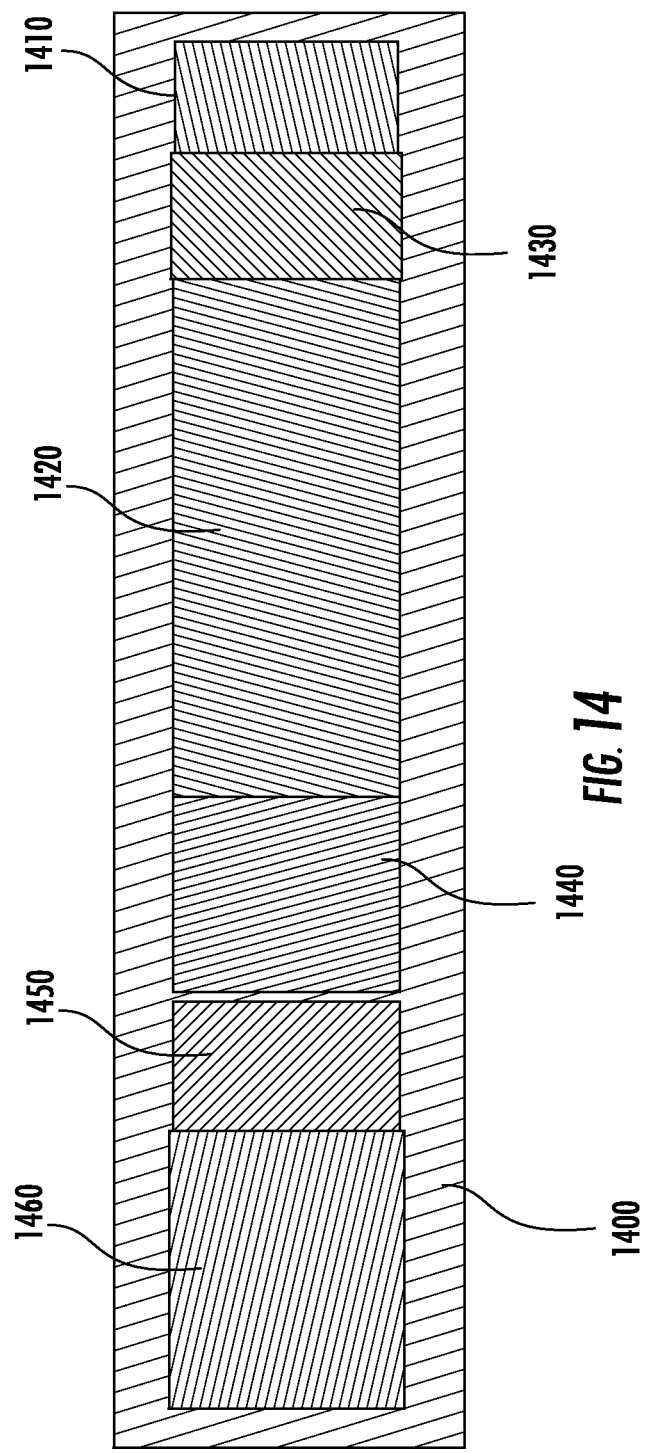
FIG. 14 depicts a functional block diagram of one embodiment of an input tunnel.

In various embodiments of the input tunnel, the tunnel includes a plurality of functional components that are complementary to functional zones and features of the sample collection device of various embodiments. Such functional components are represented schematically in the block diagram of FIG. 14. As these components are described functionally, one skilled in the art will appreciate that the components may take many physical forms. All suitable physical forms are herein contemplated and incorporated. As depicted, in various embodiments, the input tunnel 1400 includes one or more of: an entry port zone 1410 that provides an opening through which the sample collection device can enter the tunnel; a guidance zone 1420 for directing the collection device along an axis towards a first reservoir and restricting movement that is not along the axis; a locking zone 1430 with mechanical features to complement the locking zone on the sample collection device for achieving a secure, fixed coupling between the two devices; a sealing zone 1440 with mechanical features to complement the sealing zone on the sample collection device for achieving a liquid-tight seal between the two structures; and a membrane zone 1450 wherein a membrane is affixed to prevent leakage from the first reservoir. The first reservoir 1460 is also provided as it may form the distal end of the input tunnel 1400.

One embodiment of an input tunnel 1500 with the functional zones prominently displayed is provided in FIGS. 15A-15C. As shown, the input tunnel 1500 is defined, at least in part, by the internal component 1501. The input tunnel 1500 includes: an aperture 1510 through which the sample collection device can enter the tunnel 1500; an elongated portion 1520 for directing the collection device along an axis towards a first reservoir, the elongated portion 1520 having a diameter which restricts lateral movement of the sample collection device; a locking zone 1530 with mechanical features to complement and fixedly couple the sample collection device; a sealing zone 1540 with a narrowed diameter, a gasket, and/or or other mechanical feature to help achieve a liquid-tight seal between the internal tunnel 1500 and the sample collection device; and a membrane 1550. Also visible are a plurality of reservoirs 1560. A vent 1570 is also provided within the input tunnel 1500 to allow for the displacement of air that may otherwise create a pressure resisting the input of the collection device into the tunnel 1500.

As mentioned above, various embodiments of the cartridge include a membrane that prevents liquid from flowing out of the first reservoir and into the input tunnel prior to insertion of a sample collection device. In such embodiments, the sample collection device ruptures the internal membrane while advancing into the first reservoir. In certain embodiments, two events happen at, or substantially at, the instant the sample collection device pushes the membrane to its rupture point: (1) a flexible feature, such as for example, a rubber gasket or a gasket of any other suitable material, at the base of the collection head moves into position to form a liquid-tight seal with the structural housing features surrounding the membrane, and (2) the shaft of the sample collection device advances to a location where it locks in place within the input tunnel of the cartridge. The locking may be achieved, for example, by providing complementary grooves and ridges, grooves and teeth, or other complementary features between the shaft of the sample collection device and the surrounding input tunnel. By entering into a structurally engaged, fixed configuration within the input tunnel, the sample collection device of various embodiments is able to remain in place and resist pressure exerted on the collection head during rupture of the membrane. Additionally or alternatively, such a configuration enhances the convenient disposal of the cartridge after use by preventing users from accidentally opening the cartridge, thereby preventing exposure to the cartridge's potentially bio-hazardous components.

FIGS. 16A-16C depict one example of a sample collection device in a locked engagement within the input tunnel embodiment of FIGS. 15A-15C. In the depicted example, the sample collection device is the sample collection device 600 from FIG. 6. As shown in FIG. 16B, in the locked position, complementary features 630, 1530 on the shaft of the sample collection device 600 and the surrounding input tunnel 1500 engage, and as shown in FIG. 16C, in the locked position, the membrane 1550 has ruptured and a sealing mechanism 1540 on the collection device 1500 has formed a seal with a sealing portion 620 of the input tunnel 600. In the depicted embodiment, the sealing portion 1540 of the input tunnel 1500 includes a tunnel portion having a narrowed diameter and the sealing portion 620 of the collection device includes a gasket.

Returning to FIGS. 12A and 12B as another example, during insertion of the sample collective device 400 into the cartridge 800, the sample collection device 400 ruptures the internal membrane 823 while advancing into the first reservoir 824. In various embodiments, the tip 430 of the sample collection device 400 is blunt to ensure the internal membrane 823 deforms then ruptures at a controlled rupture point rather than being immediately pierced by the tip 430.

In order to obtain an internal membrane, such as, for example, internal membrane 823, having the desired rupture characteristics and desired rupture point, in various embodiments, the internal membrane is formed of a material carefully selected to have a desired modulus of elasticity, yield point, and/or rupture point. The modulus of elasticity is a constant that characterizes a material's degree of elasticity and can be used to determine the maximum the membrane can be stretched while still returning to its original shape. This point is called the yield point. Beyond the yield point, the material exhibits plasticity, undergoing irreversible deformation. Beyond the yield point is another critical point called the rupture point. The rupture point is when the membrane fails or breaks. The specific modulus of elasticity desired for an embodiment varies according to the size and shape of the sample collection device tip, which exerts pressure onto the internal membrane. The selected membrane material may include, for example: polyurethane, polysilicone and polybutadiene, nitrile, or other elastic material or composite thereof. Other suitable materials for the deformable membrane include, for example, parafilm, latex, foil, and polyethylene terephthalate.

In various embodiments, the size of the collection head 420, the shape of the tip 430, the rupture point of the internal membrane material, and the location of the complementary locking features are selected in consideration of each other.

In one embodiment, the complementary locking features include positive grooves (i.e., ridges or other protrusions) radially placed in the input tunnel and negative grooves or other complementary depressions radially placed on the shaft of the sample collection device. The radial placement allows for insertion of the sample collection device 400 into the input tunnel 812 regardless of the radial orientation of the sample collection device 400. In other embodiments, one or a plurality of non-radial complementary engagement features may be provided. In some embodiments, the engagement features are constructed such that, when the engagement features of the shaft 410 move against the engagement features of the input tunnel 812, one or both of the engagement features are reversibly compressed or retracted, returning to their initial positions when the shaft 410 enters the location of fixed engagement. Such a structure prevents any further forward or backward lateral movement of the sample collection device 400. Such a structure provides tactile confirmation for the user that the sample collection device was inserted fully and correctly; additionally, the two-way lock gives structural support to the rupture/seal mechanism. By preventing intentional and accidental removals of the sample collection device 400 from the cartridge 800, the risk of contact with the sample is minimized. Accordingly, the biohazard risk is minimized. Such a structure allows for easy disposal of the system into the normal trash.

Within the cartridge 800, the input tunnel 812 of some embodiments extends from an aperture on a surface of the cartridge 800 to a first reservoir 824. In the depicted embodiment, the plurality of reservoirs includes a first reservoir 824, a second reservoir 828, and a third reservoir 826. In other embodiments, only two or four or more reservoirs may be present. These reservoirs 822 are each separate from the others and no cross-mixing of their contents occurs within the reservoirs. As visible in the top and perspective views of FIGS. 10A and 10B, each of the plurality of reservoirs 822 is, at least at times, in fluid connection with a microfluidic analysis channel 832 by way of a reservoir outlet. In certain embodiments, the bottom "floor" or bottom internal surface of each reservoir is not flat, but rather, angled downward toward the outlet, with the intersection of the reservoir and the analysis channel 832 located at the lowest height or deepest depth. Such embodiments help encourage flow of all reservoir contents into the analysis channel 832, thereby minimizing dead volume. In various embodiments, each reservoir outlet has a valve disposed therein (such as, for example, valves 825, 827, 829), which fully seals the outlet and prevents liquid from flowing from the reservoirs into the analysis channel 832 prior to use. In use, in accordance with a method described in more detail below, the plurality of valves can open in a timed manner such that contents from each of the plurality of reservoirs 822 can flow sequentially into the analysis channel 832.

In the depicted embodiment, the first reservoir 824 is furthest downstream and closest to the input channel 822. This is by design so that, upon insertion of the sample collection device 400, the head 420 enters the first reservoir. The first reservoir 824 is at least partially filled with the sample preparation reagents described above and a first liquid. Within this disclosure, the terms "first reservoir" and "sample preparation reservoir" may be used interchangeably. In various embodiments, when the sample collection device 400 enters the first reservoir 824, the first reservoir 824 becomes further filled with sample particles, including one or more target analytes, if present in the sample. Additionally, in various embodiments, when the sample collection device 400 enters the first reservoir 824, the liquid is gently mixed to suspend and hybridize particles within the reservoir. In some embodiments, the target analytes in the sample hybridize and bind, at least, to the magnetic particles and affinity molecules present among the sample preparation reagents forming magnetic particle-bound complexes. When the first valve opens, liquid from the first reservoir 824 acts as a transport medium causing the magnetic particle-bound complexes and other particles to flow from the first reservoir 824 into the analysis channel 832. Advantageously, the liquid serving as the mixing medium and storage medium within the first reservoir 824 also acts as the flow medium to transport the contents of the first reservoir 824 to an analysis zone within the analysis channel 832 without the need for a pump.

The second reservoir 828, present in some but not all embodiments, is at least partially filled with a wash solution. The term "second" as used herein, refers to the order in which solution from the reservoir is released into the analysis channel 832 rather than the position of the reservoir within the cartridge 800. The second reservoir 828 is located furthest upstream in various embodiments. In such embodiments, when a corresponding second valve 829 opens, the wash solution flows from the second reservoir 828 into the analysis channel 832, thereby removing all or substantially all unbound detector agents and/or unbound competitive binding agents from the analysis channel 832. Locating the wash solution in the upstream-most reservoir ensures that all free-floating, unbound molecules from the sample preparation reservoir 824 are washed from the analysis channel 832 and reduces the likelihood of having any non-specific binding of significance occur within an analysis zone of the analysis channel 832.

The third reservoir 826 is located upstream of the first reservoir 824, for example, between the first reservoir 824 and the second reservoir 828. The third reservoir 826 is at least partially filled with a chemical substrate in solution. In various embodiments, the solution of the third reservoir 826 includes a substrate that undergoes a reaction in the presence of a signaling agent from the first reservoir 824. For example, in some embodiments, the substrate of the third reservoir 826 undergoes an oxidation reaction in the presence of an oxidizing enzyme from the first reservoir 824. In various embodiments, when the third valve 827 opens, liquid from the third reservoir 826 acts as a transport medium causing the chemical substrate to flow from the third reservoir 826 into the analysis channel 832.

In various embodiments, liquid flows from each of the plurality of reservoirs 822 into the analysis channel 832 and continues to flow in a downstream direction within the analysis channel as a result of capillary action. In certain embodiments, a vent is provided in or over each reservoir to allow for air to replace the liquid emptying from each reservoir into the analysis channel. Without proper ventilation, fluid may not flow within the cartridge. In some embodiments, the vent is formed by placing an air permeable membrane, such as, for example, a PTFE membrane, over the plurality of reservoirs. In some such embodiments, at least portions of the cover component of the cartridge housing may be formed of PTFE; in other embodiments, an opening may be provided in the cover component over the reservoirs, which is sealed with a PTFE membrane. Advantageously, a membrane such as a PTFE membrane that is air permeable but not liquid permeable provides a means for sealing off the top of each reservoir to prevent liquid leakage while allowing for the liquid to drain out of the reservoir into the analysis channel. Additionally, one or more vents 835, 836 may be provided over all or a portion of the analysis channel, in order to allow displaced air to vent as the liquid flows into the channel. Bubbles are often a problem in microfluidic systems. This issue is countered in some embodiments with the strategic placement of the vents, which allow for passive degassing of bubbles. For example, in some embodiments, all or a portion of the top side of the microfluidic channel (within the internal component of the cartridge) is replaced with a PTFE membrane or other air permeable membrane. In such embodiments, the membrane forms the ceiling of much of the channel. The pore sizes of the membrane can vary and can be selected to include pores of 0.1 microns to 3 microns in diameter. In some such embodiments, the membrane is sealed onto the channel and/or over the reservoirs with adhesive.

Attachment of an air-permeable membrane within the cartridge during assembly may be achieved using any suitable manufacturing process. In some embodiments, adhesive is applied to a bottom side of the membrane, and the membrane is taped to a bottom wall of the analysis channel; the bottom wall of the channel is formed of a surface of the circuit board component. A vacuum is then applied by pushing air through one or more vents; the vacuum raises the membrane such that an adhesive portion of the membrane contacts the side walls of the analysis channel, forming an adhesive seal. In effect, the membrane will be sucked into place and bonded to the side walls of the analysis channel through the use of an applied vacuum and adhesive.

To facilitate capillary flow in the analysis channel, in various embodiments, the interior surfaces of the channel are made to be hydrophilic. As used herein, "hydrophilic" refers to an affinity for a surface and/or molecule to maximize its contact area with water. A hydrophilic surface is one in which the contact angle of a droplet of water is less than 90 degrees. In some embodiments described herein, surfaces having a contact area of less than 60 degrees are achieved. As used herein, "capillary flow" or "capillary action" refers to movement of fluid along a fluidic channel driven by at least two physical properties of the fluid and the channel. The physical properties include: hydrophilic adhesion of the molecules of the fluid in contact with surfaces of the channel, and intermolecular cohesive forces within the body of liquid which help to draw the bulk of the fluid along as the molecules closest to the hydrophilic surfaces of the channel propagate along the channel surface.

In various embodiments, the analysis channel is defined by two or more walls, and some or all such surfaces are made to be hydrophilic. In some embodiments, the analysis channel includes a first semi-circular wall formed into the internal component of the cartridge and a second wall formed of a surface of the circuit board component of the cartridge. In other embodiments, such as, for example, the embodiment depicted by the cross-sectional view of an analysis channel in FIG. 17A, the walls of the analysis channel 1732 include three walls that are carved, etched, or otherwise formed into the internal component 1730 of the cartridge and the fourth wall is formed of a surface of the circuit board component 1750.

Figure 17A:
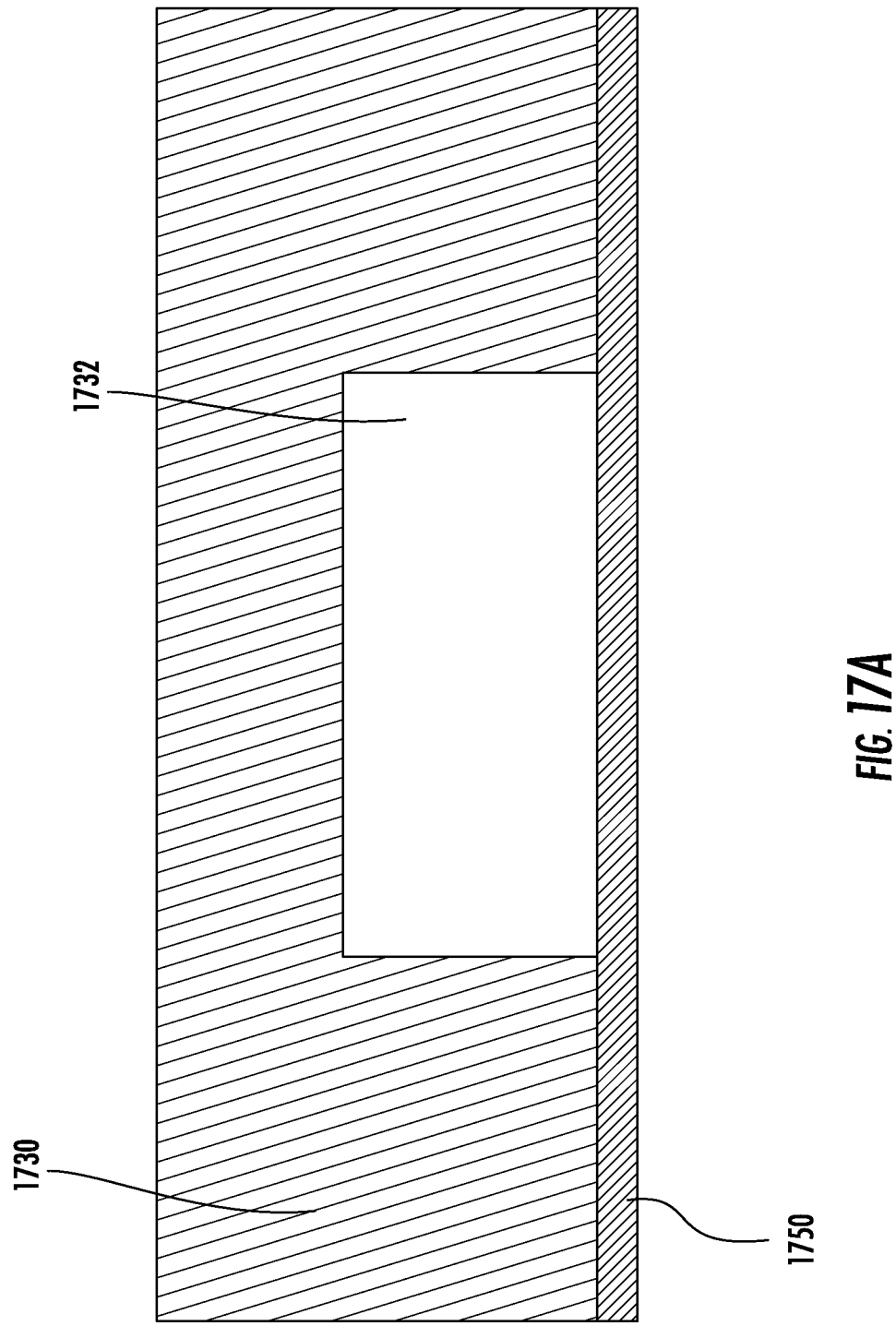
Figure 17B:
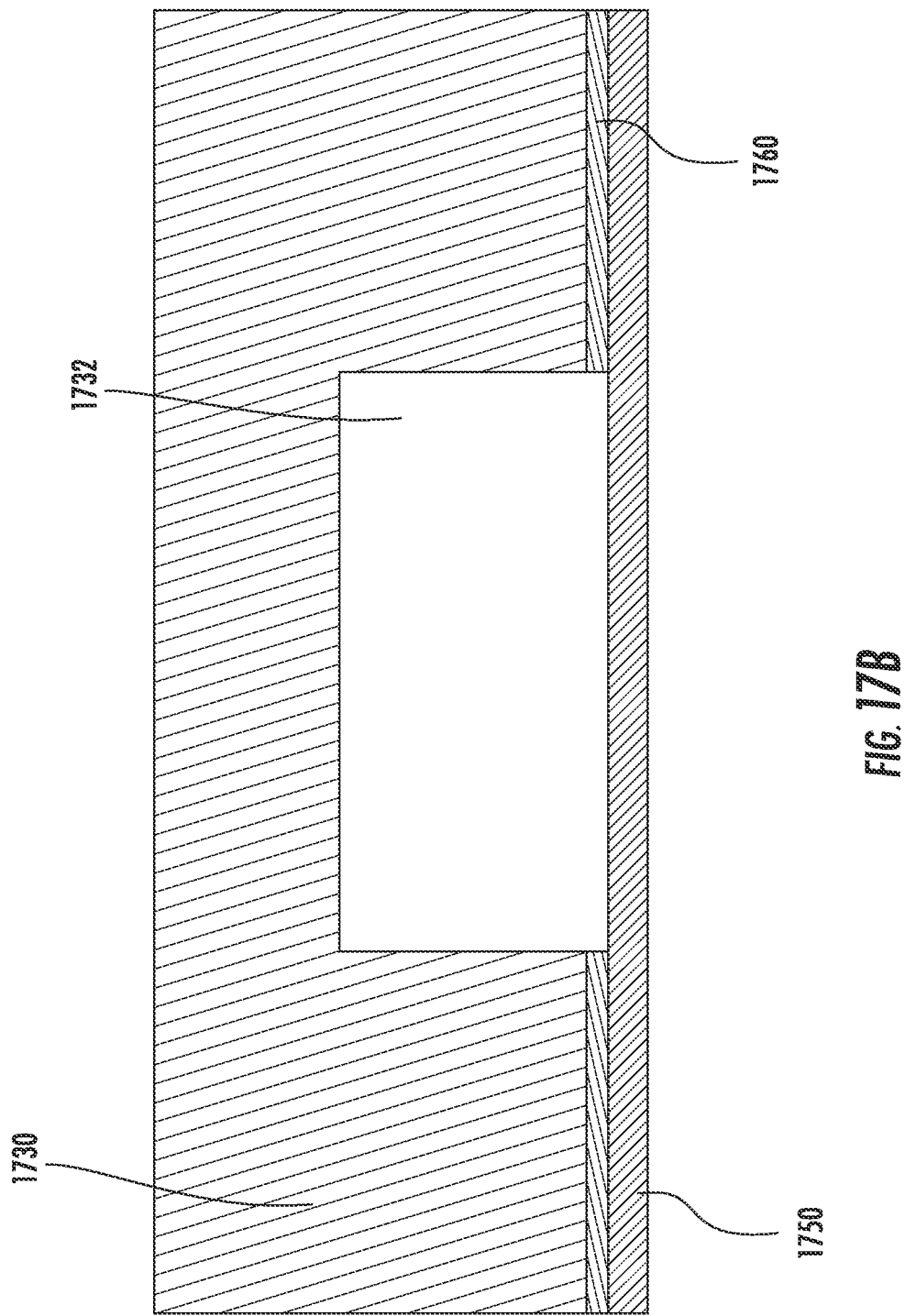
Figure 17C:
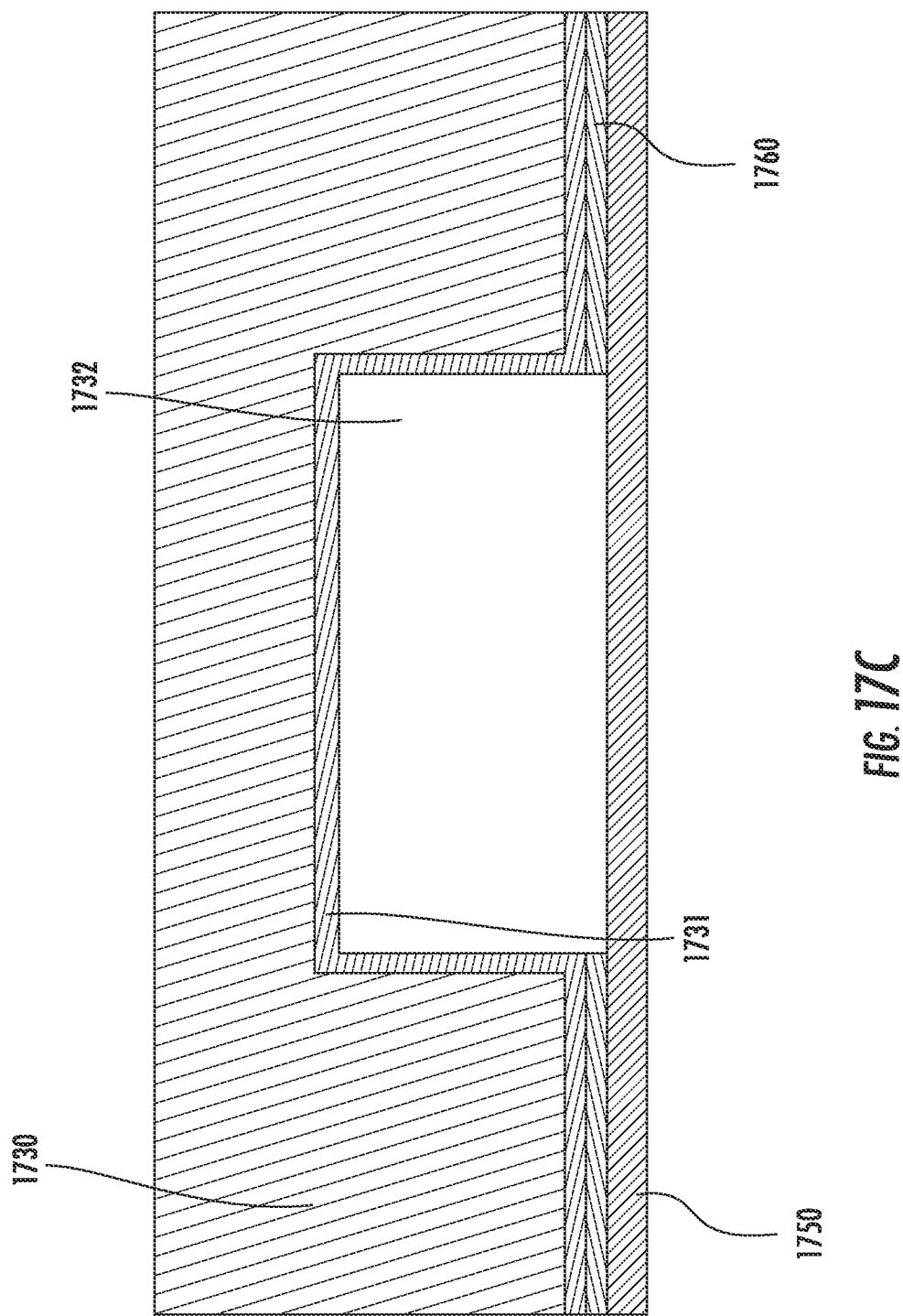

Various materials or surface chemistry modifications can be used to create an analysis channel having hydrophilic walls. For example, the internal component 1730 and the analysis channel walls formed of the internal component 1730 may be made from a thermoplastic resin as shown in FIG. 17A. Such an embodiment is also depicted in FIG. 17B; in FIG. 17B, an adhesive layer 1760 is also shown coupling the internal component 1730 to the circuit board component 1750 to form the analysis channel 1732. As another example, such as, for example, the embodiment provided in FIG. 17C, one or more surfaces of the internal component 1730, including the surfaces forming walls of the analysis channel 1732, may undergo pegylation grafting mediated by plasma treatment to activate the surfaces such that polyethylene glycol (PEG) will bond thereto, making a hydrophilic and protein-resistant modified surface 1731. Additionally, in some embodiments, a commercially available lateral flow type membrane, may be disposed within the channel interior to provide a wicking material within the channel.

Figure 17D:
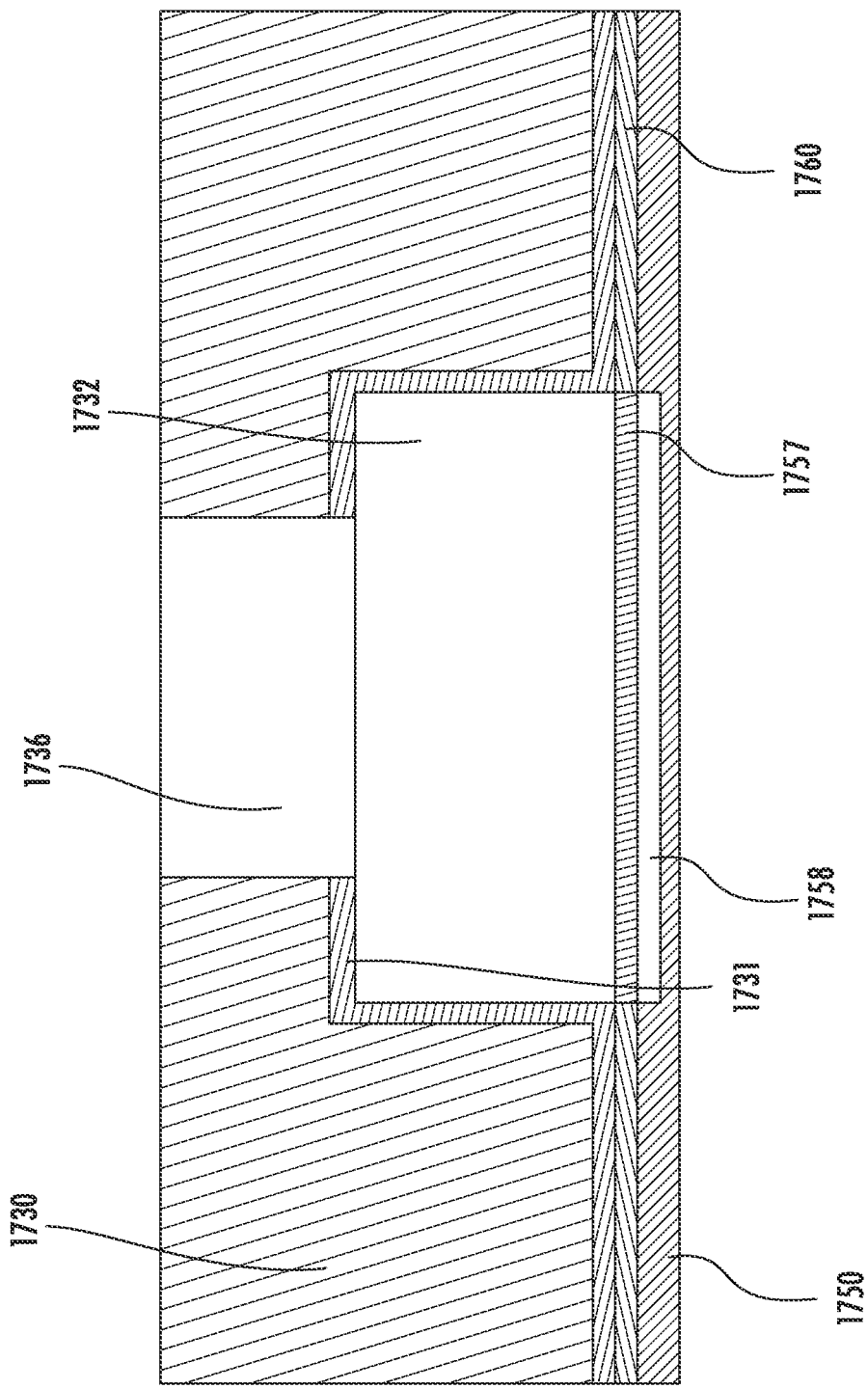

As described above, in some embodiments, the cartridge includes a means for venting gases from the analysis channel. As shown in FIGS. 17D and 17E, in some embodiments, the means for venting gases includes one or more vents 1736, which are formed of small holes within the internal component 1730. In some embodiments, the walls defining the vents 1736 are hydrophobic and the holes are sufficiently small such that aqueous liquids within the analysis channel 1732 are repelled from the vents 1736 and do not leak. As shown in FIG. 17F, in another embodiment, a bubble bypass segment 1733, defined by the internal component 1730 is provided in a top portion of the analysis channel 1732. The bubble bypass segment 1733 is sized and positioned to allow gases to flow through bubble bypass segment 1733 while liquids within the analysis channel remain within the lower, main segment of the channel 1732. In some embodiments, the bubble bypass segments 1733 are provided between two vents 1736 and serve to transport gases from the analysis channel to the vents 1736 for release.

Figure 17G:
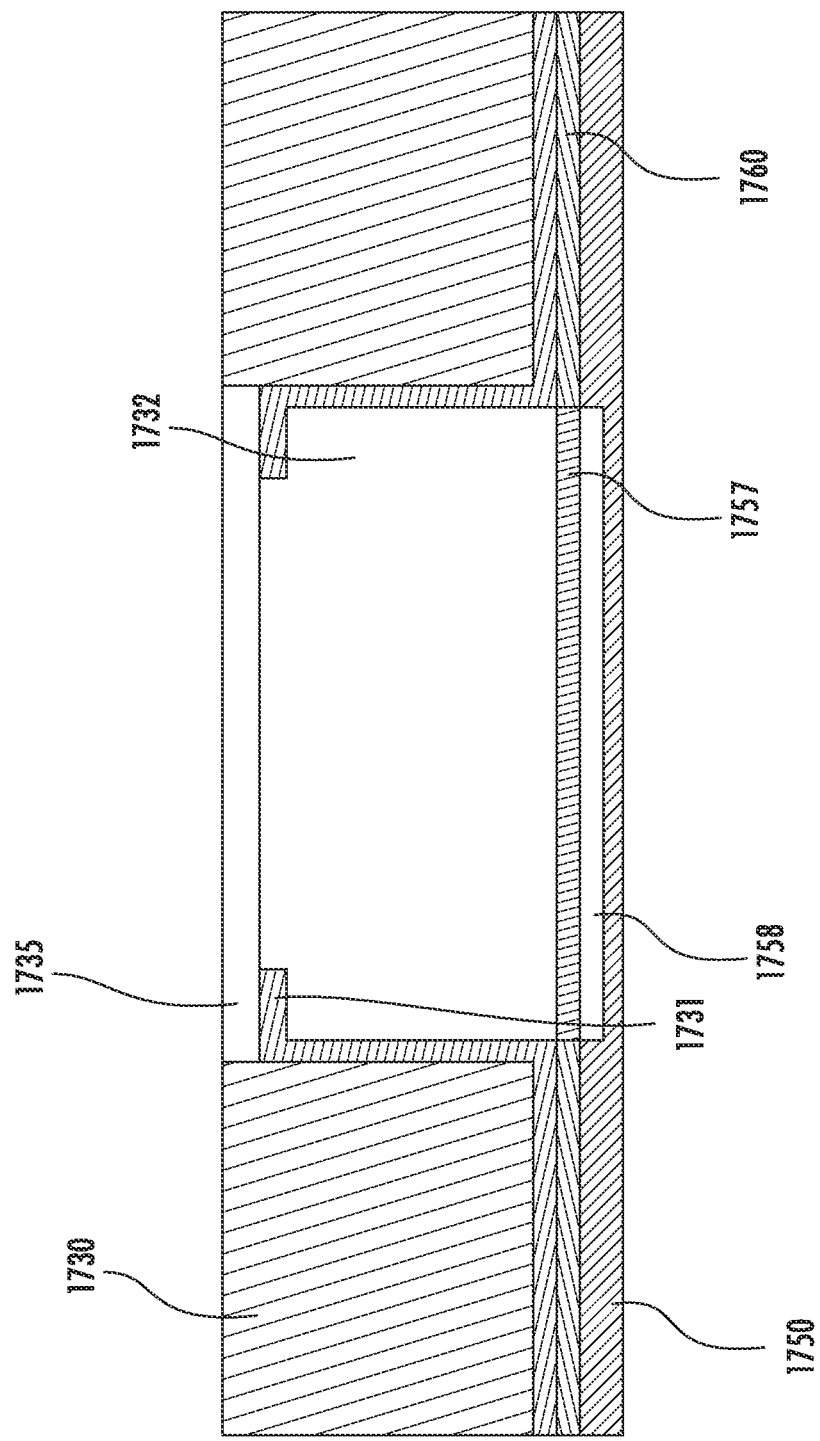
Figure 17H:
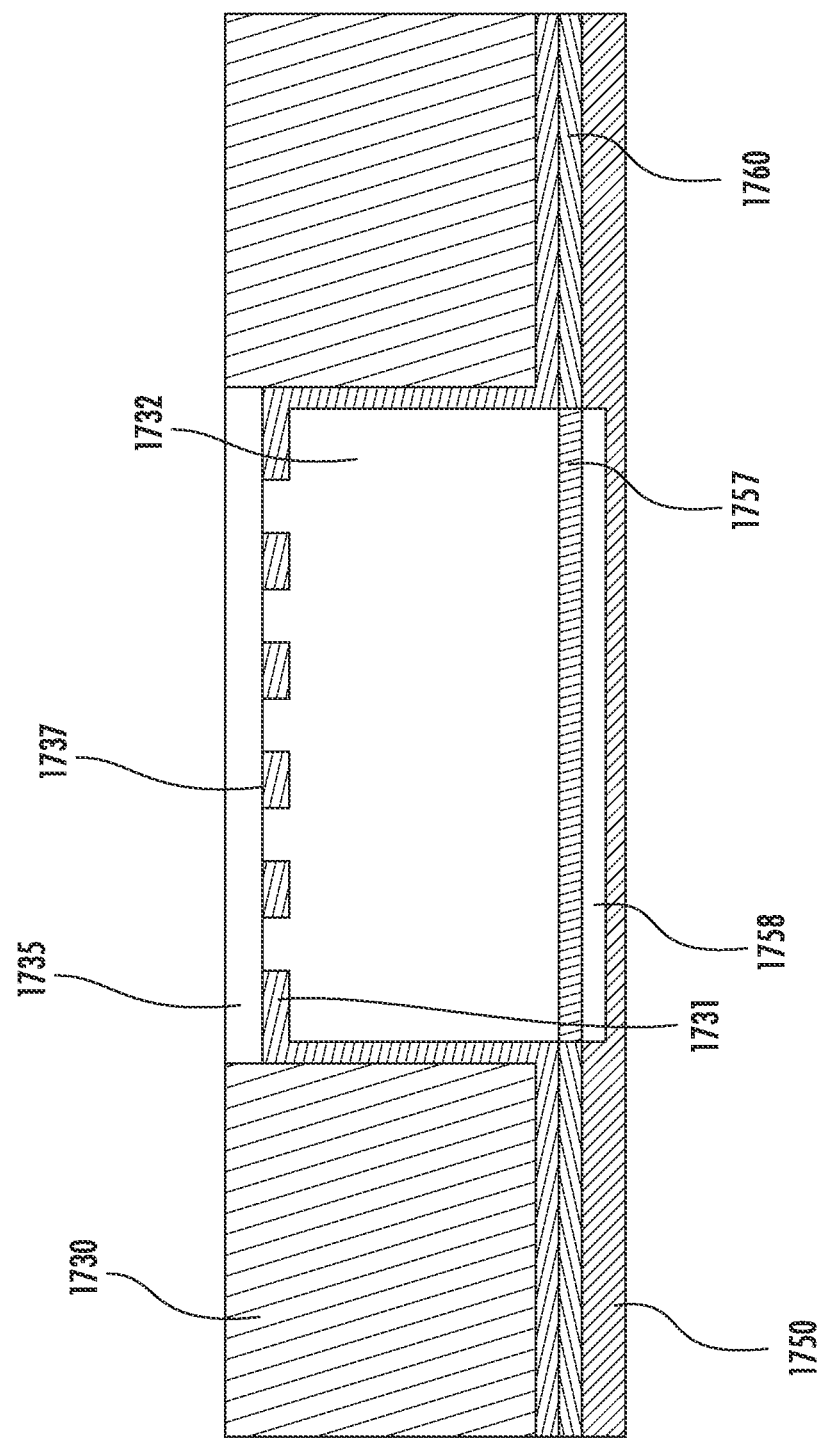
Figure 17I:
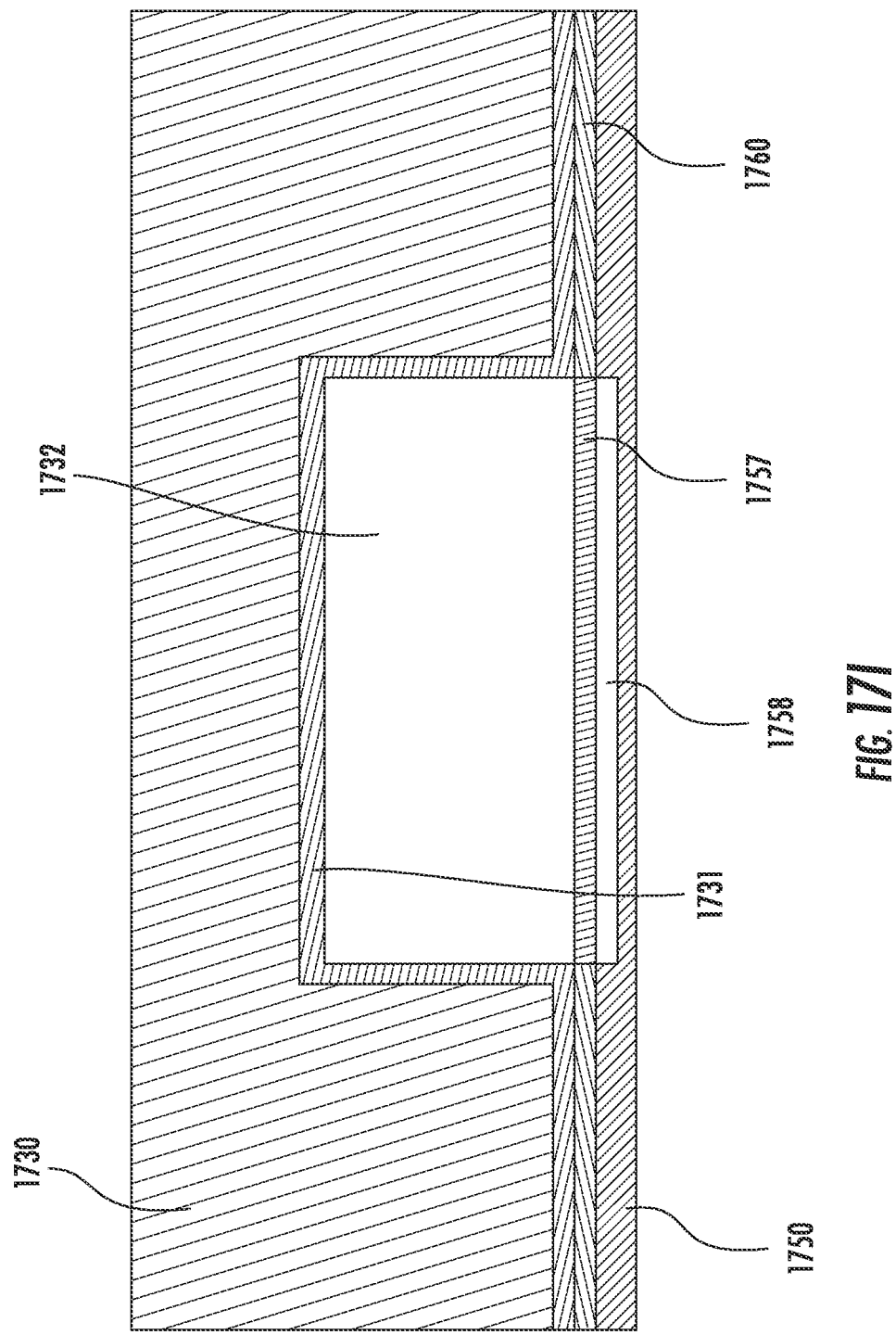

In other embodiments, the means for venting gases from the analysis channel 1732 includes a breathable membrane, such as a PTFE membrane, which replaces one analysis channel wall otherwise formed of the internal component 1730. One such embodiment is depicted in FIG. 17G with a top wall of the analysis channel 1732 replaced by a breathable membrane 1735. In some embodiments having a breathable membrane 1735 for venting, prewetting of the membrane 1735 may be required, because some breathable materials, such as PTFE, are hydrophobic. To eliminate the need for a distinct prewetting step, structural prewetting may be utilized in some embodiments. One such embodiments is depicted in FIG. 17H. As shown, to "structurally prewet" a breathable membrane 1735, rails 1737 of hydrophilic material may be provided, which run the length of the breathable membrane. Such rails 1737 promote the flow of liquid along the rails, for example, from a reservoir into the analysis channel 1732 and/or along the length of the analysis channel 1732. The hydrophilic rails 1737 help overcome the hydrophobic resistance of the membrane. These rails 1737 can be formed in a multitude of ways and are constructed to include thin plastic rails spanning the length of the membrane ceiling 1735. In some embodiments, adhesives disposed directly on the membrane can form the rail; in another embodiment, the rail may be formed by a patterned surface modification of the membrane which causes a hydrophilic surface modification to run the length of the analysis channel 1732.

Additionally, as described in more detail below, in some embodiments, one or more sensors are disposed on the circuit board component 1750 within the analysis channel 1732. As depicted in FIGS. 17D-17I and specifically identified in FIG. 17I, the sensor 1758 may be formed of gold or other conducting metal, and as described below with reference to FIG. 18A, may include additional surface chemistry modifications 1757. In various cartridge embodiments described herein, such as, for example, in cartridge 700 of FIGS. 7A and 7B and cartridge 800 of FIG. 8, it is contemplated that the analysis channel 732/832 may include any or all of the features described and/or depicted within any of FIGS. 17A-17I or any other features known to those skilled in the art.

Additionally, to facilitate flow via capillary action in the analysis channel, in various embodiments, an absorbent material is provided at the downstream-most end of the analysis channel. One example of an absorbent material, in the form of an absorbent pad 834, is visible in FIG. 10A. The absorbent material or pad 834 wicks liquid from the analysis channel 832, thereby encouraging liquid to flow downstream to the absorbent pad 834. In some embodiments, the absorbent pad 834 acts as a waste receptacle, collecting all waste liquids and waste particles after they have flowed through the analysis channel 832. In various embodiments, the absorbent pad's size and degree of absorbency is selected to meter the flow of liquids and particles within the analysis channel 832. For example, in some embodiments, the volume of liquid that the absorbent pad 834 can wick must be great enough to drain all liquid from the first (sample preparation) reservoir 824 and the second (wash) reservoir 828 and draw the liquid carrying the chemical substrate from the third (substrate) reservoir 826. Such a condition may serve as the lower limit of absorbency. Additionally, acting as an upper limit is the requirement that the flow of the liquid carrying the chemical substrate must slow or stop over an analysis zone of the analysis channel 832 so that the chemical substrate has time to react with signaling agents localized within the analysis zone.

As shown clearly, for example, in FIGS. 7B, 8, and 11A-11C, the cartridge of various embodiments also includes a printed circuit board, 750, 850, and 1150, respectively, referred to herein as a circuit board or circuit board component. The circuit board component is coupled to the internal component of the cartridge. The circuit board component 750 of FIG. 7B is provided, in isolation, in FIGS. 18A and 18B. The circuit board component 750 includes electrical components, for example, one or more of: a resistor, electrical leads 754, vias 756, and sensors 758 needed for detection of target analytes. Although described separately, it is to be appreciated that electrical components of the circuit board component 750 need not be separate structural elements. One or more electrical components and/or circuits may perform some of or all the roles of the various components described herein. In some embodiments, the resistor is provided as a unique-identifying tag, which allows for a reader device (described in more detail below) to distinguish between cartridge types. The resistor may include a small surface mount resistor, a resistive-ink based resistive element, or any other resistive element that allows the reader to "read" the resistor and thereby identify the cartridge type. As used herein, cartridges differ in "cartridge type" if they are configured for the detection of different target analytes. In other embodiments, different non-resistive means of identifying the cartridge type are employed.

As described in more detail below, the electrical leads 754 of various embodiments are provided to establish electrical connections and continuity with a reader device. As shown in FIG. 18B, the electrical leads 754 are electrically coupled to the vias 756, providing electrical current to such components when activated by the reader device. A via is a standard product on printed circuit boards and is typically used to enable signal traces on one layer of a circuit board to continue electrically with another layer. The vias provide electrical continuity through multiple layers. Such vias are excellent conductors of heat; they are able to transfer heat to a very precise location without affecting the surrounding areas, because the surrounding material that comprises most circuit boards is an excellent insulator of heat. Thus, in various embodiments, a plurality of vias 756 are provided in the circuit board component, and each via 756 is disposed under, over, or adjacent to a phase-changeable, heat-actuated valve disposed in a reservoir outlet to create a valve actuating element. The precision of heat transfer associated with the vias 756 allows for minimal crosstalk between valves located close to each other; thus, the timing of valve actuation can be carefully controlled for each valve. In some embodiments, the valves are formed of a wax, for example, a hydrophilic wax, and the vias 756 act as conductors of heat to melt wax at precise points of time, as controlled by a reader device. One or more heating elements generate the heat that is to be conducted to the exact location where the wax needs to be melted. Upon melting of a wax valve disposed in the outlet of a reservoir, the outlet is no longer occluded and the reservoir has an opening through which its fluid contents can drain into the analysis channel. The heating element of some embodiments forms part of the circuit board component. For example, in the embodiment of FIG. 18B, the heating element is a resistive heating element appearing as a serpentine trace 755 located on the bottom side of the circuit board component 750, surrounding the via 756. In other embodiments, the heating element is located external to the cartridge, for example, on the reader. In various embodiments in which a resistive heating element is used, in order to generate heat, current is allowed to flow through the resistive heating element, for example, through actuation of a transistor. Current passing through the resistive heating element generates heat through Joule heating. The heat is conducted to the via due to physical contact between the resistive heating element and the via. In various embodiments, the heat is then conducted through the via up the wax barrier and a phase transition, such as, for example, melting, of the wax occurs.

In order to ensure full melting of the wax with precise timing, in various embodiments, the wax valves are carefully constructed within the outlets of the reservoirs. For example, in some embodiments, it is preferable for the wax valves to have the minimum height necessary to occlude the outlet of the reservoir; the minimal height minimizes the distance heat must travel to melt the wax. One example method for realizing a wax barrier having such characteristics involves applying melted wax to a pre-heated via. Advantageously, when the via is pre-heated, it takes longer for the wax valve to solidify relative to a room-temperature via; thus the wax has more time to flatten and expand outward before hardening. "Pancaking" of the wax is desirable to minimize the height, which will maximize the chance of proper melting actuation of the valve. Additionally, the heating of the via facilitates a greater level of contact area between the wax and the via such that a greater proportion of the wax experiences the heat, also maximizing the chance of proper valve actuation. The method of heating the via prior to deposition of wax is further enhanced with the following method: the opening of the reservoir is aligned over the via such that when the melted wax is applied to the pre-heated via, the opening at the bottom of the reservoir is spatially close to the via such that when the wax hardens, the wax adheres simultaneously to multiple inner walls of the reservoir and the via itself. This is advantageous for enhancing the manufacturing yield of intact valves that fully occlude the opening to the analysis channel such that no inadvertent flow of liquid from the reservoir occurs.

Figure 19:
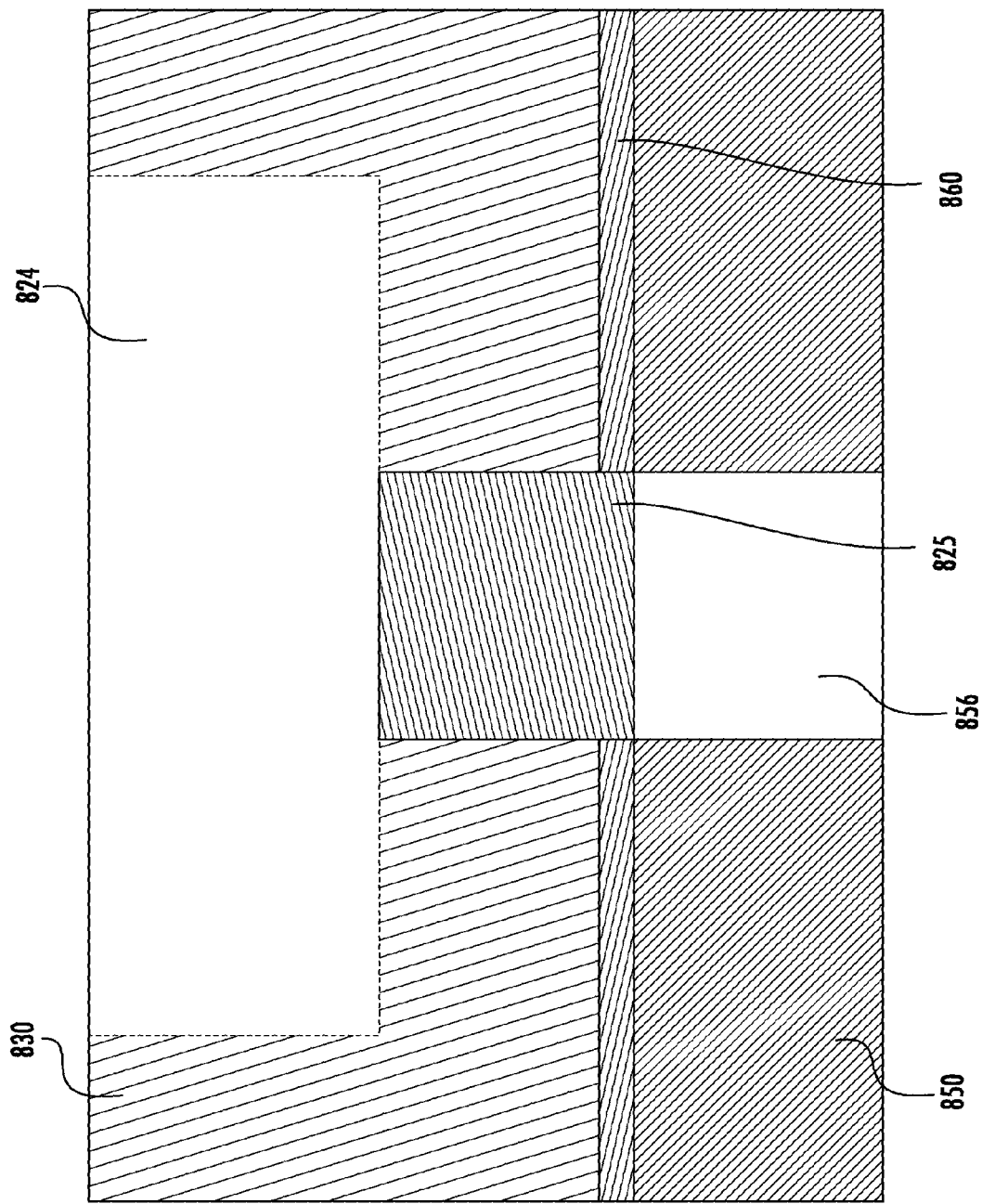
FIG. 19 depicts a cross-sectional view of a first reservoir from the cartridge embodiment of FIG. 8.

A cross-sectional view of one embodiment of the valve 825 is provided in FIG. 19. The valve 825 is located within an outlet at the bottom of the reservoir 824 of the cartridge 800. As depicted in FIG. 19, the reservoir 824 is defined by walls of the internal component 830. In some embodiments, the outlet is formed of a hole within a bottom wall of the internal component 830. In various embodiments, the circuit board component 850 is disposed below the internal component 830 and affixed to the internal component 830 with the use of an adhesive 860, such as, for example, a double-sided adhesive tape which may be hydrophilic to support the capillary flow of fluid. In various embodiments, the valve 825 is formed of a heat-sensitive, phase-changeable material, such as, for example, a hydrophilic wax. Prior to actuation, the wax or other heat-sensitive material of the valve 825 is in a solid or semi-solid state and is sized and shaped to fill an entire cross-section of the outlet such that no liquid can escape from the reservoir 824 into the analysis channel 832. As depicted, the heat-actuated valve 825 of some embodiments is aligned directly above a via 856 or other localized heat-conductive element. Such alignment allows for the localized application of heat to induce a phase change in the valve 825 without causing a phase change of any neighboring valves. In various embodiments, the phase change melts or otherwise transforms the heat-sensitive material such that it no longer causes full occlusion of the outlet, but instead permits liquid in the reservoir 824 to flow into the analysis channel 832.

In some embodiments, the wax material disposed upon the via, and which occludes the opening of the reservoir to prevent the liquid from flowing into the analysis channel, is preferably a hydrophilic material such as hexadecanol or octodecanol. This advantageously promotes, rather than obstructs the flow of liquid past any wax bits that harden within any area of the analysis channel after valve actuation. These materials also preferably have a melting temperature between 50 and 100 degrees Celsius, which allows for actuation with reasonable power-consumption for a battery-operated device, yet remains unactuated in general handling and storage environments and/or during a sonication protocol. In some embodiments, the amount of wax disposed upon the via is below 1 microliter in its liquid state, and in some such embodiments, the amount is less than or equal to 0.5 microliters. In at least some embodiments, it is preferable to use at little wax as possible in order to reduce any occlusion of the analysis channel and maximize full valve actuation when heat is applied. In some embodiments, the valve also has a feedback-and-control system that allows for a consistent thermal profile to be achieved at the via for consistent valve actuation. Furthermore this feedback-and-control system may incorporate sensing elements to enable the system to confirm that each valve has properly actuated.

Figure 20B:
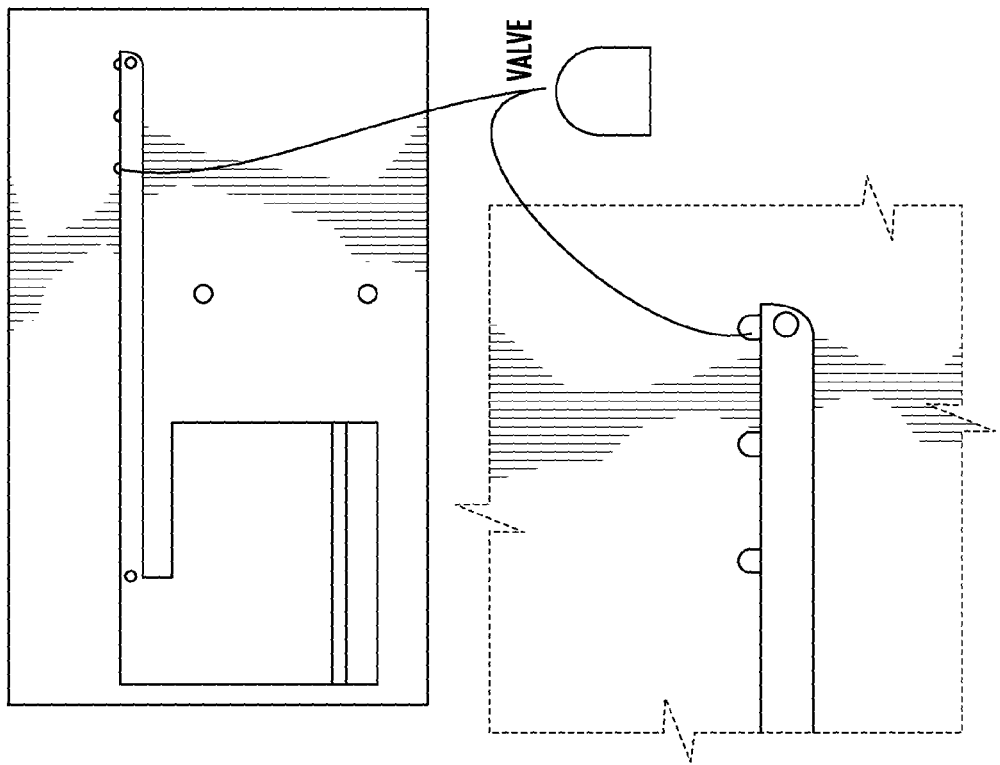
FIGS. 20A and 20B depict valves positioned within one embodiment of a cartridge.
Figure 20A:
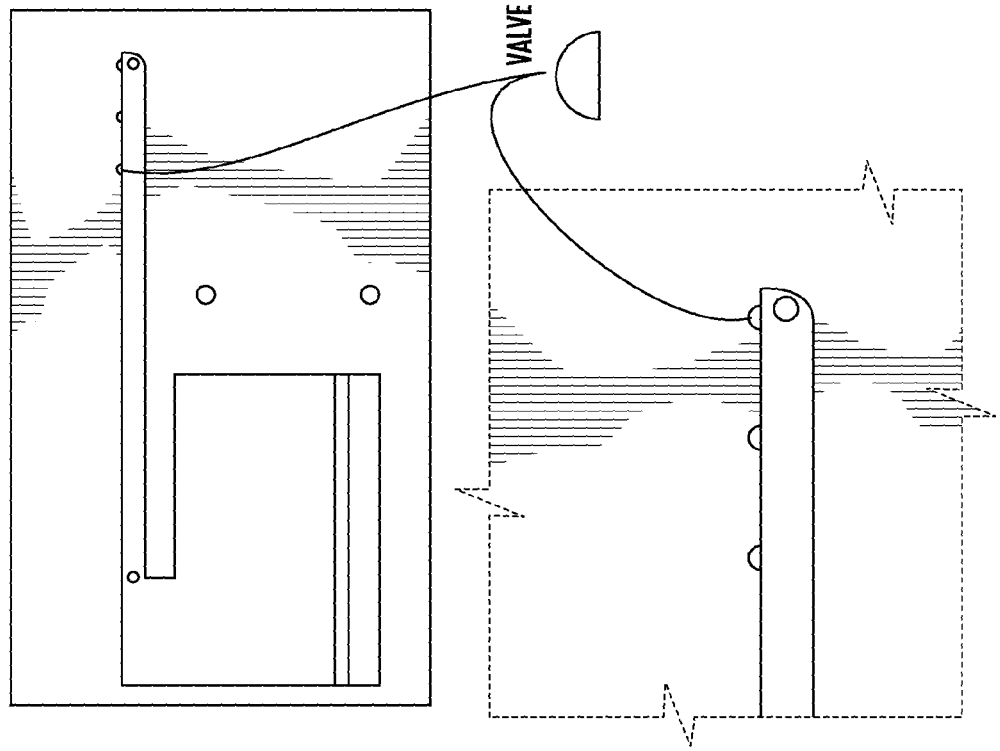

In some non-limiting embodiments, the outlet at the bottom of the reservoir is sized and shaped, for example, as depicted in FIG. 20A or FIG. 20B. In FIG. 20A, the valve opening/outlet at the bottom of each reservoir is depicted as a semicircle in fluidic communication with the analysis channel. In some such embodiments, the semicircle has a diameter of approximately 1 mm, a size which may help reduce the amount of wax necessary to hold back the fluid of the reservoir from entering into the analysis channel. Alternatively, FIG. 20B depicts an outlet formed of a semicircle with a boundary extension. In some such embodiments, the boundary extension has a length between 0.1 mm and 1 mm. Compared to FIG. 20A, the boundary extension of FIG. 20B may enhance proper valve actuation and flow by providing a larger surface area for wax melted during the course of valve actuation to solidify onto before entering into the analysis channel. Such a configuration may reduce the amount of wax entering into the analysis channel. Similarly, during valve construction, the extensions from the semi-circle opening allow for an increased area wherein the wax can harden without occluding the analysis channel.

Returning to FIG. 18A, the electrical leads 754 are also electrically coupled to the sensors 758; such an electrical connection allows signals detected by the sensors 758 to be delivered to the reader device for processing. In various embodiments, the sensors 758 and the area of the analysis channel above them form the "analysis zone", mentioned elsewhere herein. The sensors 758 are strategically located such that, when the circuit board 750 is included within the assembled cartridge 700 with a surface of the circuit board 750 forming one wall of the analysis channel 732, the sensors 758 are disposed within the analysis channel 732. As shown in FIG. 18A, a plurality of sensors 758 may be provided, each spaced relative to the others, and all aligned with the analysis channel 732. The sensors 758 are electrochemical sensors, each forming an electrochemical cell within the analysis channel. In this embodiment, each sensor 758 is formed of a working electrode 758*a*, a reference electrode 758*b*, and a counter electrode 758*c*. In some embodiments, an oxidation reaction may occur at an electrochemical sensor 758 if an oxidizing enzyme bound indirectly to a magnetic particle is present at the sensor 758 and an appropriate chemical substrate is introduced into the analysis channel 732. In such embodiments, the working electrode 758*a* releases electrons to replenish electrons stripped from the substrate by the oxidizing enzyme in a quantity proportional to the amount of oxidizing enzyme present. The release of electrons from the working electrode is a current which may be detectable as a signal within a circuit connected to the sensor 758. The sensors 758 can thereby indirectly detect the presence, absence, and/or quantity of oxidizing enzymes localized in the analysis zone of such embodiments. A computer, for example, within the reader device described below, can then correlate the presence, absence, and/or quantity of a target analyte to the presence, absence, and/or quantity of oxidizing enzymes. The functions of such a computer are described in more detail below. In various embodiments, one or more magnetic fields are used to facilitate localization of the enzymes or other signaling agents within the analysis zone. Advantageously, in such embodiments, no affinity molecules need to be pre-bound to the sensors to achieve localization, which would otherwise significantly slow the analyte quantification process due to the limits of diffusion-based hybridization kinetics. Details of the magnetic fields are also provided below.

In some embodiments, the electrochemical sensors 758 where detection takes place are made through an ENIG process and thus have gold on the surface. In other embodiments, gold or gold-plated sensors are used that have not been made through an ENIG process. In some embodiments, at least the working electrode 758*a* of each sensor 758 has a surface chemistry formed of thiolated ethylene glycol and/or a dithiol such as hexaethylene glycol dithiol for added stability. The hydrophilic nature of the head groups of such surface chemistry facilitates flow and protein resistance. Additionally or alternatively, in some embodiments, the surface of one or more of the electrodes is backfilled with mercaptoundecanoic acid, mercaptohexanol, or other suitable backfiller. In some embodiments, the surface of one or more of the electrodes within the sensor 758 is formed through sequential addition and incubation of the ethylene glycol dithiol and the backfiller at unelevated temperatures.

In various embodiments, one or more ambient electrochemical noise sensors, or reference sensors 759, are provided and spaced within the analysis channel away from the site of magnetic particle localization. The reference sensor 759 with its associated circuitry quantifies background noise in the system. Such noise may be due to, for example, the presence of non-specifically bound enzyme. In various embodiments, during processing of the detection results, a computer applies an algorithm to remove the reference sensor signal from the detection sensor signal to account for and/or eliminate system noise and to thereby allow for proper quantification or detection of target analyte.

In some embodiments, the detection is carried out using a standard electrochemical circuit that utilizes a bias potential generated at the reference electrode for the oxidation/reduction reaction to proceed. The potential is held at the reduction potential of the chemical substrate (low enough that there is little nonspecific reduction of reducible species in the solution) so that the flow of electrons to the oxidized molecules can be quantified using an operational amplifier based current-to-voltage (op amp) circuit topology connected to the working electrode. For example, a common substrate molecule, tetramethylbenzidine, is used for HRP. When present, HRP oxidizes TMB molecules, and these molecules are in turn reduced by the working electrode. Since this event occurs in proportion to the amount of HRP present, a change in the current-to-voltage op amp measurement results. Using an analog-to-digital converter, the actual signal can be delivered to a processor for processing. As described in more detail below, in various embodiments, said processor and signal processing components are provided within the reader device.

The Reader Device

The reader device, or reader, of various embodiments is, comprises, or is comprised of, a specialized computer. The computer includes a processor with memory having instructions stored thereon for executing one or more methods for detecting the presence, absence, and/or quantity of target analytes in a sample. In various embodiments, the reader's computer controls the operations of the detection system, controlling when and how various functions of the system occur, such as, for example: mixing of the fluids in the first reservoir of the cartridge, opening of valves, and/or localization of magnetic particles over the sensors. To control such operations, the computerized reader is configured to receive information from, and send information to, physical components present within the reader or cartridge.

Figure 21:
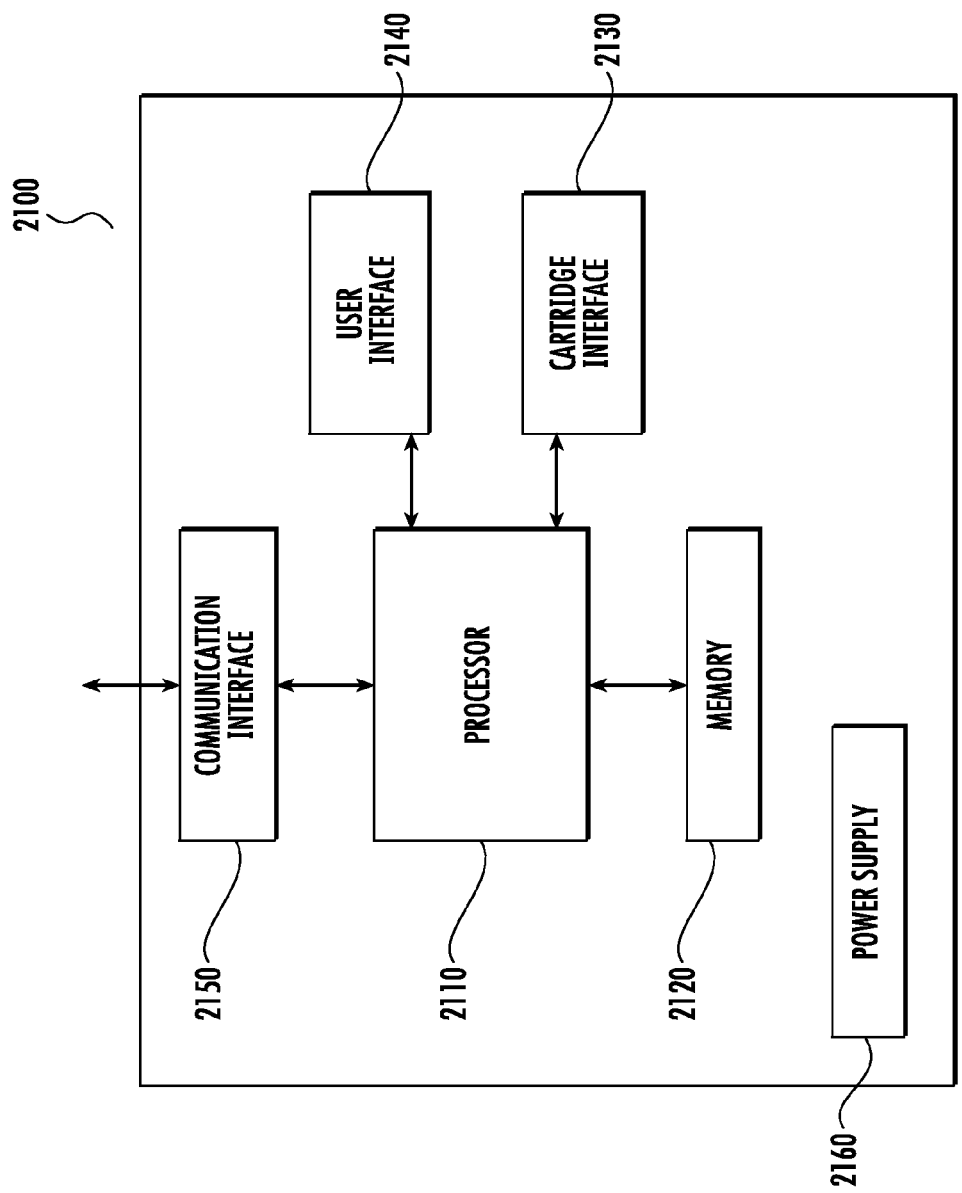
FIG. 21 schematically represents one embodiment of a reader device.

A functional block diagram of one embodiment of a reader is depicted in FIG. 21. Although described separately, it is to be appreciated that functional blocks described with respect to the reader 2100 need not be separate structural elements. For example, the processor 2110 and memory 2120 may be embodied in a single chip. Similarly, the processor 2110 and communication interface 2150 may be embodied in a single chip. In various embodiments, the reader 2100 includes a power supply 2160 such as a battery.

The processor 2110 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 2110 is coupled, via one or more buses, to read information from, or write information to, the memory 2120. The processor may additionally, or in the alternative, contain memory, such as processor registers. The memory 2120 can include processor cache, including a multi-level hierarchical cache in which different levels have different capacities and access speeds. The memory 2120 can also include random access memory (RAM), other volatile storage devices, or non-volatile storage devices. The storage devices can include, for example, hard drives, optical discs, flash memory, and Zip drives.

The processor 2110, in conjunction with software stored in the memory 2120 executes an operating system, such as, for example, Windows, Mac OS, Unix or Solaris 5.10. The processor 2110 also executes software applications stored in the memory 2120. In one non-limiting embodiment, the software comprises, for example, Unix Korn shell scripts. In other embodiments, the software can be programs in any suitable programming language known to those skilled in the art, including, for example, C++, PHP, or Java.

The processor 2110 is also coupled to a cartridge interface 2130, which may include an EDGE card or other electrical connector, to send electrical signals to, and receive electrical signals from, the circuit board component of the cartridge.

In some embodiments, the processor 2110 may be coupled to a user interface 2140. For example, in some embodiments, the reader 2100 may include a touchscreen, LED matrix, other LED indicators, or other input/output devices for receiving inputs from, and providing outputs to, a user. In other embodiments, the user interface 2140 is not present on the reader 2100, but is instead provided on a remote computing device communicatively connected to the reader 2100 via the communication interface 2150. Yet still in other embodiments, the user interface can be a combination of elements on the reader and a remote computing device.

The communication interface 2150 of various embodiments is also coupled to the processor 2110. In some embodiments, the communication interface 2150 includes a receiver and a transmitter, or a transceiver, for wirelessly receiving data from, and transmitting data to a remote computing device. In some such embodiments, the remote computing device is a mobile computing device that provides the system with a user interface; additionally or alternatively, in some embodiments, the remote computing device is a server. In embodiments configured for wireless communication with other devices, the communication interface 2150 prepares data generated by the processor 2110 for transmission over a communication network according to one or more network standards and/or demodulates data received over a communication network according to one or more network standards. The communication interface 2150 of some embodiments may additionally or alternatively include electrical connections for wired communication of signals between the reader 2100 and a remote computing device.

In addition to the computing components, the reader of various embodiments, includes several additional physical components needed to implement target analyte detection. For example, the reader 2200 of FIG. 22 includes a slot, opening, bed, port, or other docking feature, referred to herein as a dock 2210, for receiving a cartridge. The cartridge, when received by the reader 2200, may be disposed on or in, or otherwise coupled to, the reader 2200.

Several of the reader components are strategically positioned in particular locations relative to the dock 2210 in order to achieve desired interactions with the cartridge. For example, the reader 2200 of the depicted embodiment includes an electrical connector 2220 and one or more magnetic field generators 2240, and the location of such components is selected to align with particular features of a docked cartridge. Additionally, some embodiments, including the embodiment of FIG. 22, include a sonication element 2230. Each of these components is described in more detail below.

The electrical connector 2220 of various embodiments is an EDGE card or other connector having pins for electrical connectivity. The connector 2220 is located on, under, within, or adjacent to the dock 2210 and is positioned such that the pins of the connector 2220 make contact with, and establish electrical connectivity with, the electrical leads of a docked cartridge device. The electrical connector 2220 thereby establishes electrical continuity between the sensors on the circuit board component of the cartridge and electrochemical circuitry within the reader. In some embodiments, the electrical connector 2220 of the reader may also establish electrical continuity with a heating element, if present on the circuit board component of the cartridge. In some embodiments, the reader 2200 includes a portion of an electrochemical circuit, which is completed with the addition of the cartridge based on electrical continuity between the electrical connector 2220 and the electrical leads of the cartridge. In such embodiments, the addition of the cartridge completes or closes the circuit. In such embodiments, coupling the cartridge to the reader 2200 activates the reader, causing it to "wake up." Once awoken, the electrical connector 2220 may identify signals being received from a portion of the cartridge to identify what type of cartridge is coupled to its dock. In some embodiments, the electrical connector 2220 may identify a label, such as, for example, a resistive label on the cartridge, which is unique to a particular cartridge type in order to identify the docked cartridge type. In other embodiments, a digital barcode coded within the electrical leads of the circuit board component of the cartridge is read by electrical pins or pads within the reader to identify the cartridge type. In some such embodiments, the circuit board component of the cartridge includes a plurality of electrical leads, some of which are connected to a ground lead and some of which are not. Through a combinatorial usage of the electrical pins and connections between them and a ground pin, and/or with a pull-up/pull-down resistor located on the reader, the condition (e.g., grounded or not grounded) of each pin is sensed as a high or lower voltage than a set voltage, which is read as a logic situation at the processor of the reader to determine whether a particular pin is grounded. In this manner, a combination of grounded and non-grounded pins can be detected and recognized by the reader 2200 to uniquely identify classes of cartridges.

In some embodiments, once awoken, the reader 2200 also determines what test protocol to run for the identified cartridge and/or searches for, and connects to, nearby mobile computing devices.

Figure 22:
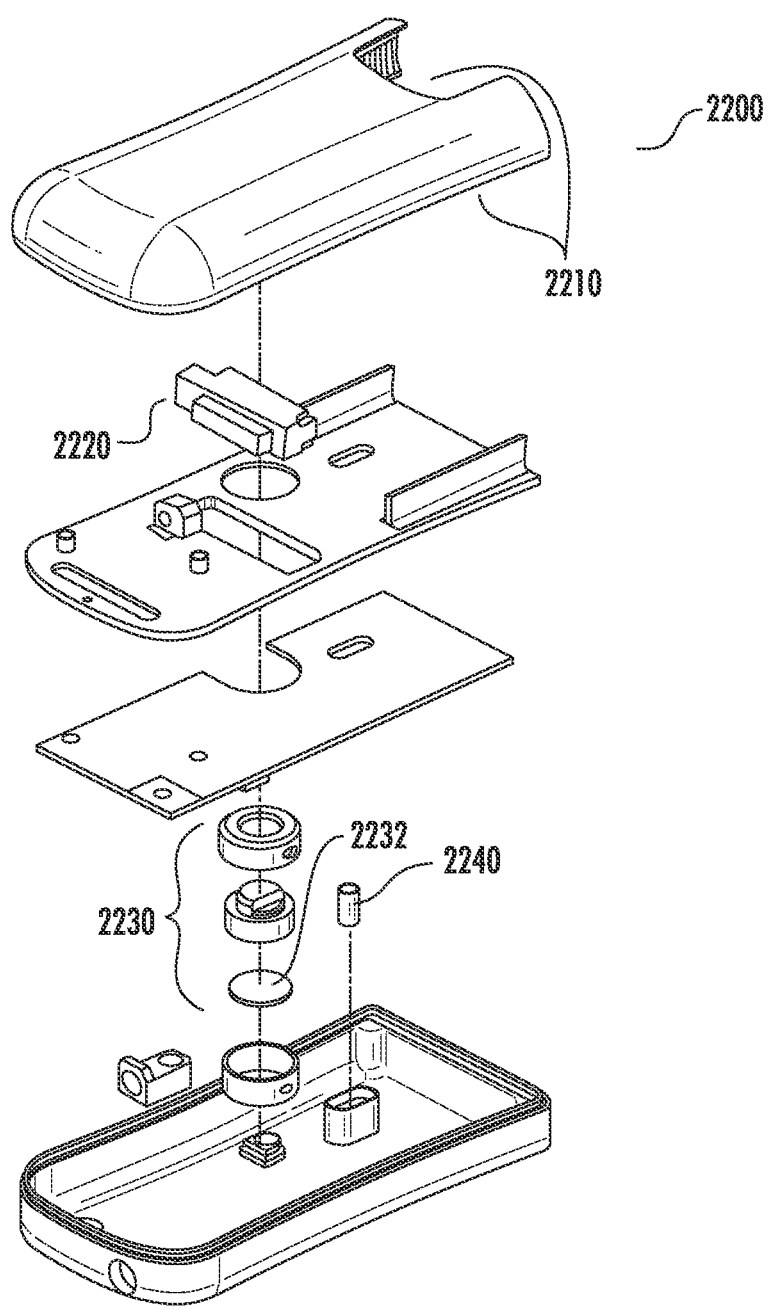
FIG. 22 depicts an exploded view of one embodiment of a reader device.

Continuing with FIG. 22, the reader 2200 optionally includes a sonication component, or sonicator 2230. The sonicator 2230 of various embodiments is located in, under, or over the dock 2210 and is positioned directly or substantially over or under the first reservoir of a docked cartridge. In some embodiments, the docked cartridge includes features to facilitate a close relationship between the sonicator 2230 and the first reservoir. For example, as seen in FIG. 7B, the circuit board component 750 and base component 740 are each shaped to provide a cutout or window 741, 751 in their structures, the cutouts 741, 751 aligned with the reservoirs. Thus, in various embodiments, the sonicator 2230 and the first reservoir of the cartridge can be aligned with no structures provided between them. In some embodiments, when the user slides the cartridge into the dock, the cutouts 741, 751 allow for the sonicator 2230 to be positioned directly underneath the reservoir. Such a configuration enables the sonicator 2230 to transmit controlled amounts of energy into the first reservoir. In other embodiments, the sonicator (or other component performing the sonication steps disclosed herein) is disposed on or forms a bottom wall of the first reservoir 724, such as, for example, as shown in FIG. 11. In other embodiments, no sonicator is provided. In various embodiments having a sonicator 2230, the sonication energy is controlled to achieve mixing and hybridization of components within the first reservoir while limiting damage caused to fragile DNA probes or other molecules.

In some embodiments, the sonicator 2230 includes a pressure-sensitive piezoelectric disk 2232. Optionally, in some embodiments, the sonicator 2230 further includes a high water content blister disposed between the first reservoir and the piezoelectric disk. In some embodiments, the high water content blister is affixed under the first reservoir in the cartridge production process; in other embodiments, it is provided over the sonicator 2230 within the reader. The high water content blister may facilitate delivery of sonic energy from the sonicator 2230 to the first reservoir with minimal attenuation. In some embodiments, the blister is replaced with another appropriately conducting sonication medium. In some embodiments, the component serving as a sonication medium is preferably dry on the outside, with no liquid residue present. In some embodiments, when the cartridge slides into the reader 2200, the sonically conducting medium coupled to the sonicator forms a soft seal with a sonically conducting medium affixed to the bottom of the first reservoir. This "soft seal" may be enhanced by using a conformal sonically conducting medium on the bottom of the reservoir.

In addition to generating sonic energy to mix and hybridize the contents of the first reservoir, in various embodiments having a sonicator 2230, the sonicator 2230 can be used to detect the introduction of the sample collection device into the first reservoir. Advantageously, such detection enables the reader 2200 to initiate an automated start of a testing protocol immediately or substantially immediately following introduction of a sample into the first reservoir. The automated start improves ease of use for lay users; it also ensures a consistent start time relative to sample introduction, thus providing consistent results.

As mentioned above, in some such embodiments, the sonicator 2230 is a pressure-sensitive piezoelectric element. In such embodiments, a wall of the cartridge is designed to flex slightly upon insertion of the sample collection device into first reservoir; such flexing results in a change in pressure, which is detectable by the sonicator 2230.

Figure 23:
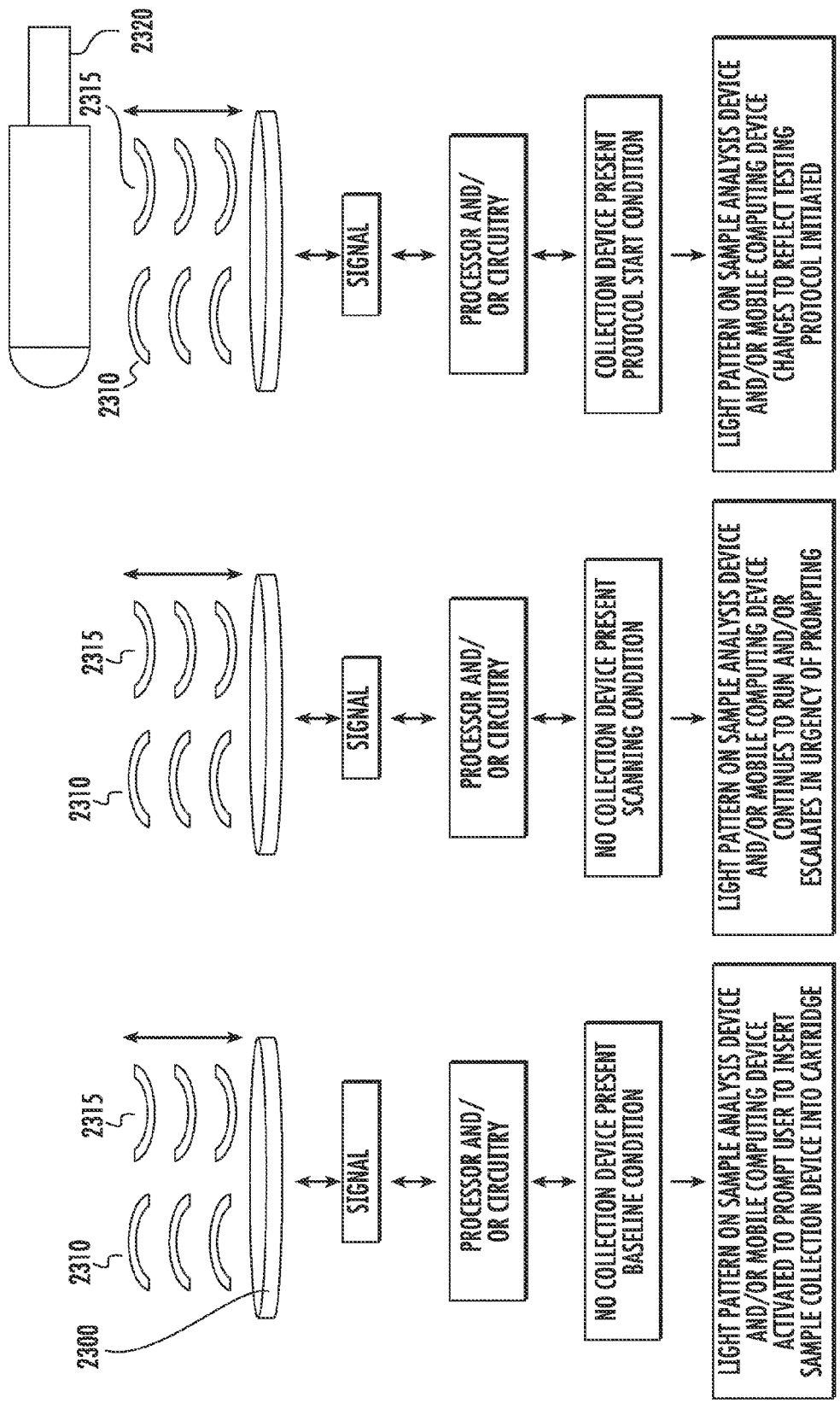
FIGS. 23A-23C schematically represent a sonicator engaged in various states of an automatic detection and automatic start protocol.

In other embodiments, detection of the sample collection device in the first reservoir occurs through resonance or signal monitoring. Specifically, as shown in FIG. 23A, upon activation of the reader, for example, as a result of coupling a cartridge to the reader, the sonicator 2300, and/or the piezoelectric element forming all or a portion of the sonicator 2300, generates a sound wave 2310 directed towards the first reservoir. In some embodiments, the sonicator 2300 or a portion thereof then deforms as a result of a reflected sound wave 315 and/or the resonance frequency of the sonicator is recorded, thereby allowing a processor and/or circuit within the reader to determine a baseline, unloaded condition. Thereafter, the sonicator 2300 enters a scanning condition shown in FIG. 23B, periodically pinging a sound wave 2310 into the first reservoir so the processor or circuit within the reader can monitor the return signal 2315 and/or resonance frequency shift of the sonicator to determine if any variation has occurred. In some embodiments, if no variation has been detected and/or the baseline unloaded condition is being established, the reader emits one or more lights or sounds prompting a user to enter a sample collection device into the cartridge. At FIG. 23C, the addition of the sample collection device 2350 causes a shift in resonance of the sonicator and/or a change to the sound wave return signal above a threshold which the processor or circuit within the reader is programmed to identify as sample collection device insertion. In various embodiments, the processor and/or circuit then returns instructions to the sonicator 2300 to initiate a sonication step of the testing protocol. In some embodiments, a light pattern on the reader changes or a sound is emitted to signify that a testing protocol has been initiated. In some embodiments, the user-prompting light or audible user-prompting sound pattern emitted during the scanning phase experiences a change in intensity or frequency to signal increased urgency to the user to input a collection device. In various embodiments, the sound waves associated with prompting the user are distinct from the sound waves emitted by the sonicator to establish the loaded vs. unloaded condition of the reservoir.

In some embodiments, a high intensity sonication procedure is performed to actively elute the sample particles, including, if present, the target analyte, into the solution of the first reservoir. The sonication procedure is also performed to achieve proper suspension of the sample preparation reagents, particularly the magnetic particles, in order to make the magnetic particles available in solution for binding with the target. Any sonicator may be used which is capable of achieving the goal of generating a gentle sonication, even at the high intensity phase, while avoiding cavitation and large shearing forces. One embodiment of an appropriate sonicator is a piezoelectric component, such as, for example, a 1.6 megahertz bending transducer piezoelectric disk at an output of less than 15 Watts.

Following the high intensity sonication, the sonic signal of the sonicator is pulsed in order to prevent the magnetic particles from settling and to continue to add energy into the system. The addition of energy enhances the hybridization between the affinity molecules on the magnetic particle, the target, and the detector agent or competitive binding agent.

The sonication profile selected by the reader varies according to the sample being tested. As used herein, "sonication profile" refers to characteristics of the delivered sonication, such as the length of time of sonication, the frequency of sonication, the intensity, etc. In various embodiments, the reader has fine-grained control over such variables. In some embodiments, for power consumption purposes, the sonicator has an "on period" in which it pulses. For example, in one embodiment, during the sonication phase, the sonicator is activated for three seconds within every 10 second window, and within those three activated seconds, the sonicator pulses at regular intervals; for example, the sonicator may generate a sound wave every 0.027 seconds. Such methods create an environment conducive to hybridization, target capture, and formation of various molecule complexes while avoiding over-consumption of power and over-heating of the sample.

Continuing with FIG. 22, the reader 2200 of various embodiments also includes one or more magnetic field generators 2240. In some embodiments the magnetic field generator 2240 may be an inductor or other electromagnetic component affixed within the reader 2200. As shown in FIG. 22, in some embodiments, the magnetic field generator 2240 is a permanent magnet. The magnetic field generator(s) 2240 are positioned such that, when a cartridge is coupled to the dock 2210, the one or more detection sensors are each disposed directly within a magnetic field created by the magnetic field generator(s) 2240. In various embodiments, the magnetic field(s) are the cause of localization; the magnetic field(s) are what induce magnetic particles and accompanying hybridized molecules to localize within the analysis zone.

In various embodiments, the base component of the cartridge has a cutout that allows for at least one permanent magnet or inductor to be positioned directly underneath the detection sensor of the circuit board component. The cutout allows the cartridge to slide into place on the dock 2210 without hitting the magnet or inductor. The cutout also allows for the magnetic field generator 2240 to be positioned as close to the detection sensor as possible. The closer the magnet field generator 2240 is to the sensor, the more force the magnet field is able to exert, meaning that smaller magnets or inductors are capable of exerting equivalent magnetic field strengths as larger, more costly magnets or inductors. The use of small magnets or inductors is particularly advantageous in embodiments having multiple magnetic fields and multiple analysis zones (for example, in embodiments configured to detect a plurality of different target analytes), because the smaller the magnet or inductor, the less the magnetic fields overlap. Smaller magnetic fields can limit the amount of cross talk between the magnets or inductors under the different detection sensors.

Additionally, as mentioned above in the discussion of the cartridge, in some embodiments of an analyte detection system, a heating element is provided to activate heat-actuated valves within the reservoir outlets. In such embodiments, the heating element delivers heat to vias on the circuit board component of the cartridge, and the vias act as conductors of heat to melt wax at precise points of time and/or within precise spatial area. In some embodiments, a plurality of heating elements are located within the reader 2200 and positioned to align with the vias of a docked cartridge. In some such embodiments, spring-loaded contacts are provided within the reader 2200 to form an effective contact between the heating elements of the reader and the via. In some such embodiments, the heating element is a resistive heating element.

In various embodiments, regardless of the location of the heating element (in the reader or the cartridge), the timing of heat delivery and valve opening is precisely timed and controlled by the reader device. For example, in some embodiments, the reader computer controls when heat-generating current flows through the heating element. The valves are actuated by heat caused by such current in the following sequence: (1) sample preparation reservoir, (2) wash reservoir, if present, then (3) chemical substrate reservoir. Actuation of each valve is timed such that: the respective valve fully actuates, the associated reservoir has time to empty its contents into the analysis channel, and at least some of the contents of the reservoir have time to travel to the absorbent pad positioned downstream of the sensors before the contents of the next reservoir is released. In some embodiments, the time between valve actuations is selected to be great enough for the absorbent pad to entirely or substantially absorb liquid present within the analysis channel. Advantageously, in such embodiments, very little mixing occurs between the contents of successive reservoirs.

In some embodiments, the precise timing of sequential valve actuation and/or determination of successful valve actuation can be determined at the processor through the usage of feedback control systems utilizing an algorithm on the processor and information derived from sensing elements, such as thermistors and electrochemical sensors. For example, an electrochemical sensor in the analysis channel can be queried to determine whether the analysis channel has liquid in it since the signal generated at the sensor will be different depending upon the presence or absence of liquid above the sensor. This signal, in combination with a processor set to logically interpret the signals, can thereby determine whether a valve has actuated properly and/or when a reservoir has fully emptied its liquid contents and when the liquid contents have been absorbed into a waste pad such that the channel is free of liquid and ready for a sequential valve actuation. In some embodiments, the processor and/or circuitry of the reader sends signals instructing a heating element to actuate a subsequent valve only after the processor and/or circuitry has received confirmation, through the feedback system, that the analysis channel is wholly or partially cleared and ready for the next step.

Figure 24:
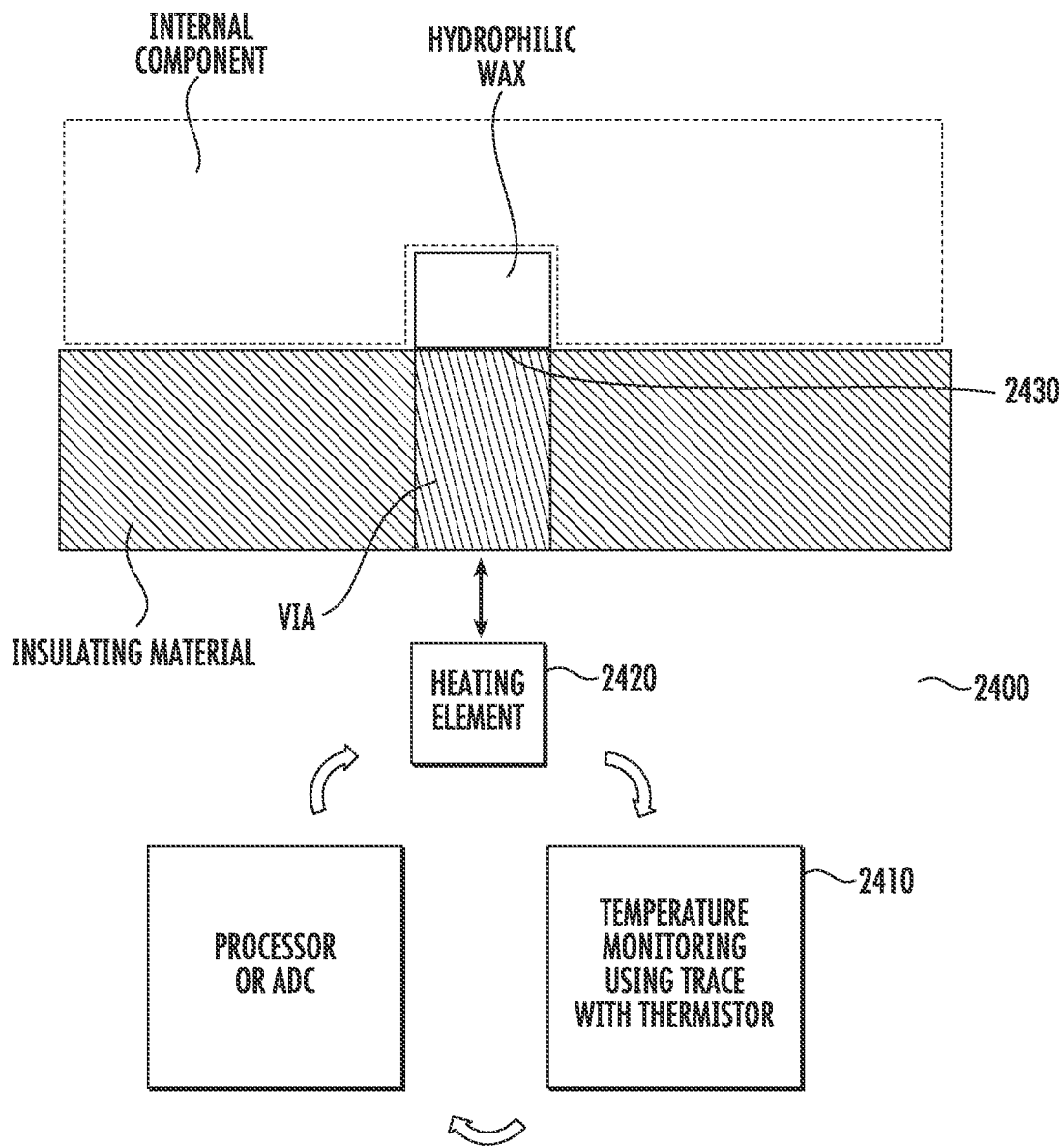
FIG. 24 depicts a schematic diagram of one embodiment of a valve feedback system.

Additionally, as shown schematically in FIG. 24, in some embodiments, a desired thermal profile of the heating element for valve actuation can be consistently achieved through the usage of an additional feedback and control system 2400 which includes: a temperature sensing element 2410, such as a thermistor, in thermal communication with a heating element 2420 positioned to actuate a heat-actuated valve 2430, and a processor 2440 set to logically interpret signals from said heating element 2420.

One embodiment of a thermal profile-controlling feedback and control system is provided in FIG. 25. Alternate FIG. 25 depicts an embodiment of a temperature sensing element 2510 in thermal communication with the via 2520 on a circuit board component 2530 of a valve actuating element. In particular, the temperature sensing element depicted is a thermistor, which has a resistance that varies with its temperature. When in electronic communication with other circuitry and/or a processor configured to interpret the electronic signals from the thermistor, the information gathered from the thermistor can be utilized to maintain consistent thermal actuation of the valve through command and control of a heating element in electronic communication with aforementioned processor. This sensing element can additionally improve safety of the sample analysis device by helping to prevent runaway escalation of temperature at the heating element in thermal communication with said thermistor by contributing sensing information that will enable a processor to shutoff the heating element if the temperature runs too hot. The depicted embodiment of FIG. 25 shows the thermistor 2510 in thermal communication with the heating element through the usage of a heat conducting element on a circuit board of the reader device, said heat conducting element being a metallic trace 2540, for example, a copper trace. Additionally, the thermistor 25510 is in thermal communication with the via 2520 of the valve unit through the use of a connector 2550 (in one embodiment, a spring loaded connector pin), which typically has high thermal conductivity. The heating element is not depicted in FIG. 25, but it can be appreciated that the heating element can be thermally coupled to the via in multiple ways, including through the usage of a trace as the thermistor is coupled to the via through a conducting trace and then through the spring loaded pin in contact with the via.

FIGS. 26A-26C depict the reader device 2200 of FIG. 22 shown through various stages of coupling to a cartridge 700. As shown, the reader 2200 includes a dock 2210, an electrical connector 2220, a sonicator 2230, and a magnetic field generator 2240 in the form of a permanent magnet. The cartridge 700 is configured to slide into the dock 2210 and couple to the reader 2200. When coupled, the electrical leads 754 of the cartridge 700 are in direct contact with the electrical connector 2220, the first reservoir 724 is disposed over the sonicator 2230, and a portion of the microfluidic analysis channel 732 is disposed over the magnetic field generator 2240 within the magnetic field.

Figure 27B:
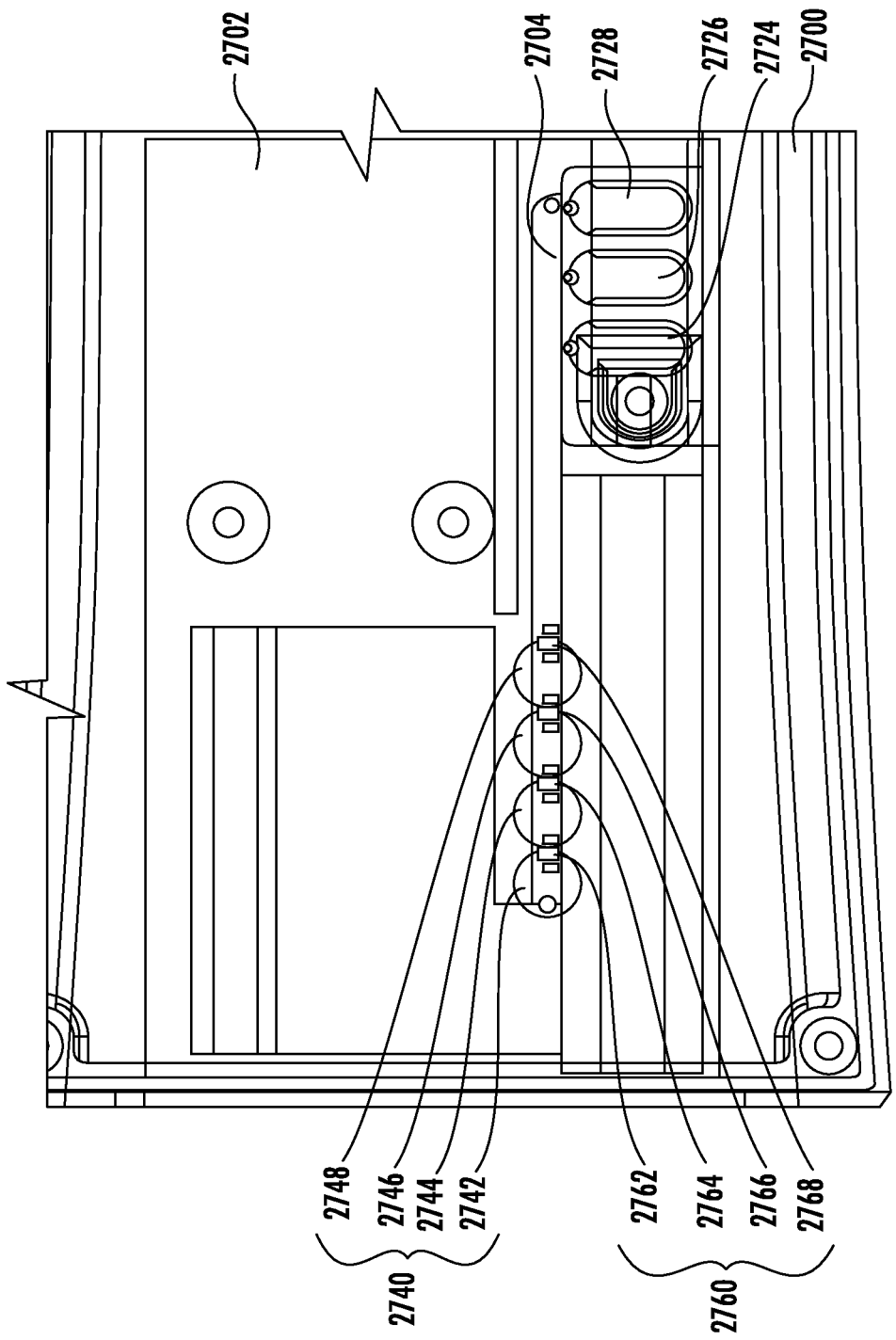

FIGS. 27A and 27B provide an additional embodiment of a reader device 2700 coupled to a cartridge 2702. The reader device of FIGS. 27A and 27B includes a plurality of magnets 2740 disposed in series below the dock of the reader 2700, positioned such that when a cartridge 2702 is coupled to the dock, the magnets 2742, 2744, 2746, 2748 are located below a plurality of detection sensors 2762, 2764, 2766, 2768, respectively. In embodiments such as the embodiment of FIGS. 27A and 27B, which are designed to detect the presence, absence, and/or quantity of a plurality of different target analytes in a sample, modifications are made to both the design of the cartridge 2702 and the reader 2700 relative to other embodiments described herein. For example, as described above, the detection of multiple different target analytes requires the inclusion of multiple populations of magnetic particles and multiple populations of detector agents and/or competitive binding agents within the first reservoir 2724. Each population of magnetic particles, detector agents, and competitive binding agents present in the reservoir 2724 is designed to have affinity to a different target analyte and include a different capture antibody, capture DNA probe or other affinity molecule. Additionally, each population of magnetic particles present in the reservoir 2724 has a unique identifying physical characteristic, such as a different size, magnetic response, density, or any combination thereof.

In one embodiment in which multiple populations of magnetic particles are present to detect the presence of a plurality of different target analytes, dead-end filtration is used to separate the populations for detection. In such an embodiment, as the magnetic particles flow out of the first reservoir 2724 and into the analysis channel 2704, a sequence of filters provided within the analysis channel 2704 are encountered. Moving in a downstream direction, the filters are ordered by pore size with the first filter having the largest pores and the last filter having the smallest pores. Each filter is placed in close proximity to a detection mechanism designated to detect a particular detector agent or a product of a particular detector agent. For example, in some embodiments, the detection mechanism is an electrochemical sensor designated to detect oxidation that occurs among a particular population of hybridized magnetic particles. Magnetic particles smaller than the first filter pore size will pass through the filter with the flow of liquid down the channel. Magnetic particles larger than the pore size of the first filter will remain behind, in close proximity to the first sensor 2762. Through the use of successive filters of decreasing pore size, the magnetic particle populations are separated and localized over the different detection sensors 2760. In this manner, reactions such as oxidation reactions among different populations of hybridized magnetic particles and target analytes can then be monitored in the manner described elsewhere herein to identify the presence, absence, and/or quantity of each of a plurality of target analytes.

This process can be enhanced through the use of magnetism. Magnetic particles of the same material composition vary in their magnetic response with the square of the diameter of the magnetic particle. Therefore, a magnetic field will interact differently on magnetic particles of different size, thus allowing a sorting mechanism to take place. This differential magnetic response may be exploited in some embodiments to enhance separation speed and specificity. As the magnetic particles leave the first reservoir, a magnetic field may be applied to the analysis channel in order to at least partially order the magnetic particles by size. Since larger magnetic particles will feel the magnetic force more strongly than smaller magnetic particles, the larger ones will move more slowly downstream relative to the smaller magnetic particles. This results in a preference for smaller magnetic particles to progress down the analysis channel 2704 earlier than larger magnetic particles, which decreases the likelihood of magnetic particle-based clogging of pores. Magnetic particle-based clogging of a pore may decrease multiplexing specificity and may prevent proper testing altogether by restricting the flow of liquid needed to wash away excess enzyme and to provide chemical substrate to the captured detector agents.

In some embodiments, cross flow filtration technology is used to prevent membrane fouling common with dead-end filtration. In such embodiments, the magnets or inductors are positioned to exert a perpendicular or other non-parallel magnetic force relative to the direction of flow. Such a placement of the aligning magnets or inductors causes magnetic particles to be pulled to the side of the analysis channel where the filters are located, if they are of sufficient size to be acted upon by the provided magnet field generator. In such embodiments, the magnet field sizes are selected such that a magnetic particle will be pulled to the side of the analysis channel 2704 to encounter a filter just upstream of the first filter having a pore size smaller than the size of the magnetic particle.

Alternatively, the populations of magnetic particles and target analytes can be separated through the use of magnetism alone. Because the magnetic force response of a magnetic particle scales with the square of the diameter of the particle, separation and localization of magnetic particle populations can be achieved in a single channel without the use of membranes by providing a plurality of magnets or inductors located on the reader device or cartridge creating different magnetic field strengths at different locations of the analysis channel 2704. Specifically, moving in a downstream direction, magnetic field generators of increasing magnetic field strength are encountered. The largest magnetic particles are localized at the first sensor because they are unable to escape the first magnetic field, which is just strong enough to capture the largest magnetic particles, but is not strong enough to capture any other size of magnetic particles. Magnetic particle populations will travel downstream with the flow of liquid until they are caught by the magnetic field tailored for their particular magnetic particle size located over a detection sensor 2760 provided for detecting oxidation reactions among their population. The second weakest magnetic field will capture the population of magnetic particles with the second largest diameter; the third weakest magnetic field will capture the population of magnetic particles with the third largest diameter, and so on. The smallest magnetic particles are captured by the strongest magnetic field. This allows each population of magnetic particles to localize over a different detection sensor and detection proceeds as described above. The magnetic fields can be varied through at least a couple methods. In some embodiments, each magnet or inductor is a different size; the larger the magnet or inductor, the larger its magnetic field. In other embodiments, such as the embodiment shown in FIGS. 27A and 27B, magnets 2740 are placed at varying depths relative to the plane of the analysis channel 2704. The upstream-most magnet 2748, is placed furthest to the analysis channel 2702, and thus exerts the strongest magnetic field on the channel 2704. The downstream-most magnet 2742, is placed closest to the analysis channel 2702, and thus exerts the strongest magnetic field on the channel 2704.

Importantly, in various embodiments described herein, the magnetic attraction between the magnetic particles and the one or more magnet fields is sufficiently strong to cause the magnetic particles to remain localized over the one or more magnetic field generators as a wash solution and/or a liquid carrying chemical substrates flows over the magnetic particles.

The Detection System

Figure 28B:
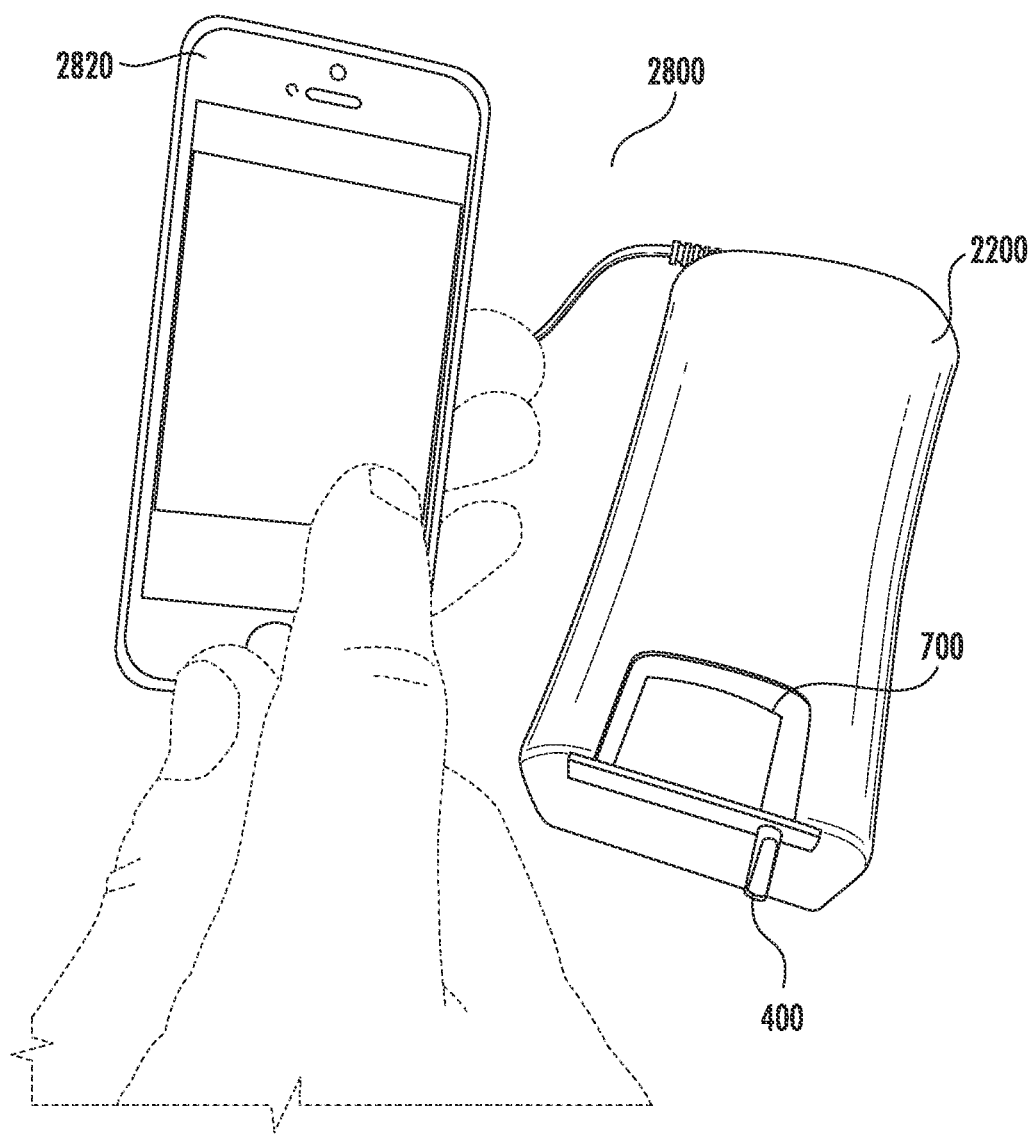
FIG. 28B depicts the target analyte detection system of FIG. 28A with the various components coupled together and in use.

One embodiment of a detection system 2800, which includes the sample collection device 400 of FIG. 4, the cartridge device 700 of FIGS. 7A and 7B, and the reader device 2200 of FIG. 22, is provided in FIGS. 28A and 28B. The devices forming the system are shown separately, prior to use, in FIG. 28A and in a coupled configuration, in use, in FIG. 28B. The sample collection device 400 of various embodiments, including the embodiment of FIG. 28A, is disposable and configured for one-time use. It may come within removable sterile packaging. Once inserted into the input tunnel 712 of the cartridge 700, the sample collection device 400 is locked into a permanent fixed engagement and cannot be used again. Similarly, the depicted cartridge 700 is disposable and configured for one-time use. Once the sample collection device 400 locks into place within the input tunnel 712 of the cartridge 700, the cartridge 700 cannot be used again. The cartridge 700, can, however, be removed from the reader 2200. In various embodiments, the cartridge 700 and the reader 2200 are configured to be separably coupled, and the cartridge 700 can be inserted and removed from the dock of the reader 2200 at least before and after implementation of a detection protocol. In some embodiments, the reader 2200 may include a locking mechanism for temporarily locking the cartridge 700 into place, and limiting removal, during the duration of a detection test cycle. The reader 2200 of various embodiments is reusable.

Additionally, in certain embodiments, the reader 2200, and the entire detection system 2800, are configured for non-clinical, consumer-directed use. Accordingly, the system 2800 of some embodiments is easy to use and generates results quickly. In some embodiments, results of a target analyte detection protocol are generated in 30 minutes or less from the time a sample from a sample collection device 400 is inserted into the system's cartridge 700. In some embodiments, the results are generated in less than 20 minutes, in some embodiments, less than 10 minutes, and in some embodiments, results are generated in less than 5 minutes. Additionally, the consumer-directed system of some embodiments is small for an unobtrusive presence within a home, school, office, or other place of employment. In some embodiments, the system is less than 30 cm in height, less than 30 cm in width, and less than 30 cm in length; in some embodiments, the height, width, and length are each less than 20 cm; in some embodiments, one or more of the height, width, and length are less than 10 cm. In some embodiments, the cartridge 700, sample collection device 400, and reader 2200 together form a system 2800 approximately the size of a smartphone or other mobile computing device. In some embodiments, the system is sized and configured to be portable. In such embodiments, in addition to a compact, handheld design, all liquids within the sample are properly sealed and separated such that no leaking or premature oxidation reactions will occur due to jostling of the system components while on the go.

To promote use by lay people in non-clinical settings, the system 2800 of some embodiments is designed to be "dummy proof" by including a self-activating and self-run detection protocol. For example, FIG. 28B depicts an example in which the cartridge 700 has been placed into the dock 2210 of the reader 2200 and the sample collection device 400 has been inserted into the input tunnel 712 of the cartridge 700. In the depicted embodiment, loading the cartridge 700 into the reader 2200 established an electrical connection between the pins of the cartridge 700 and the reader 2200, thereby completing a circuit within the reader 2200, which automatically activated the reader. Upon being activated, the reader 2200 of some embodiments activates its sonicator, if present, utilizing the sonicator to detect entry of a sample collection device 400 into the first reservoir. Upon detection, the reader 2200 of various embodiments is configured to initiate a detection protocol automatically without any further human intervention. The automated start ensures that mixing of reagents and sample within the first reservoir occurs consistently at a fixed time following insertion of the sample collection device, leading to consistent test results. In other embodiments, where no sonicator is present, the testing protocol may initiate when a user presses a "go", "run", "start", or other similar button or icon on the reader 2200 or a remote computing device 2820.

Figure 29A:
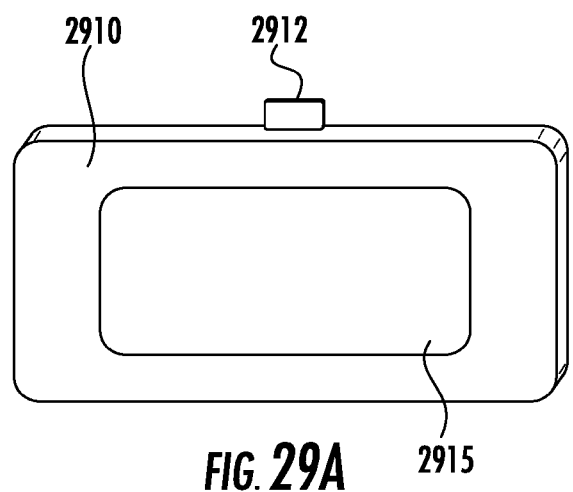
FIG. 29A depicts another embodiment of a reader device.
Figure 29B:
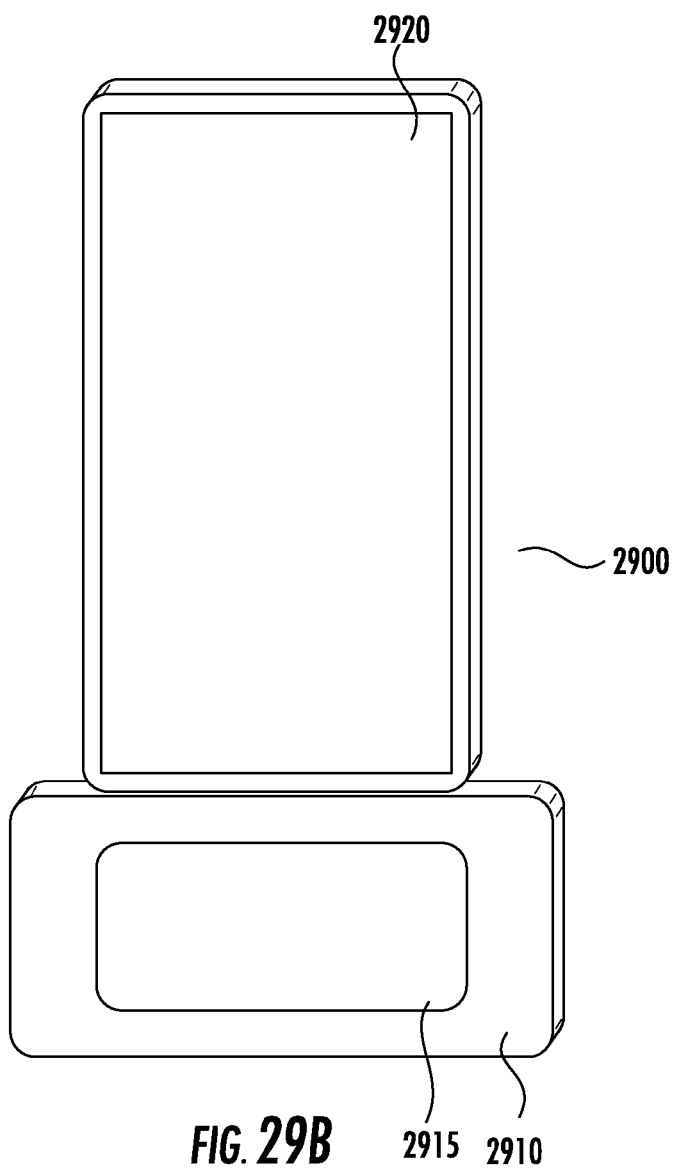
FIG. 29B depicts the reader device of FIG. 29A directly coupled to a remote computing device.

As described in more detail below, and as shown in FIGS. 28A and 28B, in some embodiments, the system 2800 includes a remote computing device 2820. The remote computing device 2820 may be a mobile computing device, such as, for example, a smartphone, tablet, or wearable device, or a laptop or other computer. As shown in FIG. 28A, in some embodiments, the reader 2200 communicates with the remote computing device 2820 wirelessly. In other embodiments, a removable wired connection, such as a cable connection, is provided between the reader 2200 and the remote computing device 2820. In still other embodiments, such as the embodiment of FIGS. 29A and 29B, an analyte reader 2910 having a cartridge docking station 2915, within the system 2900, removably couples to the remote computing device 2920 directly, for example, by connecting via a plug 2912 into a headphone jack or electrical charging port.

Figure 30:
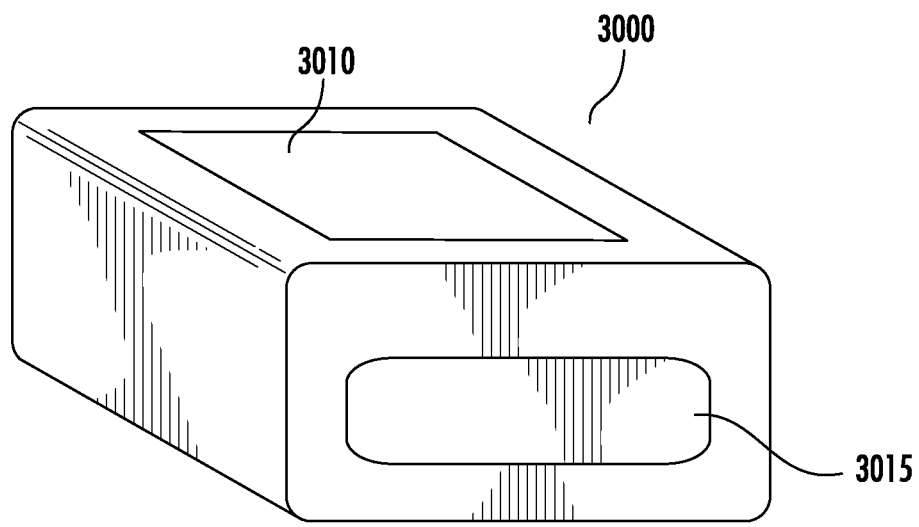
FIG. 30 depicts another embodiment of a reader device.

In various embodiments, the remote computing device may be included within the system: to provide for more computing power and/or more memory; to provide a wireless transceiver for pulling data from, and transmitting data to, a remote server; and/or to provide a display screen and user interface. A remote computing device is not needed within every embodiment. For example, as shown in FIG. 30, in some embodiments, the reader 3000 includes a processor and memory (not shown), a dock 3015 for a cartridge, as well as a touchscreen or other user interface 3010. In such embodiments, the reader is configured to identify the proper test protocol, run the test protocol, analyze the raw results received from the sensors in the system, and display digital results to a user. The reader of such embodiments may further include a wireless receiver and transmitter for accessing and transmitting data from remote servers.

Figure 31:
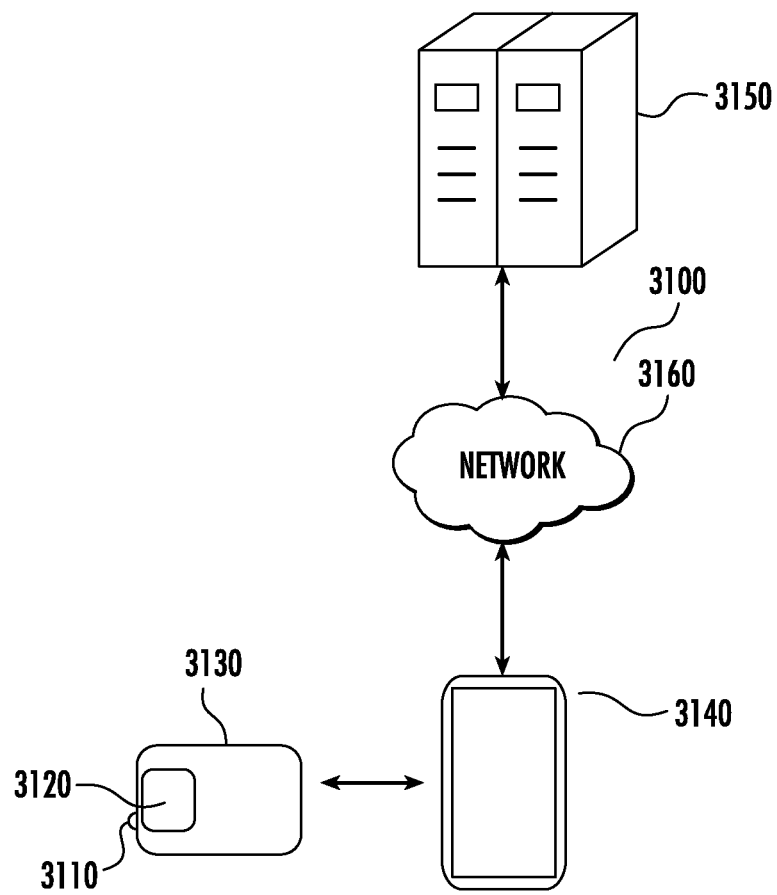
FIG. 31 provides a schematic diagram of one embodiment of an analyte detection system.

One embodiment of an analyte detection system is shown schematically in FIG. 31. FIG. 31 provides a schematic illustration of the interactions between computerized components within one embodiment of an analyte detection system 3100. One skilled in the art will appreciate that the embodiment is illustrative in nature only and various components may be added, deleted, or substituted and various different hierarchies and modes of communication between the devices may be employed. In the depicted example, the detection system 3100 is formed of a plurality of computerized devices, including a reader 3130, a device having a user interface 3140, and a server 3150. While not computerized, the system 3100 additionally includes a sample collection device 3110 and a cartridge 3120 shown coupled to the reader 3130. It should be understood that in certain embodiments described with reference to FIG. 31, the reader 3130 may represent any reader embodiment described elsewhere herein, such as for example, reader 2200, reader 2910, or reader 3000. Similarly, the device having a user interface 3140 may represent any such device described herein, such as the mobile computing device 2820 or 2920. The cartridge 2820 may represent any cartridge embodiment described herein, such as cartridge 700, 800, or 900 and the sample collection device 2810 may represent any sample collection device described herein, such as sample collection device 400 or 600. The system 3100 includes a communication network 3160 through which some or all of the various devices communicate with one another. The network can be a local area network (LAN) or a wide area network (WAN). In some embodiments, the network is a wireless communication network, such as, for example, a mobile WiMAX network, LTE network, Wi-Fi network, or other wireless network. In other embodiments, the communication between the computer having a user interface 3140 and the server 3150 occurs over the internet via a wired network, such as a DSL cable connection.

In some embodiments, the reader 3130 and the device having a user interface 3140 are not separate devices, but rather, are both provided within the reader device 3130, for example, as shown in FIG. 30. In such embodiments, communication between the reader processor and the user interface occurs internally within the reader 3130 via the transmission of electrical signals.

In other embodiments, the reader 3130 and the device having a user interface 3140 are separate devices. In some embodiments, the device with the user interface 3140 is a smartphone or other mobile computing device. Communication between the reader 3130 and the mobile computing device 3140 may occur, wirelessly, for example, using Bluetooth®, near-field communications, or other radiofrequency technology. Alternatively, transmission of signals between the reader 3130 and the mobile computing device 3140 may occur over a cord, cable, or other wired or direct connection. In various embodiments, the mobile computing device or other device having a user interface 3140 includes a software application for a front-end, graphical user interface for presenting test results to a user.

In various embodiments, the reader 3130 is configured to control the tests and processes needed to detect and/or quantify target analyte within a sample. To do so, a significant amount of information may be stored within the memory of the reader 3130. Alternatively, some or all of the information may be stored within the server 3150 and accessible by the reader 3130 via the communication network 3160. Such information includes, for example a database of cartridge keys, which identifies each cartridge type by the signal generated by the cartridge's unique identifying resistor label. The information also includes test protocols associated with each cartridge key. The test protocols may specify such details as how long to mix sample preparation reagents through sonication, the frequency of the sonication, when to heat the various heat-sensitive valves, etc. The information may also include correlation tables for each cartridge type, which correlate detected sensor signals to the absence, presence, and/or a specific quantity of a target analyte. Additionally, the information stored by the reader 3130 and/or the server 3150 may include one or more past results. In some embodiments, the reader 3130 stores test results at least until the reader 3130 comes into communication with a remote computing device; at such time, the results may be transmitted to the remote computing device (mobile computing device 3140 or server 3150) for display and/or long-term storage.

In some embodiments, the server 3150 also stores user profiles, which may include biographical information entered into the system by a user through the device having a user interface 3140. In some such embodiments, a log of test results for each user is also stored by the server 3150 and accessible for viewing by the user through transmission of such data to the device with a user interface 3140.

In one embodiment, when a cartridge 3120 is loaded into the reader 3130, the reader 3130 detects signals from a label, such as a resistor label or electronic barcode, on the cartridge 3120 to detect the cartridge type. The reader 3130 compares the detected signals to a database of known label signals or cartridge keys to determine which cartridge type is present. If the detected label signal is not found within the database of cartridge keys, the reader 3130 may transmit a message to a server 3150 requesting updates to the database of cartridge keys. The reader 3130 may transmit the message directly to the server 3150 or indirectly by way of the mobile computing device 3140. The reader 3130 may additionally receive, directly or indirectly, data for cartridge key database updates. The data may include new cartridge types and the cartridge keys and test protocols corresponding to each new cartridge type. In some embodiments, the reader 3130 then identifies and implements the test protocol associated with the detected cartridge type. Upon receiving signals from a detection sensor, the reader 3130 of some embodiments compares the signals to a correlation table to process the signals and generate meaningful results. The results may be transmitted to the device with a user interface 3140 for display to a user. One skilled in the art will appreciate that the various information stored by the computing devices of the detector system 3100 may be stored by any one or more of the devices and may be accessible to the other devices through the receipt and transmission of data signals.

The Computerized Methods of Detection

Figure 32:
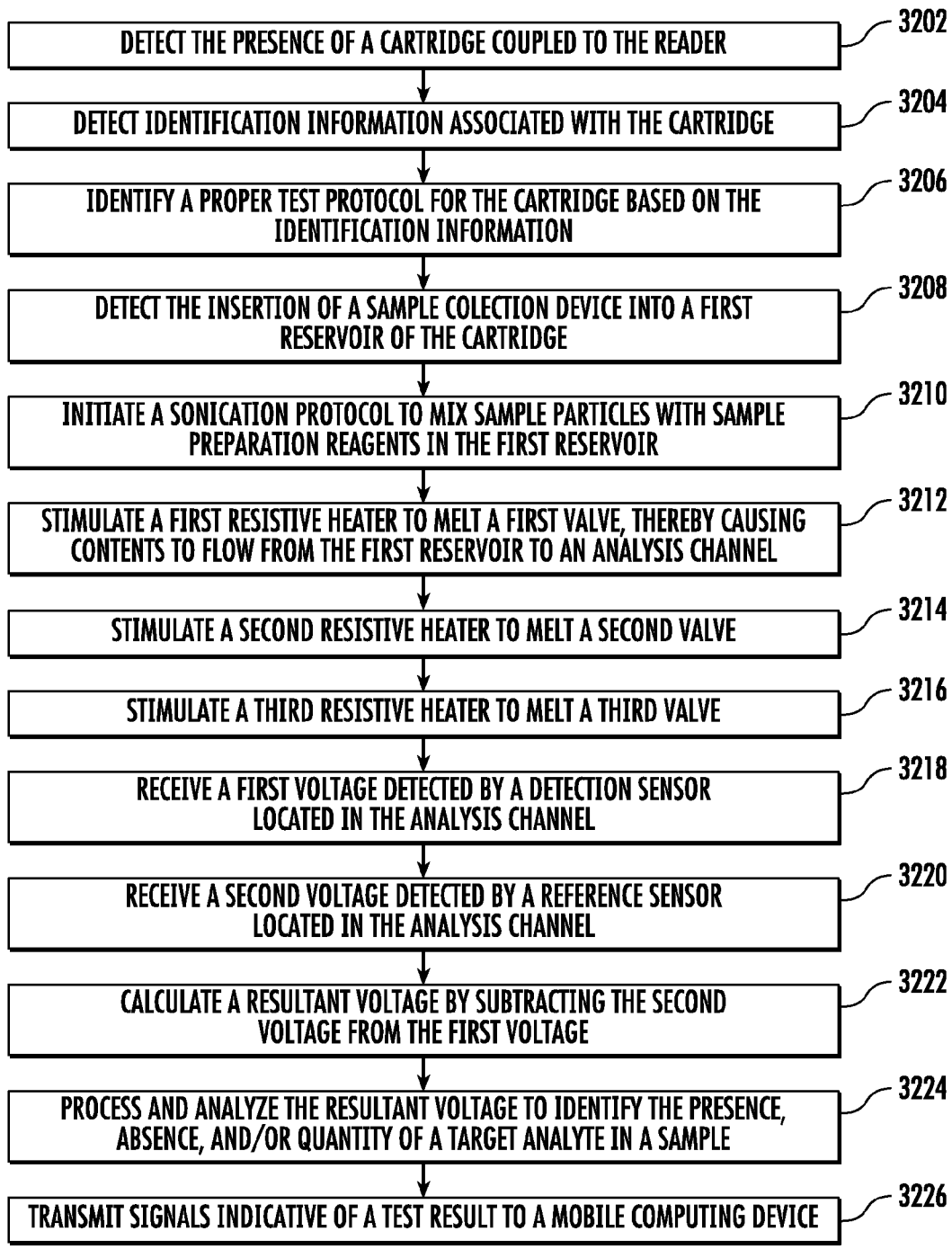
FIG. 32 provides a flowchart of one embodiment of a method for detecting the presence, absence, and/or quantity of a target analyte in a sample.

As mentioned above, the computerized reader largely controls the operations of the detection system. The reader includes a processor and memory, the memory having instructions stored thereon for implementing various methods needed to successfully detect the presence, absence, and/or quantity of target analyte within a collected sample. For example, an embodiment of one method performed by the computerized reader in an automated manner is provided in FIG. 32.

At block 3202, the computerized reader detects the presence of a cartridge loaded into or onto the reader. For example, in some embodiments, a cartridge is coupled to the reader such that electrical leads on the cartridge come into physical contact with electrical pins on the reader, completing a circuit that turns on the reader and signals the reader to the presence of a cartridge.

At block 3204, the reader detects identification information associated with the cartridge. For example, the cartridge of some embodiments includes a unique identification key on its circuit board component, which generates signals unique to the particular cartridge type of the cartridge, allowing the reader to distinguish between cartridge types. The identification key may be a resistive element, for example, a surface mount resistor or a resistive ink-based element having a unique size or shape, or it may be another unique electrical signal generator.

The reader's processor receives the unique identification key signals from the reader's circuitry which detected the signals, and as shown at block 3206, identifies a proper test protocol for the cartridge based on the unique identification key. In some embodiments, the reader's processor compares the unique identification key signals to a database of identification keys stored in memory. Within the database of some embodiments, each identification key is associated with a particular cartridge type and test protocol. If the identification key signals received from the processor match a key in the database, the corresponding test protocol will be opened and executed by the processor. If the identification key signals do not match a key in the database, the processor may communicate with a remote computing device such as a mobile computing device and/or a server to signal that an unidentifiable cartridge has been detected. In some embodiments, the reader downloads updates directly from a server or indirectly with the mobile computing device acting as an intermediary. In some embodiments, when an unknown cartridge type is detected, a user is prompted via the user interface of the mobile computing device, to download updates; in other embodiments, the updates are downloaded automatically. In various embodiments, the updates include newly developed cartridge identification keys and test protocols. Once the new identification keys and test protocols are downloaded, they will be added to the reader's database of supported tests so that future tests with this cartridge type will automatically be recognized and implemented without the need for communicating with remote computing devices.

As shown at block 3208, in various embodiments, the computerized reader detects insertion of a sample collection device into a first reservoir of the cartridge. Various processes can be implemented to accomplish this detection, as provided in more detail in the discussion of sonication above. In various embodiments, the reader's processor receives signals from a sonicator element comprised partially or wholly of a piezoelectric element, in the reader. By monitoring the sonicator element to identify changes in the signals generated from a mechanical event within the reservoir, the processor can identify when a change in pressure and/or a change in resonance and/or a change in a reflected signal (pressure or sound wave) has occurred in the first reservoir of the cartridge through the ability of the piezoelectric component to transduce mechanical signals into electric signals which can be amplified and understood through a combination of circuitry and processor in electronic communication with said piezoelectric element; such changes are indicative of entry of a sample collection device into the reservoir.

At block 3210, the reader's processor sends signals to the sonicator to instruct it to initiate a sonication protocol to mix a plurality of reagents, affinity molecules, and sample particles within a liquid disposed within the first reservoir. In various embodiments, the resulting mixture includes magnetic particles bound to: target analytes, target analytes and detector agents, and/or competitive binding agents. As used herein, sandwich complexes refer to magnetic particles bound directly or indirectly to target analytes and detector agents; competitive binding complexes refer to magnetic particles bound to competitive binding agents. Each sandwich complex and competitive binding complex include a detector agent bound within the complex. In one embodiment described here, the detector agent is an oxidizing enzyme.

As shown at block 3212, in some embodiments, the reader generates a current, which heats or otherwise stimulates a first heating element, thereby causing heat to transfer to a first heat-actuated valve within the cartridge. In some embodiments, this causes the valve to melt or undergo another phase change, which allows liquid to flow out of the first reservoir into an analysis channel via capillary action. As the liquid flows, it transports the mixture with it, and the magnetic particles within the mixture, including magnetic particles within sandwich complexes and/or competitive binding complexes, localize over one or more magnetic fields within the analysis channel, forming one or more localized samples.

Optionally, at block 3214, the reader generates a current, which heats or otherwise stimulates a second heating element such that a second valve within the cartridge undergoes a phase change and a wash solution flows out of a second reservoir into the analysis channel. In various embodiments, the wash solution removes, from the one or more localized samples, oxidizing enzymes (or other detector agents) that are not indirectly bound to magnetic particles.

At block 3216, the reader generates a current, which heats or otherwise stimulates a third heating element such that a third valve within the cartridge undergoes a phase change and a solution of substrates flows out of a third reservoir into the analysis channel. In various embodiments, when the detector agent is an oxidizing enzyme, the oxidizing enzymes within the sandwich complexes and/or competitive binding complexes of each localized sample oxidize the substrate molecules present in the aqueous media used to transport said substrate molecules. In embodiments in which sandwich complexes are present, oxidation occurs at an electrochemical cell formed by an electrochemical sensor and the volume of liquid substantially over it and electrons flow from the working electrode of the electrochemical sensor to the volume substantially above said sensor in a quantity proportional to a quantity of target analyte present within the localized sample. In embodiments in which competitive binding complexes are present, oxidation occurs at an electrochemical cell formed by an electrochemical sensor and the volume of liquid substantially over said sensor and electrons flow from working electrode of the electrochemical sensor in a quantity inversely proportional to a quantity of target analyte present within the localized sample.

At block 3218, the reader's processor receives from the reader's electric connector a first signal detected at the electrochemical sensor. In various embodiments, the signal is a voltage or current signal. At least a portion of the signal is caused by the oxidation of the substrate. At block 3220, the reader's processor receives from the reader's electric connector a second signal detected by a reference sensor. At block 3222, the reader's processor calculates a resultant signal by subtracting or applying another algorithm to remove the second signal from the first signal to account for and/or eliminate noise that may be present within the system. At block 3224, the reader's processor processes and analyzes the resultant signal to identify the presence and/or quantity of a target analyte. Optionally, as shown at block 3226, in some embodiments, the reader transmits signals indicative of a test result to a mobile computing device for further processing, storage, transmission to a server, and/or display of results to a user.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

What is claimed is:

1. A microfluidic cartridge comprising:
   a fluid-holding reservoir comprising an outlet;
   a microfluidic channel configured to receive fluid from the fluid-holding reservoir through the outlet;
   a printed circuit board;
   a via positioned in the printed circuit board such that the via is positioned under, over, or adjacent to the outlet of the fluid-holding reservoir;
   a valve comprising a phase-changeable material, wherein:
      in a first state, the phase-changeable material is deposited on the via and extends into the outlet, occluding an entire cross-section of the outlet, and
      in a second state, the phase-changeable material does not occlude the entire cross-section of the outlet;
   a heating element configured to heat the via such that the via heats the phase-changeable material deposited on the via to transition the phase-changeable material from the first state to the second state to permit the fluid to flow from the fluid-holding reservoir through the outlet and into the microfluidic channel; and
   a cartridge housing configured to enclose the fluid-holding reservoir, the microfluidic channel, the printed circuit board, the via, the valve, and the heating element.

2. The microfluidic cartridge of claim 1, wherein the valve is configured to irreversibly transition from the first state to the second state.

3. The microfluidic cartridge of claim 1, wherein, in the first state, the phase-changeable material is in a solid or semi-solid state.

4. The microfluidic cartridge of claim 1, wherein the phase-changeable material transitions from the first state to the second state at a temperature between 50 and 100 degrees Celsius.

5. The microfluidic cartridge of claim 1, wherein the phase-changeable material has a minimum height necessary to occlude the entire cross-section of the outlet.

6. The microfluidic cartridge of claim 1, wherein the phase-changeable material is a hydrophilic wax comprising at least one of hexadecanol and octodecanol.

7. The microfluidic cartridge of claim 6, wherein an amount of hydrophilic wax deposited on the via is below 1 microliter in a liquid state.

8. The microfluidic cartridge of claim 1, further comprising a spring-loaded contact providing effective contact between the heating element and the via.

9. The microfluidic cartridge of claim 1, wherein the heating element is activated through a transistor.

10. The microfluidic cartridge of claim 1, wherein the heating element is a resistive heating element.

11. The microfluidic cartridge of claim 10, wherein the resistive heating element comprises a serpentine trace on the printed circuit board.

12. The microfluidic cartridge of claim 1, wherein the heating element is coupled to a processor.

13. The microfluidic cartridge of claim 12, wherein the processor is configured to execute instructions stored in a memory, and the instructions, when executed, cause the processor to activate the heating element at a programmed time.

14. The microfluidic cartridge of claim 1, further comprising a feedback-and-control system to achieve a consistent thermal profile at the via.

15. The microfluidic cartridge of claim 1, wherein the outlet is a semicircle with a boundary extension.

16. The microfluidic cartridge of claim 1, wherein the cartridge housing comprises two lateral cover components configured to be coupled together to enclose the fluid-holding reservoir, the microfluidic channel, the printed circuit board, the via, the valve, and the heating element.

17. The microfluidic cartridge of claim 1, wherein the outlet is located on an angled bottom of the fluid-holding reservoir at a lowest height of the fluid-holding reservoir.

18. The microfluidic cartridge of claim 1, wherein the phase-changeable material adheres to at least one inner wall of the fluid-holding reservoir.

19. The microfluidic cartridge of claim 1, further comprising one or more additional valves each aligned with a respective one or more additional outlets connecting one or more additional reservoirs to the microfluidic channel.

* * * * *